(12) United States Patent
Williams et al.

(10) Patent No.: US 10,041,062 B2
(45) Date of Patent: Aug. 7, 2018

(54) SYSTEM AND METHOD FOR PROCESSING AND DETECTING NUCLEIC ACIDS

(71) Applicant: NeuMoDx Molecular, Inc., Ann Arbor, MI (US)

(72) Inventors: Jeffrey Williams, Ann Arbor, MI (US); Sundaresh Brahmasandra, Ann Arbor, MI (US); Michael T. Kusner, Ann Arbor, MI (US)

(73) Assignee: NeuMoDx Molecular, Inc., Ann Arbor, MI (US)

( * ) Notice: Subject to any disclaimer, the term of this patent is extended or adjusted under 35 U.S.C. 154(b) by 202 days.

(21) Appl. No.: 15/134,765

(22) Filed: Apr. 21, 2016

(65) Prior Publication Data

US 2016/0230215 A1      Aug. 11, 2016

Related U.S. Application Data

(63) Continuation of application No. 14/704,215, filed on May 5, 2015, now Pat. No. 9,441,219, which is a (Continued)

(51) Int. Cl.
*C12N 15/10* (2006.01)
*B01L 3/00* (2006.01)
(Continued)

(52) U.S. Cl.
CPC .......... *C12N 15/1013* (2013.01); *B01L 3/502* (2013.01); *B01L 3/508* (2013.01);
(Continued)

(58) Field of Classification Search
CPC ....... B29C 66/71; B29C 65/08; B29C 65/606; B29C 66/81423; B29C 66/8322;
(Continued)

(56) References Cited

U.S. PATENT DOCUMENTS 776,747 A    12/1904 Kling
778,036 A    12/1904 Hepp et al.
(Continued)

FOREIGN PATENT DOCUMENTS

CN     101432698 A    5/2009
CN       1773190 B    5/2010
(Continued)

OTHER PUBLICATIONS

Compton, Cancer and Metastasis Rev., vol. 11, pp. 105-119 (1992).

*Primary Examiner* — Nathan A Bowers
*Assistant Examiner* — Lydia Edwards
(74) *Attorney, Agent, or Firm* — Jeffrey Schox

(57) ABSTRACT

A system and method for processing and detecting nucleic acids from a set of biological samples, comprising: a capture plate and a capture plate module configured to facilitate binding of nucleic acids within the set of biological samples to magnetic beads; a molecular diagnostic module configured to receive nucleic acids bound to magnetic beads, isolate nucleic acids, and analyze nucleic acids, comprising a cartridge receiving module, a heating/cooling subsystem and a magnet configured to facilitate isolation of nucleic acids, a valve actuation subsystem configured to control fluid flow through a microfluidic cartridge for processing nucleic acids, and an optical subsystem for analysis of nucleic acids; a fluid handling system configured to deliver samples and reagents to components of the system to facilitate molecular diagnostic protocols; and an assay strip configured to combine nucleic acid samples with molecular diagnostic reagents for analysis of nucleic acids.

20 Claims, 24 Drawing Sheets

Related U.S. Application Data continuation of application No. 13/766,359, filed on Feb. 13, 2013, now Pat. No. 9,050,594, and a continuation of application No. 13/765,996, filed on Feb. 13, 2013, now Pat. No. 9,738,887.

(60) Provisional application No. 61/667,606, filed on Jul. 3, 2012, provisional application No. 61/598,240, filed on Feb. 13, 2012.

(51) Int. Cl.
| | | |
|---|---|---|
| *C12M 3/00* | (2006.01) | |
| *C12Q 1/68* | (2018.01) | |
| *B01L 7/00* | (2006.01) | |
| *C12Q 1/686* | (2018.01) | |
| *B01L 9/00* | (2006.01) | |
| *C12Q 1/6806* | (2018.01) | |
| *C12Q 1/6813* | (2018.01) | |
| *C12N 13/00* | (2006.01) | |
| *B29C 65/08* | (2006.01) | |
| *B29C 65/60* | (2006.01) | |
| *B29C 65/00* | (2006.01) | |
| *B29L 31/00* | (2006.01) | |
| *B29C 65/48* | (2006.01) | |

(52) U.S. Cl.
CPC ......... *B01L 3/5027* (2013.01); *B01L 3/50273* (2013.01); *B01L 3/502707* (2013.01); *B01L 3/502723* (2013.01); *B01L 3/502738* (2013.01); *B01L 3/502761* (2013.01); *B01L 3/527* (2013.01); *B01L 3/567* (2013.01); *B01L 7/52* (2013.01); *B01L 7/525* (2013.01); *B01L 9/00* (2013.01); *C12M 23/42* (2013.01); *C12Q 1/68* (2013.01); *C12Q 1/6806* (2013.01); *C12Q 1/686* (2013.01); *C12Q 1/6813* (2013.01); *B01L 3/5025* (2013.01); *B01L 3/502746* (2013.01); *B01L 2200/025* (2013.01); *B01L 2200/0605* (2013.01); *B01L 2200/0615* (2013.01); *B01L 2200/0668* (2013.01); *B01L 2200/0684* (2013.01); *B01L 2200/0689* (2013.01); *B01L 2200/10* (2013.01); *B01L 2200/12* (2013.01); *B01L 2200/142* (2013.01); *B01L 2300/021* (2013.01); *B01L 2300/022* (2013.01); *B01L 2300/044* (2013.01); *B01L 2300/06* (2013.01); *B01L 2300/0609* (2013.01); *B01L 2300/0627* (2013.01); *B01L 2300/0636* (2013.01); *B01L 2300/0672* (2013.01); *B01L 2300/0681* (2013.01); *B01L 2300/087* (2013.01); *B01L 2300/0809* (2013.01); *B01L 2300/0816* (2013.01); *B01L 2300/0861* (2013.01); *B01L 2300/0864* (2013.01); *B01L 2300/0867* (2013.01); *B01L 2300/0883* (2013.01); *B01L 2300/0887* (2013.01); *B01L 2300/0893* (2013.01); *B01L 2300/123* (2013.01); *B01L 2300/14* (2013.01); *B01L 2300/16* (2013.01); *B01L 2300/1822* (2013.01); *B01L 2300/1827* (2013.01); *B01L 2400/043* (2013.01); *B01L 2400/0406* (2013.01); *B01L 2400/0478* (2013.01); *B01L 2400/0481* (2013.01); *B01L 2400/0487* (2013.01); *B01L 2400/065* (2013.01); *B01L 2400/0622* (2013.01); *B01L 2400/0655* (2013.01); *B01L 2400/0694* (2013.01); *B01L 2400/086* (2013.01); *B29C 65/08* (2013.01); *B29C 65/484* (2013.01); *B29C 65/606* (2013.01); *B29C 66/71* (2013.01); *B29C 66/81423* (2013.01); *B29C 66/8322* (2013.01); *B29L 2031/756* (2013.01); *C12N 13/00* (2013.01)

(58) Field of Classification Search
CPC ......... B29K 2021/00; B01L 2200/0684; B01L 2200/0689; B01L 2200/10; B01L 2300/1827; B01L 2400/0487; B01L 2400/0655; B01L 3/5027
See application file for complete search history.

(56) References Cited

U.S. PATENT DOCUMENTS

| | | |
|---|---|---|
| 3,963,151 A | 6/1976 | North |
| 5,681,529 A | 10/1997 | Taguchi et al. |
| 5,725,831 A | 3/1998 | Reichler et al. |
| 5,750,338 A | 5/1998 | Collins et al. |
| 5,783,148 A | 7/1998 | Cottingham et al. |
| 5,824,478 A | 10/1998 | Muller |
| 5,853,667 A | 12/1998 | Seaton et al. |
| 6,168,948 B1 | 1/2001 | Anderson et al. |
| 6,331,266 B1 | 12/2001 | Powell et al. |
| 6,368,871 B1 | 4/2002 | Christel et al. |
| 6,374,684 B1 | 4/2002 | Dority |
| 6,374,685 B1 | 4/2002 | Daly |
| 6,431,476 B1 | 8/2002 | Taylor et al. |
| 6,440,725 B1 | 8/2002 | Pourahmadi et al. |
| 6,664,104 B2 | 12/2003 | Pourahmadi et al. |
| 6,692,700 B2 | 2/2004 | Handique |
| 6,852,287 B2 | 2/2005 | Ganesan |
| 6,860,993 B2 | 3/2005 | Effenhauser et al. |
| 6,872,315 B2 | 3/2005 | Effenhauser et al. |
| 6,878,540 B2 | 4/2005 | Pourahmadi et al. |
| 6,893,879 B2 | 5/2005 | Petersen et al. |
| 6,899,838 B2 | 5/2005 | Lastovich |
| 6,987,018 B2 | 1/2006 | Taylor et al. |
| 7,052,268 B2 | 5/2006 | Powell et al. |
| 7,135,144 B2 | 11/2006 | Christel et al. |
| 7,192,557 B2 | 3/2007 | Wu et al. |
| 7,270,786 B2 | 9/2007 | Parunak et al. |
| 7,323,140 B2 | 1/2008 | Handique et al. |
| 7,332,130 B2 | 2/2008 | Handique |
| 7,569,346 B2 | 8/2009 | Petersen et al. |
| 7,674,431 B2 | 3/2010 | Ganesan |
| 7,682,820 B2 | 3/2010 | Bader |
| 7,731,906 B2 | 6/2010 | Handique et al. |
| 7,738,094 B2 | 6/2010 | Goldberg |
| 7,763,209 B2 | 7/2010 | Haley |
| 7,767,447 B2 | 8/2010 | Breidenthal et al. |
| 7,820,030 B2 | 10/2010 | Althaus et al. |
| 7,906,758 B2 | 3/2011 | Stults et al. |
| 7,914,994 B2 | 3/2011 | Petersen et al. |
| 7,935,537 B2 | 5/2011 | Haley |
| 7,955,798 B2 | 6/2011 | Mauritz |
| 7,955,864 B2 | 6/2011 | Cox et al. |
| 7,964,413 B2 | 6/2011 | Macioszek et al. |
| 7,987,022 B2 | 7/2011 | Handique et al. |
| 7,995,798 B2 | 8/2011 | Krupnik et al. |
| 7,998,708 B2 | 8/2011 | Handique et al. |
| 8,003,329 B2 | 8/2011 | Macevicz |
| 8,008,066 B2 | 8/2011 | Lair et al. |
| 8,043,581 B2 | 10/2011 | Ganesan |
| 8,048,375 B2 | 11/2011 | Breidenthal et al. |
| 8,048,386 B2 | 11/2011 | Dority et al. |
| 8,052,929 B2 | 11/2011 | Breidenthal et al. |
| 8,088,616 B2 | 1/2012 | Handique |
| 8,105,477 B2 | 1/2012 | Althaus et al. |
| 8,105,783 B2 | 1/2012 | Handique |
| 8,110,158 B2 | 2/2012 | Handique |
| 8,133,671 B2 | 3/2012 | Williams et al. |
| 8,168,134 B2 | 5/2012 | Lehto |
| 8,182,763 B2 | 5/2012 | Duffy et al. |
| 8,183,359 B2 | 5/2012 | Becker et al. |
| 8,187,557 B2 | 5/2012 | Van et al. |
| 8,247,176 B2 | 8/2012 | Petersen et al. |
| 8,248,597 B2 | 8/2012 | Goldberg |

(56) References Cited

U.S. PATENT DOCUMENTS

| | | |
|---|---|---|
| 8,268,245 B2 | 9/2012 | Wahl |
| 8,268,603 B2 | 9/2012 | Taylor et al. |
| 8,273,308 B2 | 9/2012 | Handique et al. |
| 8,287,820 B2 | 10/2012 | Williams et al. |
| 8,288,520 B2 | 10/2012 | Eder et al. |
| 8,323,584 B2 | 12/2012 | Ganesan |
| 8,323,900 B2 | 12/2012 | Handique et al. |
| 8,324,372 B2 | 12/2012 | Brahmasandra et al. |
| 8,349,564 B2 | 1/2013 | Macioszek et al. |
| 8,394,336 B2 | 3/2013 | Curcio |
| 8,404,198 B2 | 3/2013 | Amshey et al. |
| 8,415,103 B2 | 4/2013 | Handique |
| 8,420,015 B2 | 4/2013 | Ganesan et al. |
| 8,431,413 B2 | 4/2013 | Dority et al. |
| 8,440,149 B2 | 5/2013 | Handique |
| 8,470,586 B2 | 6/2013 | Wu et al. |
| 8,470,588 B2 | 6/2013 | Boehm et al. |
| 8,473,104 B2 | 6/2013 | Handique et al. |
| 8,480,976 B2 | 7/2013 | Breidenthal et al. |
| 8,491,178 B2 | 7/2013 | Breidenthal et al. |
| 8,501,461 B2 | 8/2013 | Knight et al. |
| 8,506,908 B2 | 8/2013 | Benn et al. |
| 8,640,555 B2 | 2/2014 | Zenhausern et al. |
| 8,709,787 B2 | 4/2014 | Handique |
| 9,101,930 B2 | 8/2015 | Williams et al. |
| 9,382,532 B2 | 7/2016 | Brahmasandra et al. |
| 2002/0039783 A1 | 4/2002 | McMillan et al. |
| 2002/0160518 A1 | 10/2002 | Hayenga et al. |
| 2003/0170686 A1 | 9/2003 | Hoet et al. |
| 2004/0018611 A1 | 1/2004 | Ward et al. |
| 2004/0138154 A1 | 7/2004 | Yu et al. |
| 2005/0180891 A1 | 8/2005 | Webster et al. |
| 2005/0205199 A1 | 9/2005 | Green |
| 2005/0221529 A1 | 10/2005 | Bang et al. |
| 2005/0233370 A1 | 10/2005 | Ammann et al. |
| 2005/0250199 A1* | 11/2005 | Anderson ............ B01F 11/0071 435/287.2 |
| 2005/0272169 A1 | 12/2005 | Griffin et al. |
| 2006/0068204 A1 | 3/2006 | Rasmussen et al. |
| 2006/0166233 A1 | 7/2006 | Wu et al. |
| 2006/0182300 A1 | 8/2006 | Schwartz |
| 2006/0182842 A1 | 8/2006 | Pruden et al. |
| 2007/0148174 A1 | 6/2007 | Kudlicki et al. |
| 2007/0184463 A1 | 8/2007 | Molho et al. |
| 2007/0190662 A1 | 8/2007 | Baetzold et al. |
| 2007/0196912 A1 | 8/2007 | Facer et al. |
| 2007/0292941 A1 | 12/2007 | Handique et al. |
| 2008/0057572 A1 | 3/2008 | Petersen et al. |
| 2008/0146896 A1 | 6/2008 | Rabinowitz et al. |
| 2008/0193384 A1 | 8/2008 | Willard et al. |
| 2008/0200343 A1 | 8/2008 | Clemens et al. |
| 2008/0241569 A1 | 10/2008 | Qin et al. |
| 2008/0275409 A1 | 11/2008 | Kane et al. |
| 2008/0280285 A1 | 11/2008 | Chen et al. |
| 2009/0130719 A1 | 5/2009 | Handique |
| 2009/0131650 A1 | 5/2009 | Brahmasandra et al. |
| 2009/0215125 A1 | 8/2009 | Reed et al. |
| 2009/0275014 A1* | 11/2009 | Maltezos ............ B01L 3/50851 435/5 |
| 2010/0009351 A1 | 1/2010 | Brahmasandra et al. |
| 2010/0009375 A1 | 1/2010 | Sherman et al. |
| 2010/0029544 A1 | 2/2010 | Cheng et al. |
| 2010/0075311 A1 | 3/2010 | Barrault et al. |
| 2010/0165784 A1 | 7/2010 | Jovanovich et al. |
| 2010/0300563 A1 | 12/2010 | Ramunas et al. |
| 2010/0303687 A1 | 12/2010 | Blaga et al. |
| 2010/0310423 A1 | 12/2010 | Nieuwenhuis |
| 2010/0323919 A1 | 12/2010 | Chen et al. |
| 2011/0003281 A1 | 1/2011 | Woudenberg et al. |
| 2011/0043237 A1* | 2/2011 | Kiyokawa ............ G01R 31/2893 324/756.03 |
| 2011/0053289 A1* | 3/2011 | Lowe .................... B01L 3/5027 436/501 |
| 2011/0071031 A1 | 3/2011 | Khripin et al. |
| 2011/0201099 A1 | 8/2011 | Anderson et al. |
| 2011/0318840 A1 | 12/2011 | Ziglioli Federico et al. |
| 2012/0046203 A1 | 2/2012 | Walsh et al. |
| 2012/0245218 A1 | 9/2012 | Fukushima et al. |
| 2012/0245337 A1 | 9/2012 | Fabis et al. |
| 2013/0210015 A1 | 8/2013 | Williams et al. |
| 2013/0210127 A1 | 8/2013 | Williams et al. |

FOREIGN PATENT DOCUMENTS

| | | | |
|---|---|---|---|
| CN | 101842690 B | 6/2013 | |
| EP | 0707077 A2 | 4/1996 | |
| GB | 2125007 A * | 2/1984 | ............... B66F 3/12 |
| WO | 2002048164 A2 | 6/2002 | |
| WO | 2004003200 A1 | 1/2004 | |
| WO | 2007064635 A1 | 6/2007 | |
| WO | 2008097342 A2 | 8/2008 | |
| WO | 2008115626 A2 | 9/2008 | |
| WO | 2009022994 | 4/2009 | |
| WO | 2010072821 A1 | 7/2010 | |
| WO | 2010121315 A1 | 10/2010 | |
| WO | 2009038536 | 12/2012 | |

* cited by examiner

CLOSED      OPEN

SYSTEM AND METHOD FOR PROCESSING AND DETECTING NUCLEIC ACIDS

CROSS-REFERENCE TO RELATED APPLICATION

This application is a continuation of co-pending U.S. patent application Ser. No. 14/704,215, filed 5 May 2015, which is a continuation of co-pending U.S. patent application Ser. No. 13/766,359, filed 13 Feb. 2013, which claims the benefit of U.S. Provisional Application Ser. No. 61/667,606, filed on 3 Jul. 2012, and U.S. Provisional Application Ser. No. 61/598,240, filed on 13 Feb. 2012, which are incorporated herein in their entirety by this reference. This application is also a continuation of co-pending U.S. application Ser. No. 13/765,996, filed 13 Feb. 2013, which is incorporated herein in its entirety by this reference.

TECHNICAL FIELD

This invention relates generally to the molecular diagnostics field, and more specifically to an improved system and method for processing and detecting nucleic acids.

BACKGROUND

Molecular diagnostics is a clinical laboratory discipline that has developed rapidly during the last 25 years. It originated from basic biochemistry and molecular biology research procedures, but now has become an independent discipline focused on routine analysis of nucleic acids (NA), including deoxyribonucleic acid (DNA) and ribonucleic acid (RNA) for diagnostic use in healthcare and other fields involving analysis of nucleic acids. Molecular diagnostic analysis of biological samples can include the detection of one or more nucleic acid materials present in the specimen. The particular analysis performed may be qualitative and/or quantitative. Methods of analysis typically involve isolation, purification, and amplification of nucleic acid materials, and polymerase chain reaction (PCR) is a common technique used to amplify nucleic acids. Often, a nucleic acid sample to be analyzed is obtained in insufficient quantity, quality, and/or purity, hindering a robust implementation of a diagnostic technique. Current sample processing methods and molecular diagnostic techniques are often labor/time intensive, low throughput, and expensive, and systems of analysis are insufficient. Furthermore, methods of isolation, processing, and amplification are specific to certain sample matrices and/or nucleic acid types and not applicable across common sample and nucleic acid types.

Due to these and other deficiencies of current molecular diagnostic systems and methods, there is thus a need for and improved system and method for processing and detecting nucleic acids. This invention provides such a system and method.

DESCRIPTION OF THE PREFERRED EMBODIMENTS

The following description of preferred embodiments of the invention is not intended to limit the invention to these preferred embodiments, but rather to enable any person skilled in the art to make and use this invention.

1. System for Processing and Detecting Nucleic Acids

Figure 1A:
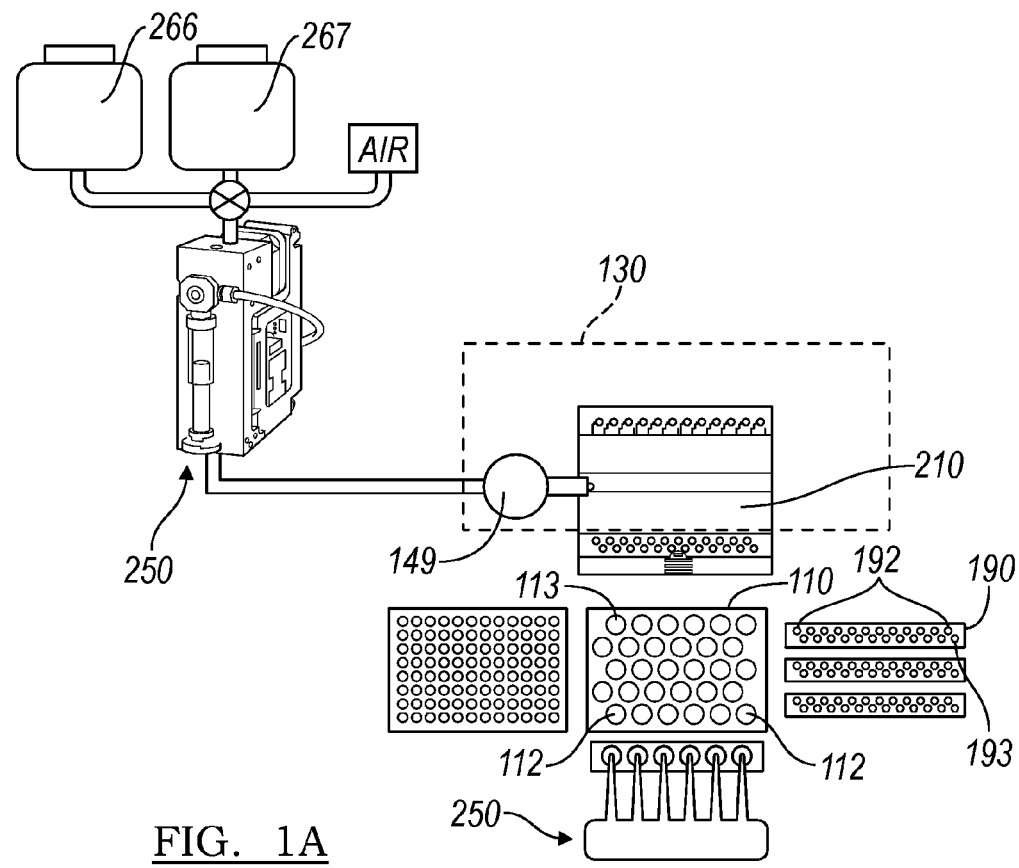
FIGS. 1A-1B depict an embodiment of a system for processing and detecting nucleic acids.
Figure 1B:
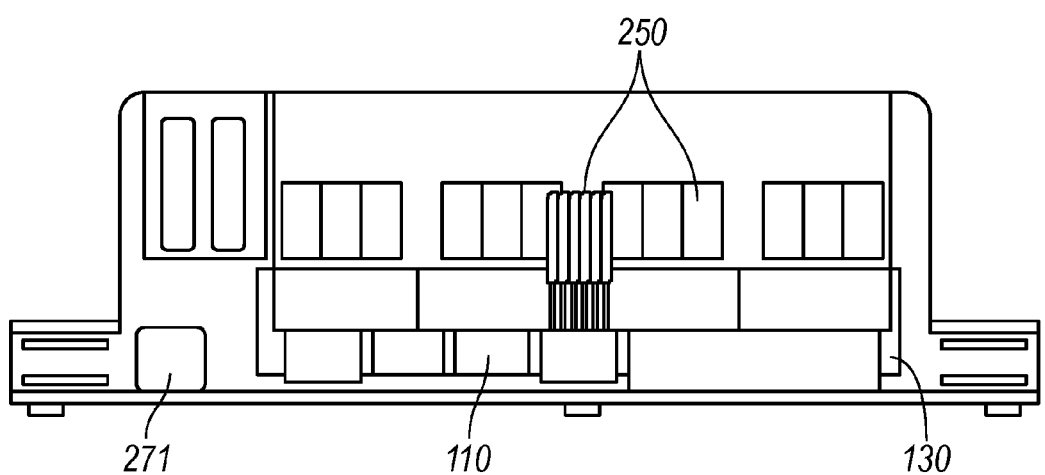
Figure 2A:
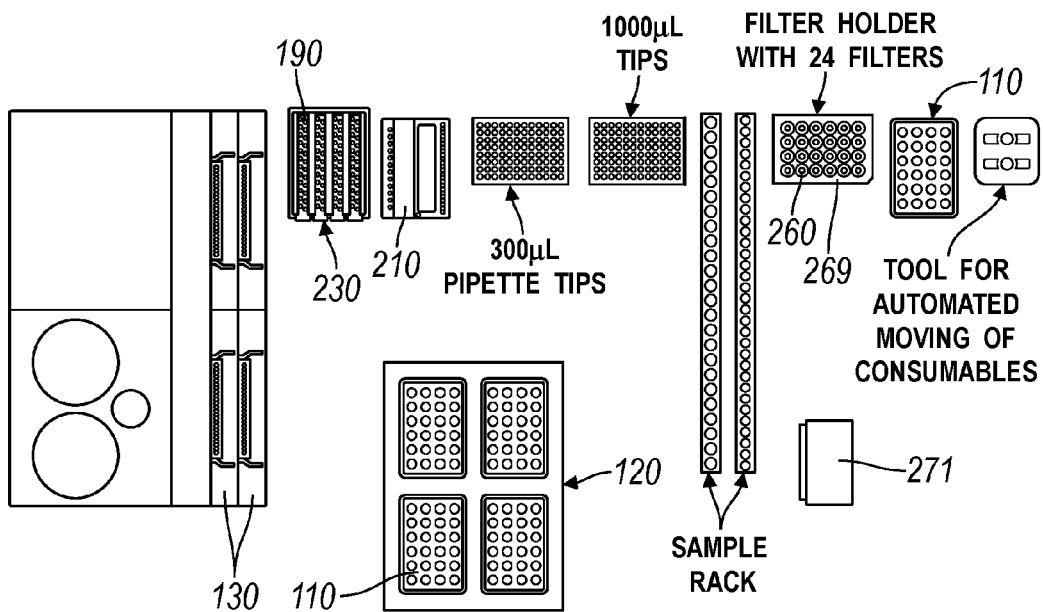
FIGS. 2A-2B depict an embodiment of elements, and a top view of an embodiment of a system worktable, respectively, of an embodiment of a system for processing and detecting nucleic acids.
Figure 2B:
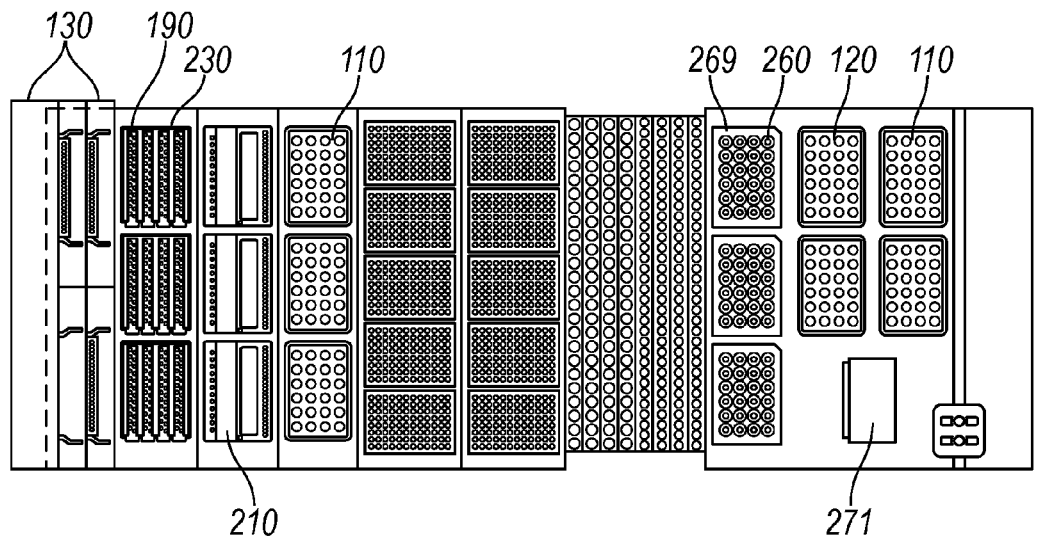
Figure 7A:
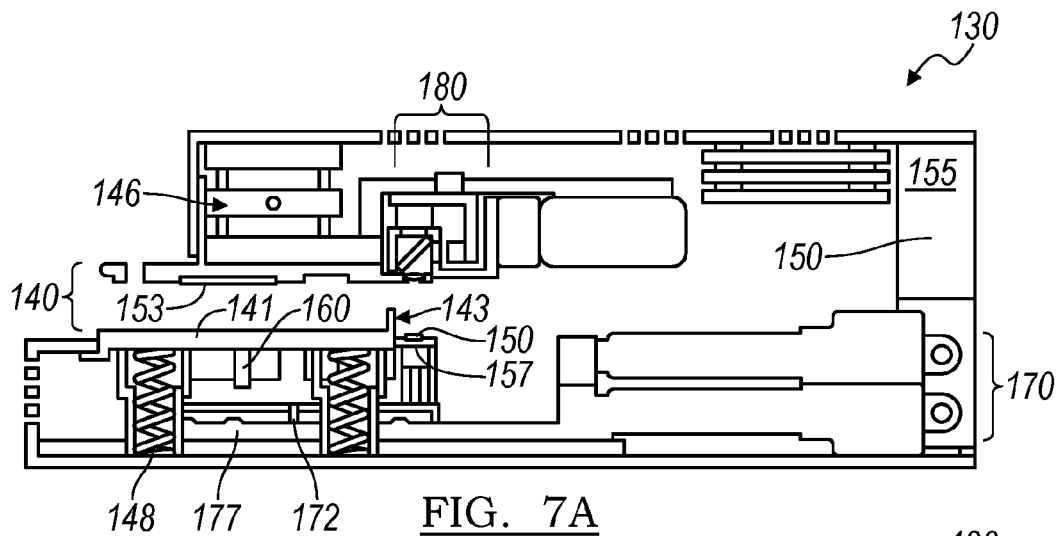
FIGS. 7A-7E depict a sequence of operations performed by elements of an embodiment of a molecular diagnostic module.

As shown in FIGS. 1A-1B and 7A, an embodiment of a system 100 for processing and detecting nucleic acids comprises: a capture plate 110 configured to facilitate binding of nucleic acids within a biological sample to a set of magnetic beads 119; a molecular diagnostic module 130 comprising a microfluidic cartridge receiving module 140, heating and cooling subsystem 150, a magnet 160, a valve actuation subsystem 170, an optical subsystem 180; and an assay strip 190 configured to facilitate mixing of molecular diagnostic reagents with a nucleic acid volume. Other embodiments of the system 100 may further comprise at least one of a capture plate module 120 configured to support the capture plate 110; a filter 200 and filter holder 205 to facilitate sample preparation; a microfluidic cartridge 210 configured to facilitate sample processing; an assay strip holder 230; an assay strip carrier 240; a liquid handling system 250 configured to facilitate gas and fluid delivery to different elements of the system 100; a processor configured to analyze data resulting from a run of the system 100; and a user interface configured to allow a user to interact with the system 100. The system 100 thus functions to receive biological samples containing nucleic acids (i.e., impure nucleic acid samples), separate nucleic acids from the biological samples, and analyze nucleic acid samples according to at least one molecular diagnostic protocol (e.g., PCR). Preferably, the system 100 is a walkaway system by which a user loads a set of biological samples containing nucleic acids, and receives a set of data resulting from a molecular diagnostic protocol without any further sample manipulation by the user. Alternatively, the system 100 facilitates aspects of sample preparation for a molecular diagnostic protocol, with some sample manipulation performed by the user.

In one example workflow of the system 100, a liquid handling system 250 aspirates a set of biological samples containing nucleic acids (i.e., impure nucleic acid samples), and dispenses the set of biological samples into a capture plate 110 to be lysed and combined with magnetic beads (containing a proprietary affinity coating to bind the nucleic acids to the magnetic beads) by a capture plate module 120. The liquid handling system 250 then aspirates substantially all of each sample of the set of lysed biological samples combined with magnetic beads (i.e., set of magnetic bead-samples) from the capture plate 110, and dispenses the set of magnetic bead-samples into a microfluidic cartridge 210, aligned within a cartridge receiving module 140 of a molecular diagnostic module 130, and configured to be manipulated by the molecular diagnostic module 130. A heating and cooling subsystem 150, a magnet 160, and a valve actuation subsystem 170 of the molecular diagnostic module 130 then facilitate separation of a set of nucleic acids from the magnetic bead-samples, as the liquid handling system 250 dispenses wash solutions, release solutions, and/or air at appropriate stages. The liquid handling system 250 then aspirates the set of nucleic acids from the microfluidic cartridge 210 contained within the molecular diagnostic module 130, combines the set of nucleic acids with a set of molecular diagnostic reagents using an assay strip 190, and dispenses the set of nucleic acids combined with the set of molecular diagnostic reagents (i.e., set of nucleic acid-reagent mixtures) into the microfluidic cartridge 210 within the molecular diagnostic module 130. The detection chamber heaters 157, optical subsystem 180 and valve actuation subsystem 170 of the molecular diagnostic module 130 then facilitate analysis of the set of nucleic acid-reagent mixtures by a processor configured to display information on a user interface.

As stated, the above workflow is just one example workflow of the system 100, and other workflows of the system 100 and methods of processing and detecting nucleic acid samples are further described in Section 2 below. A detailed description of elements of an embodiment of the system 100 are described in sections 1.1-1.6 below.

1.1 System—Capture Plate and Capture Plate Module

Figure 3A:
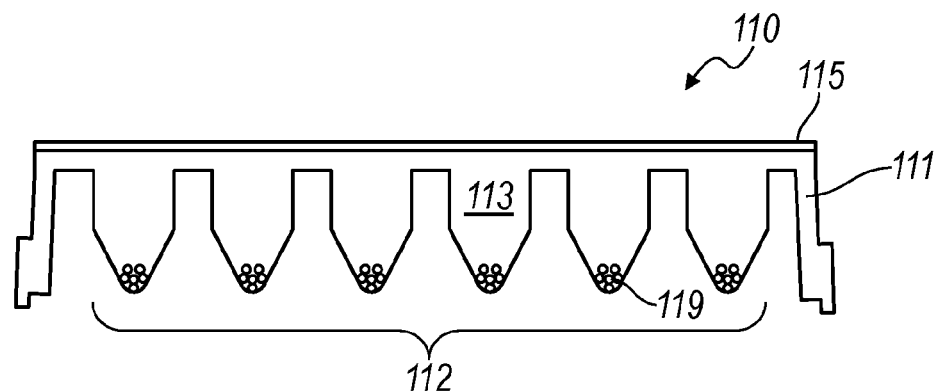
FIGS. 3A-3B depict an embodiment of a capture plate for combining a sample with magnetic beads.
Figure 3B:
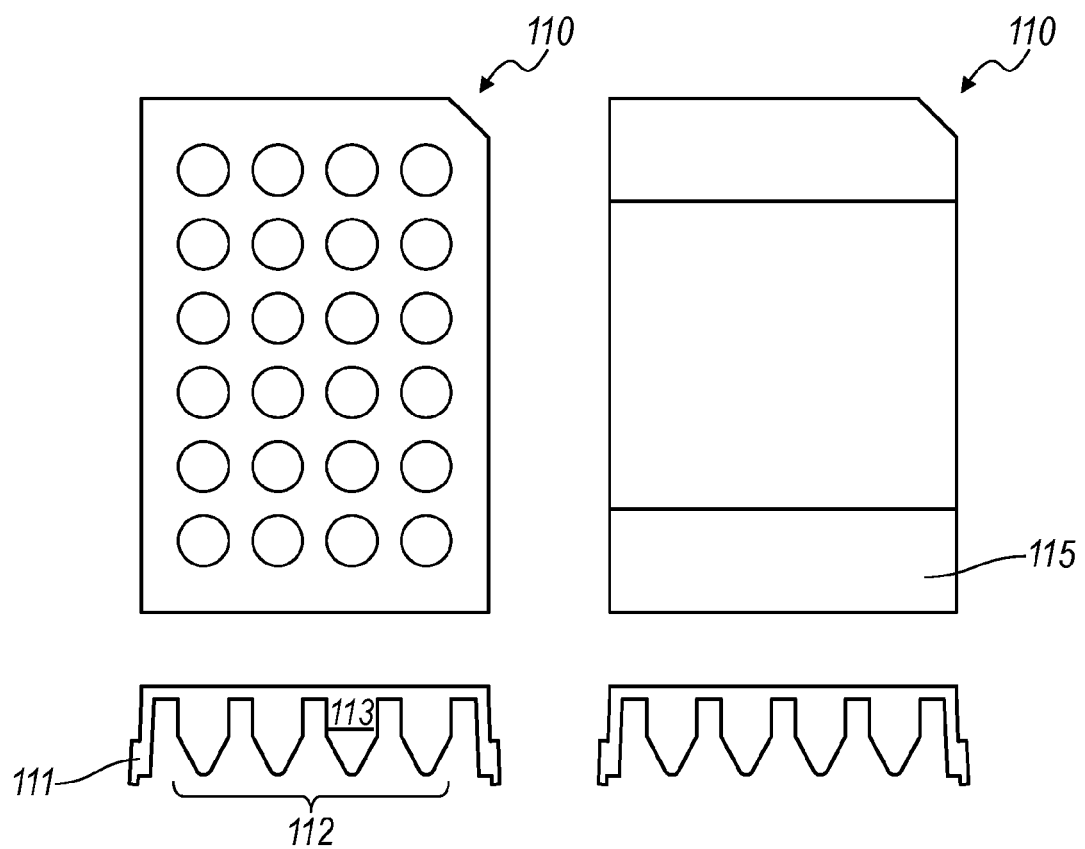

As shown in FIGS. 3A and 3B, the capture plate 110 comprises a capture plate substrate 111 comprising a set of wells 112 and a puncturable foil seal 115, and functions to facilitate binding of nucleic acids within a biological sample to a set of magnetic beads 119. Preferably, the entire capture plate 110 is configured to be a consumable (i.e., disposable), such that each well of the capture plate 110 can only be used once yet the remaining unused wells can be used during additional runs of the system 100. Alternatively, at least a portion of the capture plate 110 is configured to be reusable, such that additional mixing or reagent additions can be performed and portions of the capture plate 110 may be used for multiple runs of the system 100. In one variation of the capture plate 110, the capture plate substrate 111 is reusable, while the puncturable foil seal 115 is disposable and replaced after each run of the system 100.

The capture plate substrate 111 is configured such that the capture plate 110 is capable of resting on a flat surface, can be stacked with another capture plate 110, and also can be manipulated with industry standard instrument components for handling of microtiter plates. The capture plate substrate also functions to define the set of wells 112 and to couple to the puncturable foil seal 115. The capture plate substrate 111 is preferably composed of a PCR-compatible polymer that can be heat processed to couple to the puncturable foil seal 115, but can alternatively be composed of any appropriate material that can contain a fluid and be bonded to the puncturable foil seal 115.

The set of wells 112 of the capture plate substrate 111 function to receive at least one biological sample which contain or are suspected of potentially containing nucleic acids, and to facilitate combination of the biological sample with a set of magnetic beads 119. Preferably, the wells 113 are each configured to accommodate not only a biological sample, but also to facilitate mixing of the biological sample with a set of magnetic beads 119 (e.g., using a pipettor, the liquid handling system 250 or other apparatus), which preferably are preloaded in wells 112, or alternatively may be added by an operator. Preferably, the wells are also deeper than they are wide to allow a significant number of wells 112 (e.g. 24) with a clinically relevant sample volumes, and evenly spaced to facilitate aspiration, delivery, and/or mixing of multiple biological samples (e.g., with a multi-tip pipettor). Alternatively, the wells are wider than they are deep to facilitate larger devices for mixing the biological samples with the magnetic beads 119. Each well 113 of the set of wells 112 also preferably has a conically shaped bottom region, as shown in FIG. 3A, to facilitate complete aspiration of a fluid from a well. Alternatively, each well 113 may not have a conically shaped bottom region. Additionally, in the orientation shown in FIG. 3A, the tops of each well 113 in the set of wells 112 preferably form raised edges protruding from the capture plate substrate 111, in order to facilitate sealing of each well 113 by the puncturable foil seal 115. Alternatively, the tops of each well 113 in the set of wells 112 may not form raised edges protruding from the capture plate substrate ill. The magnetic beads are preferably polymer beads, precoupled with a ligand for binding to a nucleic acid, and comprising a superparagmagnetic component. Additionally, the magnetic beads may be treated to be positively charged. However, the magnetic beads may alternatively be any appropriate magnetic beads (e.g. magnetic, parmagnetic, or superparamagnetic) configured to facilitate biomagnetic separation.

Each quantity of magnetic beads 119 may be accompanied by lysing reagents (e.g. proteinase K) and a sample process control comprising nucleic acid sequences for DNA and RNA, which function to lyse biological samples and to provide a mechanism by which sample process controls may be later detected to verify processing fidelity and assay accuracy. The sample process control comprising nucleic acid sequences for DNA and RNA allows one version of the capture plate to facilitate assays involving DNA and RNA detection. Preferably, the quantity of magnetic beads 119, lysing reagents, and sample process controls is dried within each well to improve shelf life; however, the quantity of magnetic beads 119, lysing reagents, and sample process controls may alternatively be in liquid form.

The puncturable foil seal 115 functions to isolate each well 113 of the set of wells 112, prevent contamination of the contents of each of the set of wells 112, protect the magnetic beads 119 and other reagents stored in wells 112 from degradation, and provide information identifying the capture plate 110. The puncturable foil seal 115 preferably seals each well 113 of the capture plate 110, and is configured to be punctured by an external element (e.g., by a pipette tip), such that each well is sealed prior to being punctured. In one variation, the puncturable foil seal 115 also forms a seal around an element that punctures it, and in another variation, the puncturable foil seal 115 does not form a seal around an element that punctures it, in order to prevent airlock. The puncturable foil seal 115 is also preferably labeled with identifying information including at least one of manufacturer information, capture plate contents, the lot of the contents, an expiry date, and a unique electronic tag (e.g., barcode or QR code) providing more information. Preferably, the puncturable foil seal 115 does not extend beyond the footprint of the capture plate 110, but alternatively, the puncturable foil seal 115 may be any appropriate size and/or include protruding features (e.g., tabs) that facilitate handling of the capture plate.

In one variation, the capture plate 110 may be prepackaged at least with magnetic beads 119, such that each well 113 in the set of wells 112 is prepackaged with a set of magnetic beads 119 defined by a specific quantity or concentration of magnetic beads. The set of wells 112 may then be sealed by the puncturable foil seal 115, which is configured to be punctured by an external element that delivers volumes of biological samples to be mixed with the magnetic beads 119. In another variation, the capture plate 110 may not be prepackaged with magnetic beads 119, but the wells 113 of the capture plate may still be sealed with a puncturable foil seal 115. In this variation, the puncturable foil seal 115 is configured to be punctured by at least one external element, for co-delivery of biological samples and magnetic beads intended to be combined.

Figure 5A:
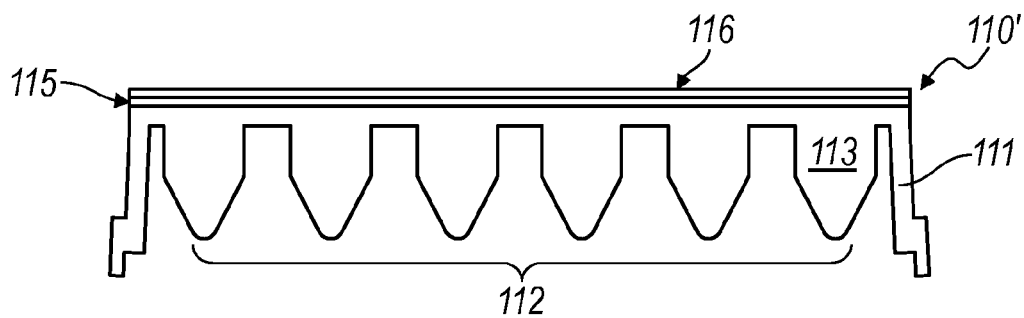
FIGS. 5A-5B depict an alternative embodiment of a capture plate.
Figure 5B:
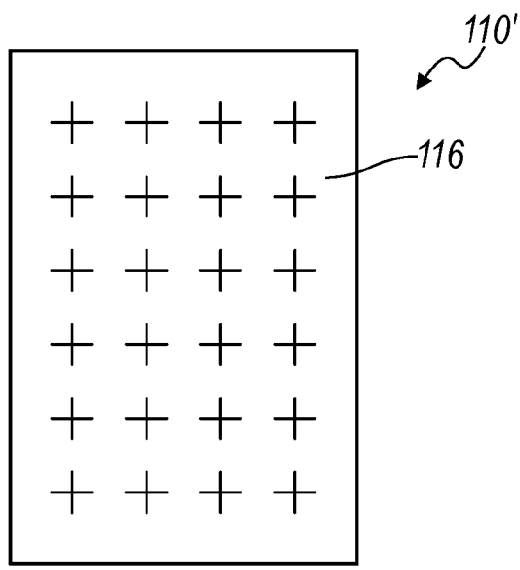

A variation of the capture plate 110' may further comprise a slotted rubber membrane 116, as shown in FIGS. 5A and 5B, configured to provide access through the puncturable foil seal 115 to the set of wells 112. The slotted rubber membrane 116 thus functions to prevent or reduce splashing, evaporation, and/or aerosolization of contents of the set of wells 112. Preferably, the slotted rubber membrane 116 comprises slots that are self-sealing and centered over wells of the set of wells 112, and further does not extend beyond the footprint of the capture plate 110. Alternatively, the slots of the slotted rubber membrane 116 may not be self-sealing, and/or the slotted rubber membrane 116 may be any appropriate size and comprise features that extend beyond the footprint of the capture plate 110.

In a specific example, the capture plate 110 comprises 24 wells 113 with an 18 mm center-to-center pitch, each well having a volumetric capacity of 2 mL, and is compliant with Society for Laboratory Automation and Screening (SLAS) standards. Each well 113 of the capture plate 110 in the specific example is also prepackaged with a specified quantity of magnetic beads 119, and comprises a protruding top edge that is heat sealed to a puncturable foil seal. In addition, each well 113 also contains other reagents beneficial for processing and monitoring the sample, including proteinase K and one or more specific nucleic acid stands designed to serve as a process control. The specific example of the capture plate 110 can thus combine two groups of 12 biological samples with magnetic beads. The capture plate 110 in the specific example is produced by injection molding, has a footprint of 127.75 mm×85.5 mm, and is composed of a PCR-compatible polypropylene based polymer with a high vapor barrier.

Figure 4:
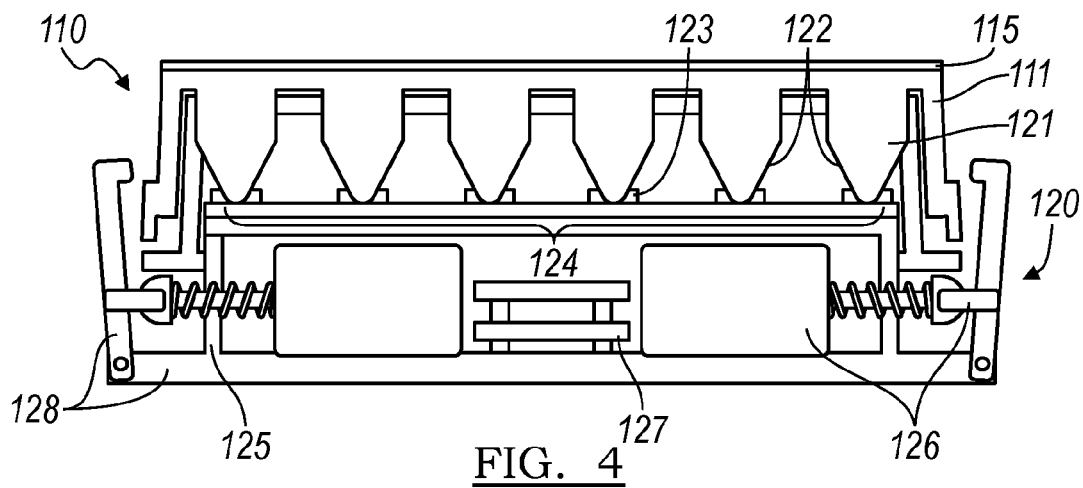
FIG. 4 depicts an embodiment of a capture plate module to facilitate lysis of a biological sample and combination of the biological sample with magnetic beads.

An embodiment of the system 100 may further comprise a capture plate module 120, as shown in FIG. 4, which functions to receive, support, and heat a capture plate 110. The capture plate module 120 preferably comprises a thermally conducting substrate 121 configured to cradle a capture plate 110, a capture plate heater 123, a capture plate receiving module 125, and a capture plate electronics module 127. Preferably, the capture plate module 120 functions to facilitate lysis of a biological sample deposited into a well 113 of the capture plate, and to facilitate binding of nucleic acids (i.e., within a lysed biological sample) to a quantity of magnetic beads 119 within a well 113 of the capture plate 110. In a specific example, the capture plate module 120 has dimensions of 108 mm×156 mm×45 mm and is configured to rest on a flat surface.

The thermally conducting substrate 121 is configured to cradle and support the capture plate 110, and functions to conduct heat to the set of wells 112 of the capture plate 110. Preferably, the thermally conducting substrate 121 is also configured to reversibly couple to the capture plate 110, and comprises a set of indentations 122 that encircle each well 113 in the set of wells 112. In one variation, the indentations 122 completely conform to the external surface of each well 113 of the capture plate 110, but in another variation, the indentations 122 may encircle a portion of each well 113 of the capture plate 110. Additionally, the indentations 122 are preferably thermally conducting in order to conduct heat to the set of wells 112, and portions of the thermally conducting substrate 121 aside from the indentations 122 are composed of non-conducting, rigid material. Alternatively, the entire thermally conducting substrate 121 may be composed of a material that is thermally conducting.

The capture plate heater 123 is preferably coupled to the thermally conducting substrate 121, and functions to transfer heat, through the thermally conducting substrate 121, to a well 113 of the capture plate 110. The capture plate heater 123 preferably conforms to at least a portion of an indentation 122 of the thermally conducting substrate 121, to facilitate heat transfer through the indentation 122 to an individual well 113 of the capture plate 110. In this variation, the capture plate heater 123 is one of a set of capture plate heaters 124, wherein each capture plate heater 123 in the set of capture plate heaters 124 transfers heat to an individual well 113 of the set of wells 112 of the capture plate 110. Alternatively, the capture plate heater 123 may conform to portions of multiple indentations 122 of the thermally conducting substrate 121, such that the capture plate heater 123 is configured to transfer heat to multiple wells 113 of the capture plate 110. Preferably, the capture plate heater 123 is a resistance heater, but alternatively, the capture plate heater 123 may be a Peltier or any appropriate heater configured to transfer heat to the capture plate 110. The capture plate heater 123 may also further couple to a heat sink.

The capture plate receiving module 125 comprises a capture plate actuation system 126 that functions to couple the capture plate module 120 to a capture plate 110. As shown in FIG. 4, the capture plate actuation system 126 comprises a structural support with hinged grips 128 and at least one capture plate module actuator 129. The capture plate module actuator 129 is preferably a push-type solenoid with a spring return, but may alternatively be any appropriate linear actuator, such as a hydraulic actuator. The structural support with hinged grips 128 preferably couples to the capture plate heater 123 and houses the capture plate module actuator 129, such that, in a first configuration, actuation of the capture plate module actuator 129 outwardly displaces the hinged grips (allowing the capture plate module 120 to receive a capture plate 110), and in a second configuration, actuation of the capture plate module actuator 129 inwardly displaces the hinged grips (allowing the capture plate module 120 to couple to the capture plate 110). The structural support with hinged grips 128 may further comprise a textured and/or high-friction surface configured to grip a capture plate 110, but alternatively may not comprise a textured and/or high-friction surface.

The capture plate electronics module 127 is coupled to the capture plate heater 123 and the capture plate actuation system 126, and functions to enable control of the capture plate heater 123 and the capture plate actuation system 126. Preferably, the capture plate electronics module 127 modulates an output of the capture plate heater 123, in order to controllably heat at least one well 113 of the capture plate 110. Additionally, the capture plate electronics module 127 preferably modulates the capture plate actuation system 126, in order to controllably couple the capture plate module 120 to a capture plate 110. Preferably, the capture plate electronics module 127 is coupled to an external power supply, such that the capture plate module 120 does not include an integrated power supply; however, in alternative embodiments, the capture plate electronics module 127 may be coupled to a power supply integrated with the capture plate module 120.

1.2 System—Molecular Diagnostic Module

Figure 6A:
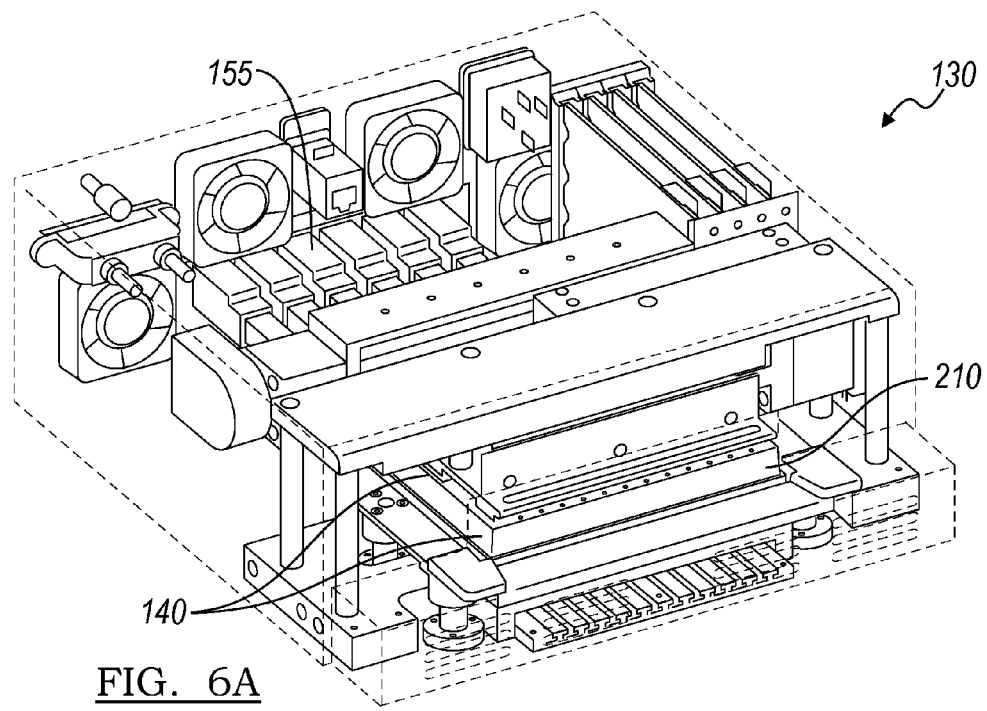
FIGS. 6A-6B depict embodiments of a molecular diagnostic module for processing and detecting nucleic acids.
Figure 6B:
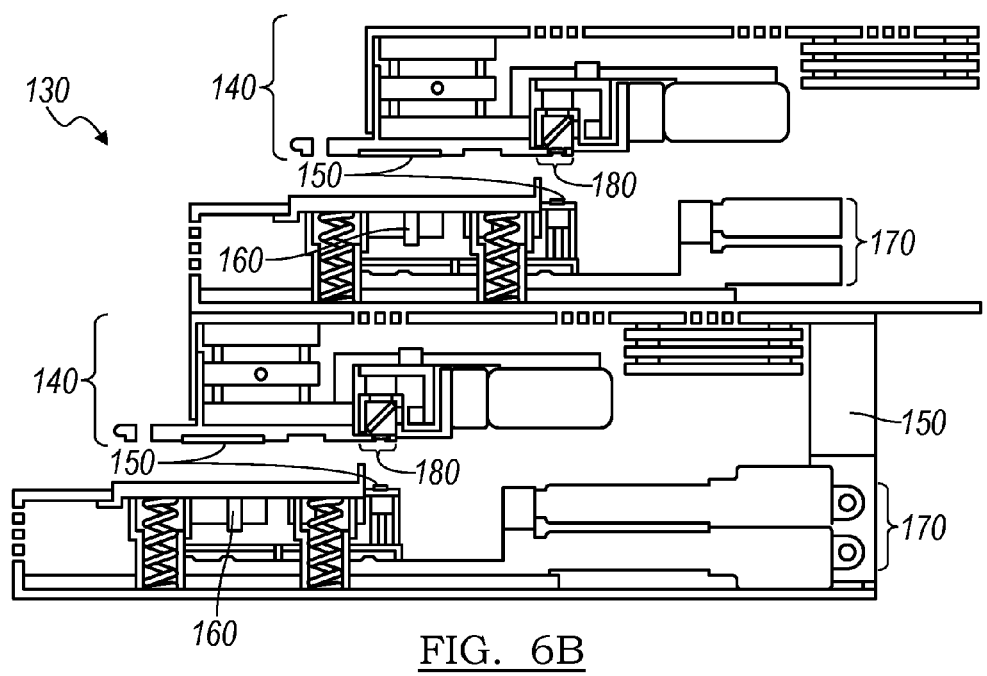

As shown in FIGS. 6A and 6B, an embodiment of the molecular diagnostic module 130 of the system 100 includes a cartridge receiving module 140, a heating and cooling subsystem 150, a magnet 160, a valve actuation subsystem 170, and an optical subsystem 180, and functions to manipulate a microfluidic cartridge 210 for processing of a biological sample containing nucleic acids. The molecular diagnostic module 130 is preferably configured to operate in parallel with at least one other molecular diagnostic module 130, such that multiple microfluidic cartridges 210 containing biological samples may be processed simultaneously. In a first variation, the molecular diagnostic module 130 is configured to be stackable with another molecular diagnostic module 130 in a manner that enables access to a microfluidic cartridge 210 within each molecular diagnostic module 130; an example of the first variation is shown in FIG. 6B, where the molecular diagnostic modules 130 are stacked in a staggered configuration. In the first variation, each molecular diagnostic module 130 may further comprise locking pins or other appropriate mechanisms to couple the stacked molecular diagnostic modules 130 together. In another variation, the molecular diagnostic module 130 may not be configured to stack with another molecular diagnostic module, such that the molecular diagnostic modules 130 are configured to rest side-by-side on the same plane. Elements of an embodiment of the molecular diagnostic module 130 are further described in sections 1.2.1 to 1.2.5 below.

1.2.1 Molecular Diagnostic Module—Cartridge Receiving Module

Figure 7B:
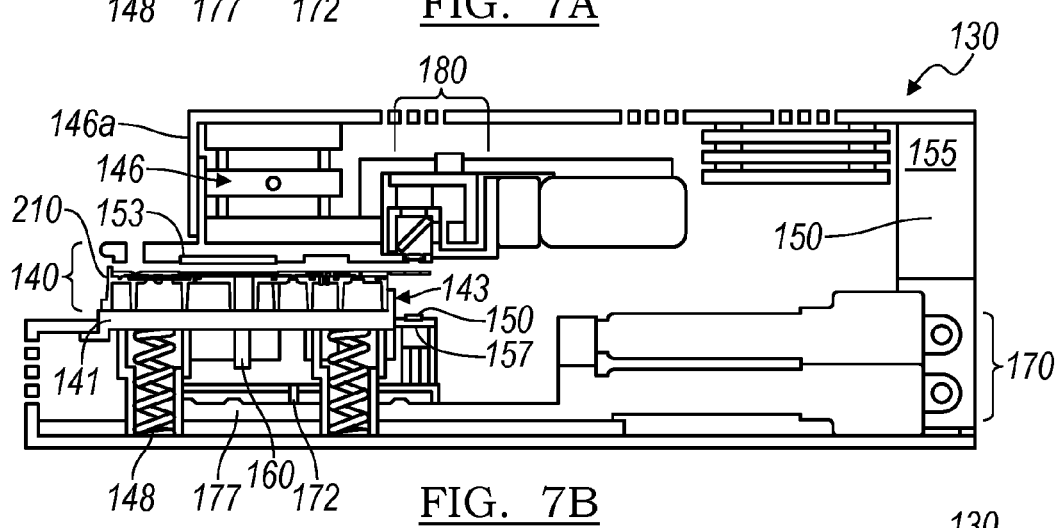
Figure 7C:
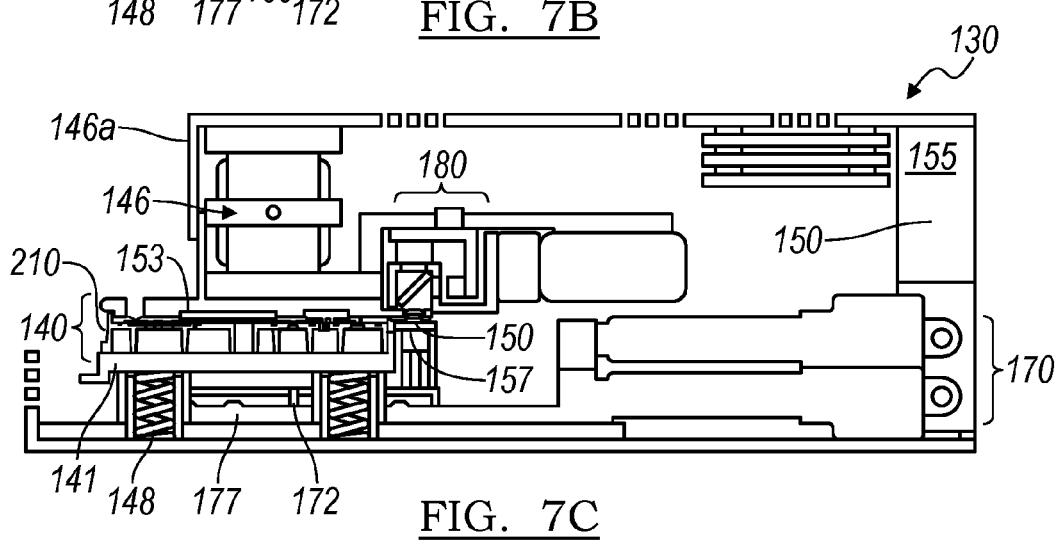
Figure 9A:
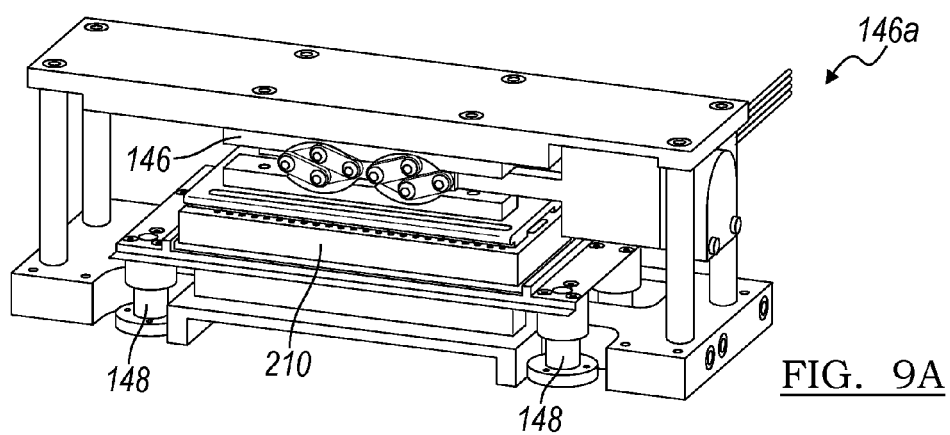
FIGS. 9A-9B depict configurations of a linear actuator of an embodiment of a molecular diagnostic module.

As shown in FIG. 9A, the cartridge receiving module 140 of the molecular diagnostic module 130 comprises a cartridge platform 141 including a cartridge loading guiderail 142, a cartridge stop 143, a magnet receiving slot 144, and a set of valve actuation slots 145; a linear actuator 146 configured to displace a microfluidic cartridge 210 resting on the cartridge platform 141; and a set of springs 148 coupled to the cartridge platform 141. The cartridge receiving module 140 thus functions to receive, align, and compress a microfluidic cartridge 210 for processing of a biological sample according to a molecular diagnostic assay protocol. As shown in FIGS. 7A-7C, the cartridge platform 141 is preferably configured to receive a microfluidic cartridge 210 along a cartridge loading guiderail 142 until it reaches a cartridge stop 143, and be vertically displaced by the linear actuator 146, which places a biasing force against the set of springs 148 coupled to the cartridge platform 141. The magnet receiving slot 144 and the set of valve actuation slots 145 provide access, by a magnet 160 and a valve actuation subsystem 170, to the microfluidic cartridge 210, as the microfluidic cartridge is vertically displaced by the linear actuator 146.

Figure 8:
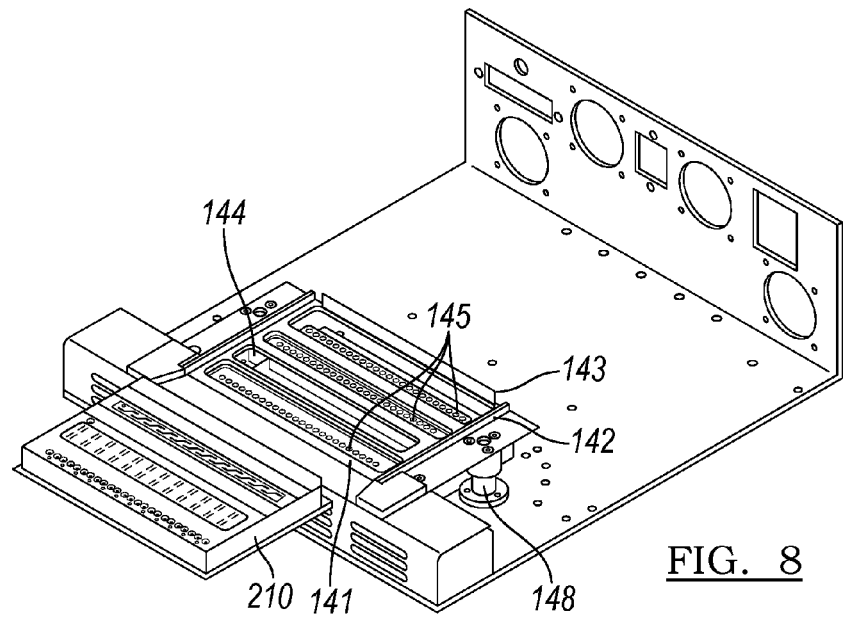
FIG. 8 depicts an embodiment of a microfluidic cartridge and an embodiment of a cartridge platform.

The cartridge platform 141 includes a cartridge loading guiderail 142, a cartridge stop 143, a magnet receiving slot 144, and a set of valve actuation slots 145, and functions to receive and align a microfluidic cartridge 210, while providing access to the microfluidic cartridge 210 by a magnet 160 and a valve actuation subsystem 170. As shown in FIG. 8, an embodiment of the cartridge platform 141 includes a pair of parallel cartridge loading guiderails 142, initiating at a pair of inwardly tapering protrusions configured to guide a microfluidic cartridge toward the pair of parallel cartridge loading guiderails 142, and spanning two short edges of the cartridge platform 141. The embodiment of the cartridge platform 141 also includes a cartridge stop 143 comprising a vertical tab oriented perpendicular to the cartridge loading guiderails 142, and spanning a long edge of the cartridge platform. Preferably, the cartridge loading guiderails 142 and the cartridge stop 143 are configured such that a microfluidic cartridge 210 slides between the cartridge loading guiderails 142 and hits the cartridge stop 143 to signal proper alignment. Alternatively, the cartridge loading guiderails 142 and the cartridge stop 143 may be configured such that a microfluidic cartridge slides over or along the cartridge loading guiderails 142, after which the cartridge stop 143 couples to a portion of the microfluidic cartridge 210 to ensure proper alignment of the microfluidic cartridge. Additional variations of the cartridge loading guiderails 142 and the cartridge stop 143 may be used to enable reception and alignment of a microfluidic cartridge 210 by the molecular diagnostic module 130, and are known by those skilled in the art.

The embodiment of the cartridge platform 141 shown in FIG. 8 also includes a set of valve actuation slots 145, oriented perpendicular to the parallel cartridge loading guiderails 142 and configured to provide access to a valve actuation subsystem 170, and a magnet receiving slot 144 located among the set of valve actuation slots 145. Preferably, the magnet receiving slot 144 and the set of valve actuation slots 145 substantially span a long dimension of the cartridge platform 141, as shown in FIG. 8, and are configured to correspond to locations on a microfluidic cartridge 210 requiring a magnetic field and/or valving to enable processing of a biological sample and nucleic acid detection once the microfluidic cartridge 210 has been aligned within the molecular diagnostic module 130. Thus, alternative configurations of the magnet receiving slot 144 and the set of valve actuation slots 145 may accommodate other cartridges with alternative regions requiring magnetic fields and/or valving to enable other protocols. In one alternative embodiment, the magnet receiving slot 144 and the set of valve actuation slots may comprise one continuous void of the cartridge platform 141, such that the cartridge platform 141 supports a microfluidic cartridge 210 along the periphery of the microfluidic cartridge 210, but forms a continuous void under a majority of the footprint of the microfluidic cartridge 210.

Figure 9B:
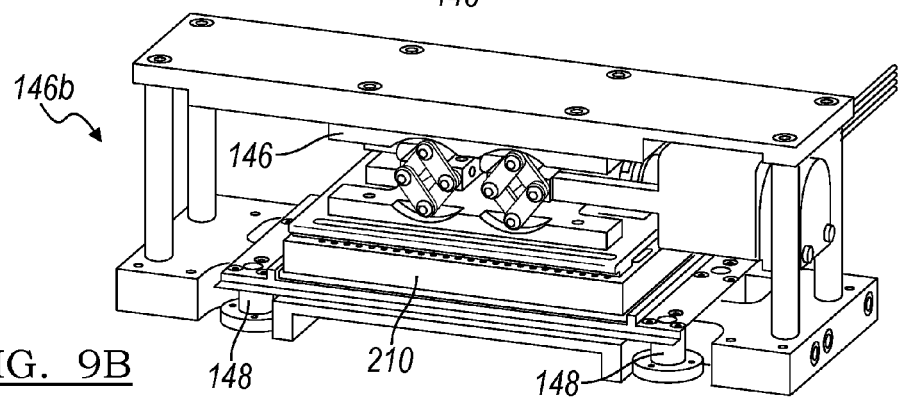
Figure 10A:
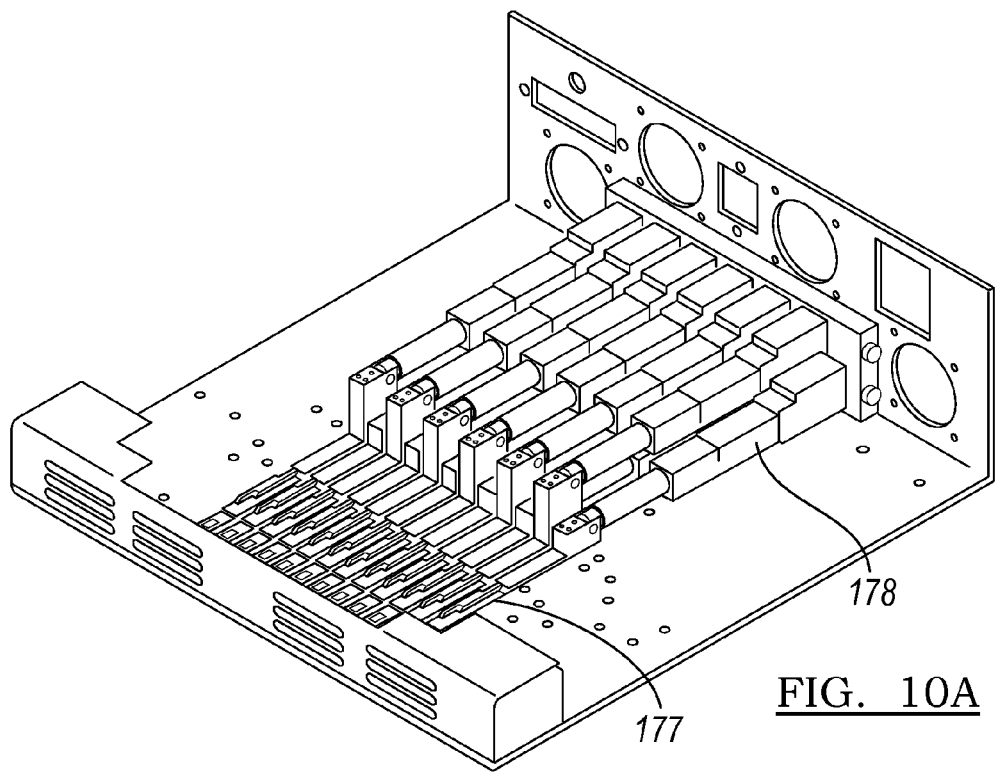
FIGS. 10A-10B depict elements of an embodiment of a valve actuation subsystem of a molecular diagnostic module.
Figure 10B:
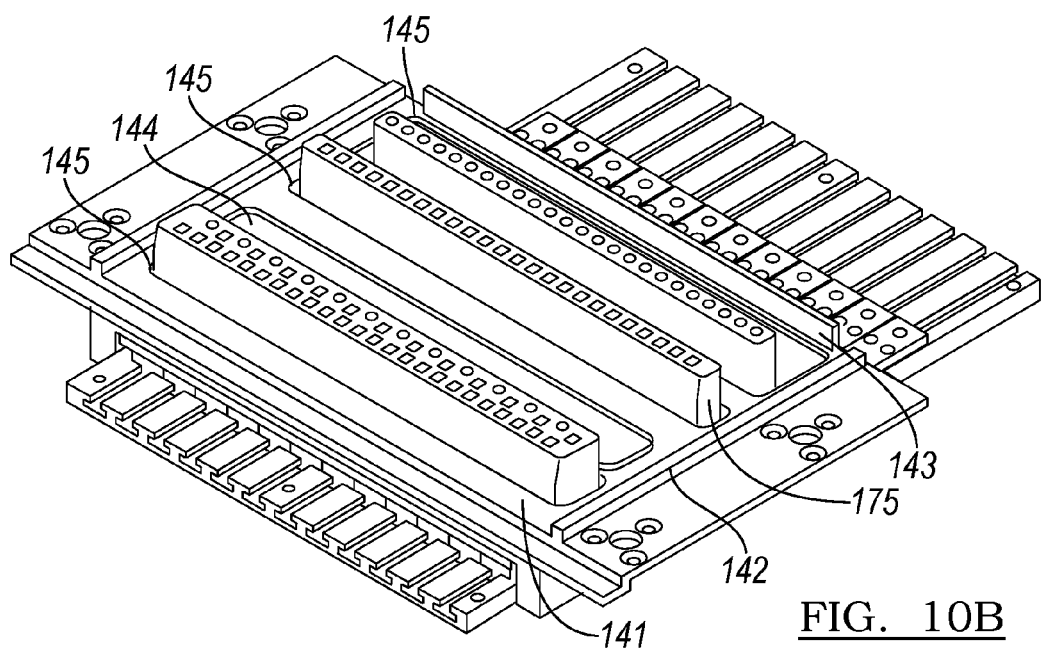

The linear actuator 146 functions to linearly displace a microfluidic cartridge 210 resting on the cartridge platform 141, in order to compress the microfluidic cartridge 210 and position the microfluidic cartridge 210 between a cartridge heater 153 and an optical subsystem 180 on one side of the microfluidic cartridge 210, and a magnet 160 and detection chamber heaters 157 on another side of the microfluidic cartridge 210. The linear actuator 146 also functions to provide a sufficient counterforce to the valve actuation subsystem 170 such that a microfluidic cartridge 210 within the molecular diagnostic module 130 remains properly situation upon manipulation by the valve actuation subsystem 170. The linear actuator 146 further functions to move a nozzle 149 coupled to the liquid handling system 250, in order to couple the liquid handling system 250 to a fluid port 222 of the microfluidic cartridge 210. In the orientation of the molecular diagnostic module 130 shown in FIGS. 7B and 7B, the linear actuator 146 is preferably coupled to a portion of the heating and cooling subsystem 150 a portion of the optical subsystem 180, and the nozzle 149, and vertically displaces the cartridge heater 153, the optical subsystem 180, and the nozzle 149 to position the cartridge heater 153, 180 and the nozzle 149 over the microfluidic cartridge 210. The vertical displacement also allows the microfluidic cartridge 210 to receive a magnet 160, which provides a magnetic field to facilitate a subset of a molecular diagnostic protocol, and detection chamber heaters 157, which allows amplification of nucleic acids for molecular diagnostic protocols requiring heating and cooling of the nucleic acid (e.g. PCR). Preferably, the linear actuator 146 is a scissor jack actuator configured to apply substantially uniform pressure over all occlusion positions of a microfluidic cartridge 210 aligned within the molecular diagnostic module 130, and to operate in at least two configurations. In a retracted configuration 146a, as shown in FIG. 9A, the scissor jack actuator has not linearly displaced the cartridge platform 141, and in an extended configuration 146b, as shown in FIG. 9B, the scissor jack actuator has linearly displaced the microfluidic cartridge 210 to position the microfluidic cartridge 210 between the subsystems 153, and 180, and the magnet 160 and detection chamber heaters 157. Additionally, the extended configuration 146b of the scissor jack actuator is configured to couple the nozzle 149 to a fluid port 222 of the microfluidic cartridge 210, such that the liquid handling system 250 can deliver solutions and gases for processing of biological samples. The linear actuator 146 may alternatively be any appropriate linear actuator, such as a hydraulic, pneumatic, or motor-driven linear actuator, configured to linearly displace a microfluidic cartridge within the molecular diagnostic module 130.

As shown in FIGS. 7B, 7C, and 8, a set of springs 148 is coupled to the cartridge platform 141 and functions to provide a counteracting force against the linear actuator 146 as the linear actuator 146 displaces a microfluidic cartridge 210 resting on the cartridge platform 141. The set of springs 148 thus allows the cartridge platform 141 to return to a position that allows the microfluidic cartridge 210 to be loaded and unloaded from the molecular diagnostic module 130 when the linear actuator 146 is in a retracted configuration 146b, as shown in FIG. 7B. Preferably, in the orientation shown in FIG. 7B, the set of springs 148 is located at peripheral regions of the bottom side of the cartridge platform 141, such that the set of springs 148 does not interfere with the magnet or the valve actuation subsystem 170. Alternatively, the set of springs 148 may be located at any appropriate position to provide a counteracting force against the linear actuator 146. In a specific example shown in FIG. 6A, the set of springs 148 comprises four springs located near corners of the bottom side of the cartridge platform 141, but in other variations, the set of springs 148 may comprise any appropriate number of springs. Each spring of the set of springs 148 is also preferably housed within a guide to prevent deviations from linear vertical motions (in the orientation shown in FIG. 7B); however, each spring in the set of springs 148 may alternatively not be housed within a guide. In an alternative embodiment of the molecular diagnostic module 130, the set of springs 148 may altogether be replaced by a second linear actuator configured to linearly displace a microfluidic cartridge 210, resting on the cartridge platform 141, in a direction opposite to the displacements enforced by the linear actuator 146.

Similarly, the nozzle 149, the heating and cooling subsystem 150, the cartridge heater 153, and the magnet 160 are preferably coupled to springs, such that springs are positioned between elements 149, 150, 153, and 160, and substrates that elements 149, 150, 153, and 160 are mounted to. Alternatively an elastomeric material is preferably positioned between elements 149, 150, 153, and 160, and substrates that elements 149, 150, 153, and 160 are mounted to. The springs and/or elastomeric material function to provide proper functioning and alignment of subsystems of the molecular diagnostic module 130 as the linear actuator 146 is extended or retracted, contributing to reliability and a reduction in stack up tolerance risk. The springs and/or elastomeric material further function to allow more pressure to be applied to occlusion positions of a microfluidic cartridge 210 aligned within the molecular diagnostic module 130, and an appropriate pressure to be applied to elements 149, 150, 153 and 160 of the molecular diagnostic module 130. Thus, proper contact is maintained between elements 149, 150, 153, and 160, and a microfluidic cartridge 210 being manipulated by the molecular diagnostic module. These elements are described in further detail below.

1.2.2 Molecular Diagnostic Module—Heating/Cooling Subsystem and Magnet

The heating and cooling subsystem 150 of the molecular diagnostic module 130 comprises a cartridge heater 153, a fan 155, and a set of detection chamber heaters 157 and functions to controllably heat portions of a microfluidic cartridge 210 for processing of a biological sample containing nucleic acids according to a molecular diagnostic protocol. In the orientation of an embodiment of the molecular diagnostic module 130 shown in FIGS. 7A-7C, the cartridge heater 153 is preferably coupled to the linear actuator 146 of the cartridge receiving module 140 and configured to span a central region of a microfluidic cartridge 210 aligned within the molecular diagnostic module 130, the fan 155 is located at a back wall of the cartridge receiving module 140, and the set of detection chamber heaters 157 is located inferior to a set of detection chambers 213 of the microfluidic cartridge 210. In alternative embodiments of the molecular diagnostic module 130, the heating and cooling subsystem 150 may have any appropriate alternative configuration that provides controlled heating and cooling to a microfluidic cartridge within the molecular diagnostic module 130.

The cartridge heater 153 functions to transfer heat to a heating region 224 of a microfluidic cartridge 210, for inducing a pH shift to release bound nucleic acids from magnetic beads within the heating region 224. The cartridge heater 153 is preferably a plate-shaped heater configured to transfer heat to the microfluidic cartridge 210 only from one side of the cartridge heater 153, such that heat flows through one face of the plate-shaped heater to the microfluidic cartridge 210. In a specific example, the cartridge heater 153 is a silicon wafer etched to be conductive and form a resistance heater. In the preferred variation, the cartridge heater 153 is either flip-chip bonded (i.e., soldered to back side of a circuit board), or wire bonded to a circuit board, and then coupled using linear bearings and springs to a plate coupled to the linear actuator 146. The preferred variation allows independent control of 12 independent channels, corresponding to 12 different pathways for sample processing. In another variation, heating through one face is accomplished using a plate-shaped resistance heater that has one exposed face and thermal insulation covering all other faces, and in yet another variation heating through one face is accomplished using a Peltier heater. In a variation of the cartridge heater 153 using a Peltier heater, the cartridge heater 153 comprises a thermoelectric material, and produces different temperatures on opposite faces of the cartridge heater 153 in response to a voltage difference placed across the thermoelectric material. Thus, when a current flows through the Peltier heater, one face of the Peltier heater lowers in temperature, and another face of the Peltier heater increases in temperature. Alternative variations of the cartridge heater 153 can be used to appropriately transfer heat to a heating region 224 of the microfluidic cartridge 210.

Preferably, the cartridge heater 153 is configured to linearly translate with the linear actuator 146 of the cartridge receiving module 140, in order to align with a heating region 224 spanning a central portion of a microfluidic cartridge 210 aligned within the molecular diagnostic module 130. In one variation, the cartridge heater 153 is preferably fixed relative to the linear actuator 146 such that (in the orientation shown in FIGS. 7B-7C), the cartridge heater 153 can only move vertically with the linear actuator. In an alternative variation, the cartridge heater 153 may additionally be configured to translate laterally with a horizontal plane (in the orientation shown in FIGS. 7B-7C), such that the cartridge heater 153 can translate in at least two perpendicular coordinate planes. In this alternative variation, the cartridge heater 153 can be configured to sweep across a surface of a microfluidic cartridge 210 aligned within the molecular diagnostic module 130, or to translate in response to motion of the microfluidic cartridge 210, such that the position of the cartridge heater 153 relative to a heating region 224 of the microfluidic cartridge 210 is always fixed.

The fan 155 functions to modulate heat control within the molecular diagnostic module 130, by enabling heat transfer from warm objects within the molecular diagnostic module 130 to cooler air external to the molecular diagnostic module 130. In the orientation shown in FIG. 6A, the fan 155 is preferably located at a back face of the molecular diagnostic module 130, such heat within the molecular diagnostic module 130 is transferred out of the back face of the molecular diagnostic module 130 to cooler air external to the molecular diagnostic module. In a specific embodiment, the molecular diagnostic module 130 comprises four fans 155 located at the back face of the molecular diagnostic module 130; however, in alternative embodiments the molecular diagnostic module 130 may comprise any appropriate number of fans located at any appropriate position of the molecular diagnostic module 130. In one variation, the fan 155 may be passive and driven solely by convection currents resulting from motion of hot air within the molecular diagnostic module to cooler air outside of the molecular diagnostic module; however, in alternative variations, the fan 155 may be motor-driven and configured to actively cool internal components of the molecular diagnostic module 130 if molecular diagnostic module elements exceed a certain threshold temperature.

The set of detection chamber heaters 157 functions to individually heat detection chambers of a set of detection chambers 213 within a microfluidic cartridge 210. Each detection chamber heater in the set of detection chamber heaters 157 is preferably configured to heat one side of one detection chamber in the set of detection chambers 213, and is preferably located such that the extended configuration 146b of the linear actuator 146 of the cartridge receiving module 140 puts a detection chamber in proximity to a detection chamber heater. As mentioned above, the set of detection chamber heaters 157 is preferably coupled to springs or an elastomeric layer to ensure direct contact between the set of detection chamber heaters and a set of detection chambers, without compressively damaging the set of detection chamber heater 157. Preferably, each detection chamber heater is configured to contact a surface of a detection chamber in the extended configuration 146b of the linear actuator 146; however, each detection chamber heater may be further configured to couple to a detection chamber in the extended configuration 146b of the linear actuator 146. In a first variation, the set of detection chamber heaters 157 comprises silicon chip heaters flip chipped to one surface of a flexible printed circuit board, with a set of springs coupled to an opposite surface of the flexible printed circuit board, such that each spring in the set of springs aligns with a detection chamber heater. In the first variation, contact between each detection chamber heater and a detection chamber is thus maintained by a biasing force provided by an individual spring through the flexible printed circuit board. In a second variation, the set of detection chamber heaters 157 comprises silicon chip heaters flip chipped to one surface of a rigid printed circuit board, with a set of springs coupled to an opposite surface of the rigid printed circuit board. In the second variation, the set of springs thus function to collectively transfer a force through the rigid printed circuit board to maintain contact between the set of detection chamber heaters and a set of detection chambers. Preferably, each detection chamber heater in the set of detection chamber heaters 157 is configured to contact and heat a bottom surface of a detection chamber (in the orientation shown in FIG. 7B); however, each detection chamber heater may alternatively be configured to contact and heat both a top and a bottom surface of a detection chamber. Additionally, each detection chamber heater preferably corresponds to a specific detection chamber of the set of detection chambers 213 and functions to individually heat the specific detection chamber; however, alternatively, each detection chamber heater may be configured to heat multiple detection chambers in the set of detection chambers 213. Preferably, all detection chamber heaters in the set of detection chamber heaters 157 are identical; however, the set of detection chamber heaters 157 may alternatively not comprise identical detection chamber heaters.

In one variation, each detection chamber heater in the set of detection chamber heaters 157 comprises a donut-shaped heater, configured to encircle a surface of a detection chamber. The donut-shaped heater may further include a conducting mesh configured to allow detection through the heater while still allowing efficient heat transfer to the detection chamber. In an alternative variation, each detection chamber heater in the set of detection chamber heaters 157 may include a plate-shaped Peltier heater, similar to Peltier cartridge heater 153 described above. In this alternative variation, each detection chamber heater is thus configured to heat one side of a detection chamber through one face of the detection chamber heater. In one specific example, the molecular diagnostic module 130 comprises 12 diced silicon wafers with conductive channels flip chipped to 12 detection chambers, providing resistive heating to each of the 12 detection chambers. In another specific example, the molecular diagnostic module 130 comprises a 12 Peltier detection chamber heaters configured to heat 12 detection chambers of a microfluidic cartridge 210 aligned within the molecular diagnostic module 130. In other alternative variations, each detection chamber heater may comprise any appropriate heater configured to individually heat a detection chamber.

The magnet 160 of the molecular diagnostic module 130 functions to provide a magnetic field for isolation and extraction of nucleic acids bound to magnetic beads within a microfluidic cartridge 210, aligned within the molecular diagnostic module 130. Preferably, the magnet 160 is fixed within the molecular diagnostic module 130, such that the extended configuration 146b of the linear actuator 146 allows the magnet 160 to pass through the magnet receiving slot 144 of the cartridge receiving module 140 and into a magnet housing region 218 of the microfluidic cartridge 210. In an example, as shown in FIGS. 7A-7C, the magnet 160 is a rectangular prism-shaped magnet 160 fixed under the cartridge platform 141, and configured to pass through the cartridge platform 141, into a magnet housing region 218 located under the heating region 224 of the microfluidic cartridge 210. Preferably, the magnet 160 is one of two or three magnets lined up in parallel, such that each of the fluidic pathways of a microfluidic cartridge housing the magnets is exposed to two or three times as much magnetic flux, and two to threes times as many opportunities to capture magnetic beads. Alternatively, the magnet 160 is a single magnet configured to expose a set of fluidic pathways to a magnetic field. Preferably, the magnet 160 or group of multiple magnets is coupled to a magnet holder within the molecular diagnostic module 130. Additionally, the magnet holder is preferably composed of an insulating material, such that the magnet holder does not interfere with proper functioning of the cartridge heater 153. Alternatively, the magnet holder may not be composed of an insulating material.

In one variation, the magnet 160 or group of multiple magnets comprises a permanent magnet, composed of a magnetized material (e.g., a ferromagnet) providing a substantially fixed magnetic field. In an alternative variation, the magnet 160 or group of multiple magnets comprises an electromagnet configured to provide a modifiable magnetic field, such that the intensity of the magnetic field can be adjusted, the polarity of the magnetic field can be reversed, and the magnetic field can be substantially removed upon removal of a current flowing within the electromagnet. Preferably, the magnet 160 or group of magnets is also fixed relative to the molecular diagnostic module 130; however, the magnet 160 or group of magnets may alternatively be configured to translate vertically (in the orientation shown in FIG. 7B), such that the magnet 160 or group of magnets can extend into and retract from the magnet receiving slot 144 of the cartridge platform 141 and the magnet housing region 218 of the microfluidic cartridge 210. Additionally, the magnet 160 or group of magnets preferably rides on linear bearings and springs (or an elastomeric material) to ensure proper contact with a microfluidic cartridge in an extended configuration 146b of the linear actuator 146, in a manner that allows most of force from the linear actuator 146 to translate to full occlusion of a subset of the set of occlusion positions (i.e., without leakage).

Alternative configurations and/or compositions of the magnet 160 may also be appropriate in facilitating isolation and extraction of nucleic acids bound to magnetic beads within the microfluidic cartridge 210.

1.2.3 Molecular Diagnostic Module—Valve Actuation Subsystem

As shown in FIGS. 10A-11C, the valve actuation subsystem 170 of the molecular diagnostic module 130 comprises a set of pins 172 configured to translate linearly within a pin housing 175, by sliding a cam card 177 laterally over the pins 172. The valve actuation subsystem 170 functions to provide a biasing force to deform an object in contact with the set of pins 172. In a configuration wherein a microfluidic cartridge 210 is aligned within the molecular diagnostic module 130, the valve actuation subsystem 170 thus functions to occlude a fluidic pathway 220 of the microfluidic cartridge 210 at a set of occlusion positions 226, to control flow of a biological sample containing nucleic acids, reagents and/or air through the microfluidic cartridge 210. In an embodiment of the molecular diagnostic module shown in FIGS. 7D-7E, the set of pins 172 and the pin housing are located directly under the microfluidic cartridge 210, such that the set of pins can access the microfluidic cartridge 210 through the valve actuation accommodating slots 145 of the cartridge platform 141. The cam card 177 in the embodiment is positioned under the set of pins and is coupled to a linear cam card actuator 178 configured to laterally displace the cam card 177 to vertically displace pins of the set of pins 172. Preferably, as shown in FIG. 11A, the cam card 177 rests on a low friction surface configured to facilitate lateral displacement of the cam card 177; however, the cam card 177 may alternatively rest on a bed of ball bearings to facilitate lateral displacement of the cam card 177, or may rest on any feature that allows the cam card 177 to be laterally displaced by the linear cam card actuator 178.

Figure 7D:
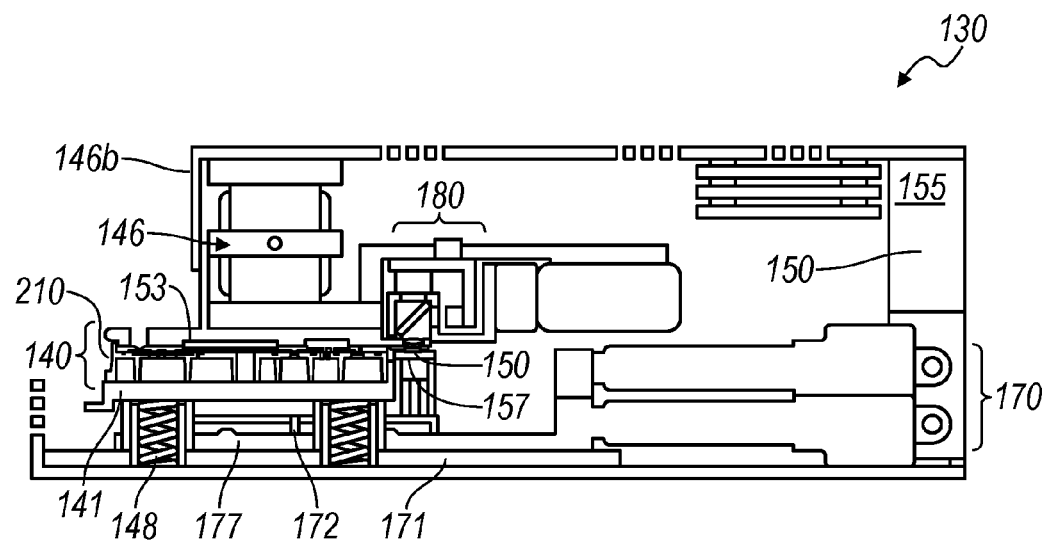
Figure 7E:
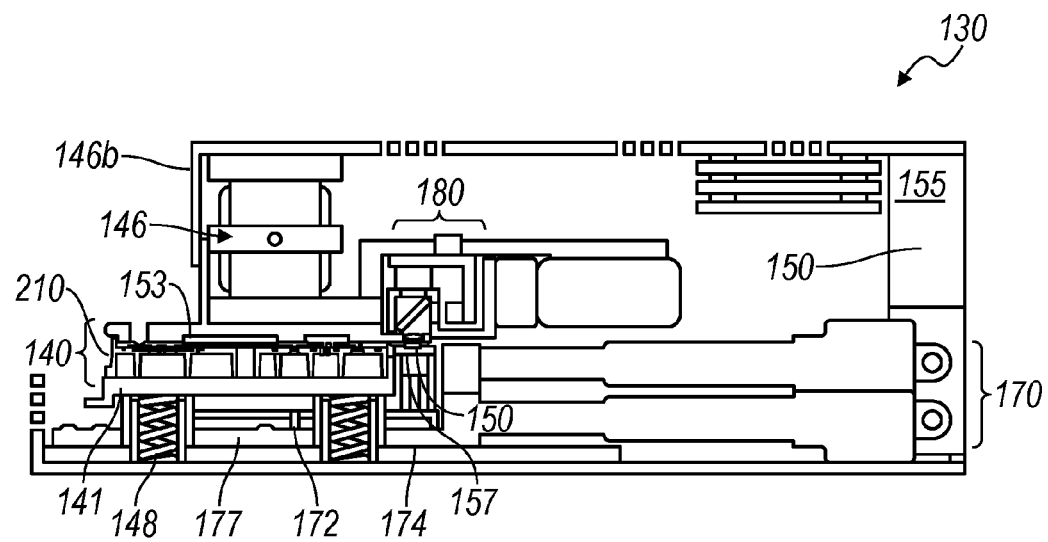
Figure 11A:
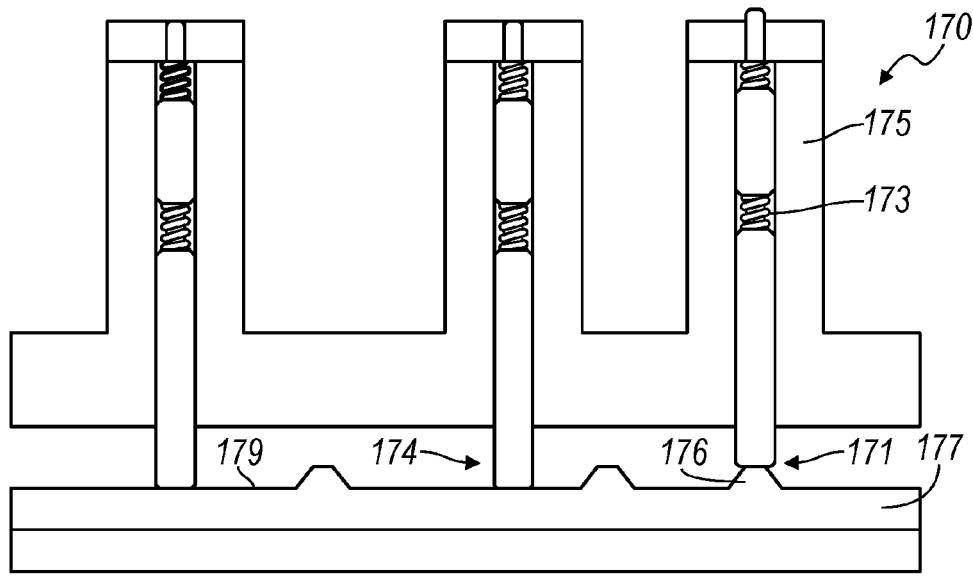
FIGS. 11A-11C depict an embodiment of a valve actuation subsystem of a molecular diagnostic module.
Figure 11B:
Figure 11B:
Figure 11B:
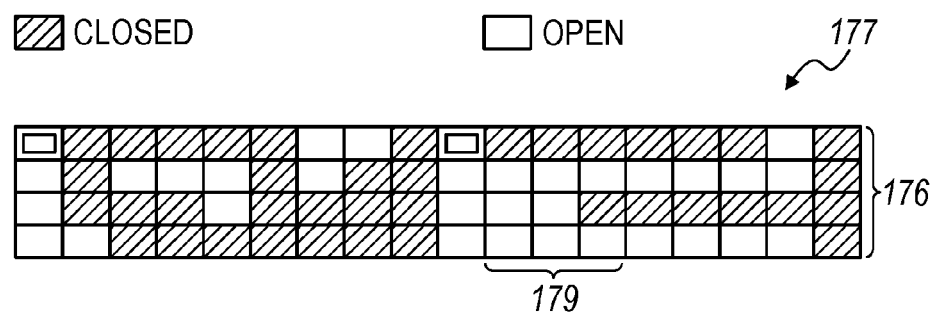

The cam card 177, as shown in FIGS. 7D and 11A, includes a set of hills 176 and valleys 179, and functions to transform linear motion in one plane to vertical motion in another plane. In one variation, the cam card 177 is coupled to a linear actuator and contacts the ends of pins in a set of pins 172, such that when a hill 176 of the cam card 177 passes under a pin, the pin is in a raised configuration 177a, and when a valley 179 of the cam card 177 passes under a pin, the pin is in a lowered configuration 177b. The hills 176 and valleys 179 of the cam card 177 are preferably in a set configuration, as shown in FIG. 11B, such that lateral motion of the cam card 177 to a set position raises a fixed subset of the set of pins 172. In this manner, lateral movement of the cam card 177 to different positions of a set of positions consistently raises different subsets of the set of pins 172 to occlude different portions of a fluidic pathway 220 of a microfluidic cartridge 210 in contact with the set of pins 172. Thus, portions of a fluidic pathway 220 may be selectively occluded and opened to facilitate processing of a biological sample according to any appropriate tissue, cellular, or molecular diagnostic assay protocol. In one variation, the cam card is configured to be laterally displaced in two coordinate directions within a plane (e.g., by x-y linear actuators), and in another variation, the cam card is configured to be laterally displaced in only one coordinate direction within a plane (e.g., by a single linear actuator). In a specific example, the hills 176 of the cam card 177 are raised 1 mm above the valleys 179 of the cam card 177, the hills 176 and valleys 179 each have a 2 mm wide plateau region, and a hill 176 region slopes down to a valley region 179 at a fixed angle over a 2 mm length. In the specific example, the cam card 177 is driven by a Firgelli linear actuator. Alternative variations may include any appropriate configurations and geometries of a cam card with hills 176 and valleys 179, driven by any appropriate actuator.

In alternative embodiments of the valve actuation subsystem 170, the cam card 177 may be a cam card wheel comprising a set of hills 176 and valleys 179 on a cylindrical surface, and configured to convert rotary motion to linear (i.e., vertical) motion of the set of pins 172. The cam card wheel may be configured to contact ends of pins in the set of pins 172, and may be coupled to a motor shaft and driven by a motor. In other alternative embodiments of the valve actuation subsystem 170, the cam card 177 may altogether be replaced by a set of cams, each configured to individually rotate about an axis. In these alternative embodiments, rotating subsets of the set of cams raises corresponding subsets of the set of pins, and occludes specific portions of a fluidic pathway 220 of a microfluidic cartridge 210 in contact with the set of pins 172.

Figure 11C:
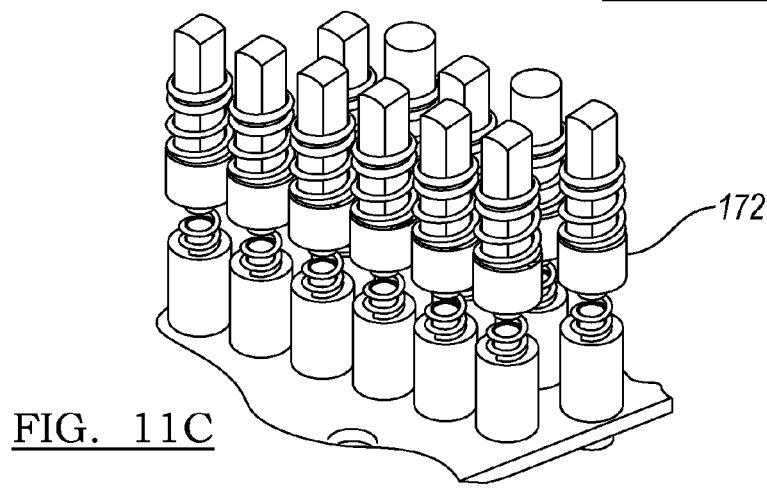
Figure 12A:
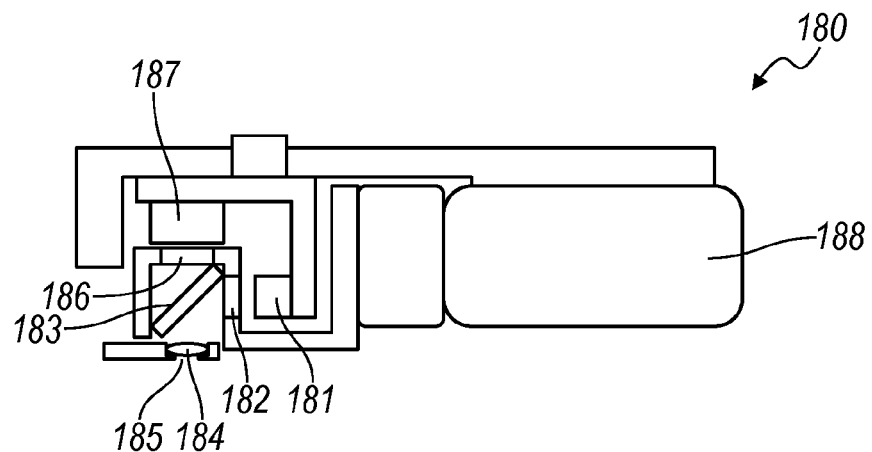
FIGS. 12A-12D depict elements of an embodiment of an optical subsystem of a molecular diagnostic module.
Figure 12B:
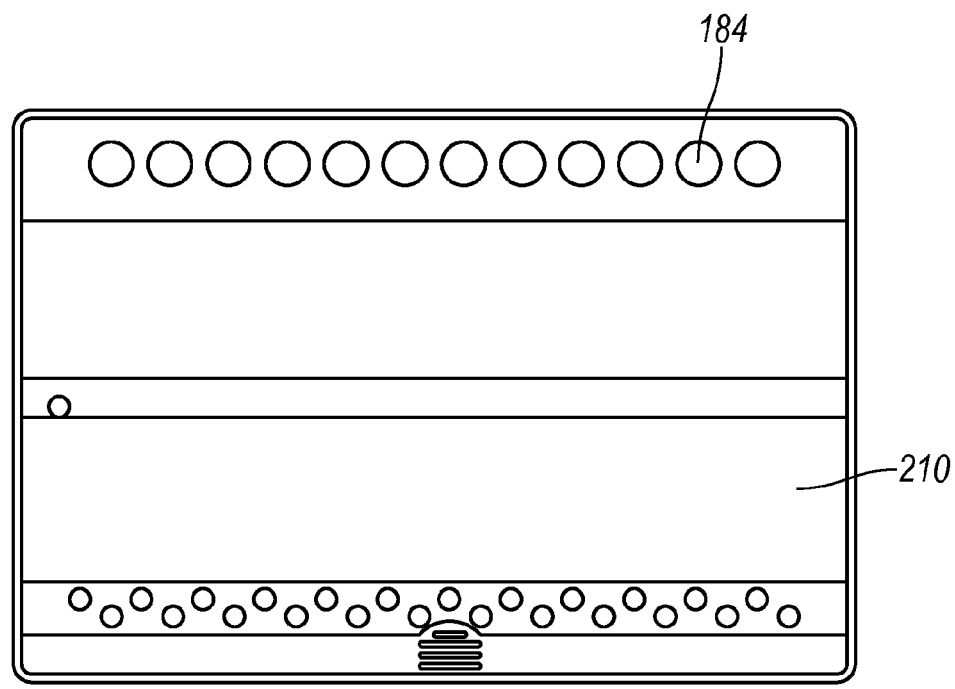
Figure 12C:
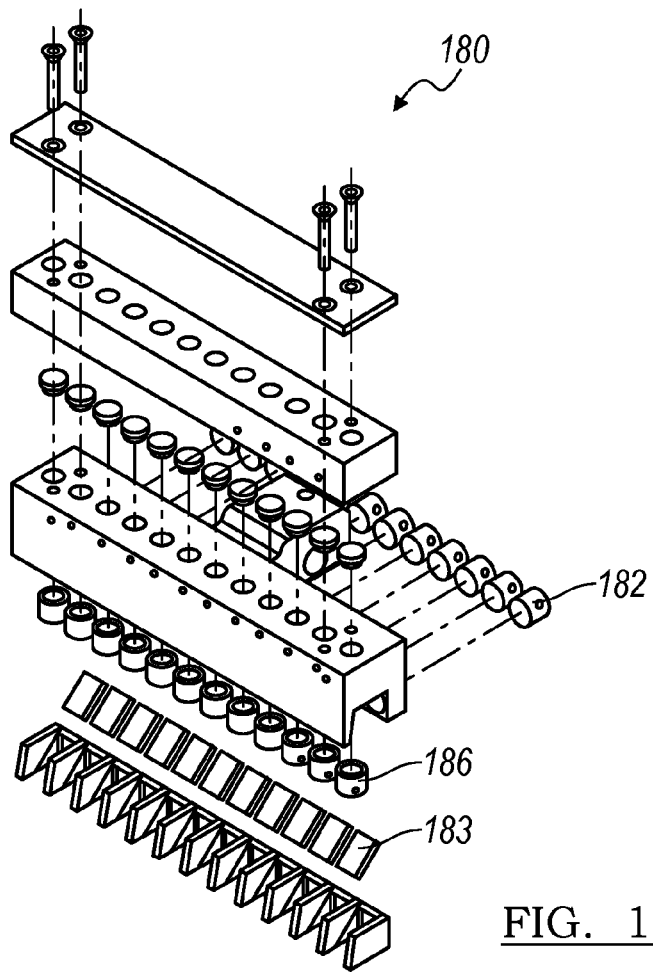
Figure 12D:
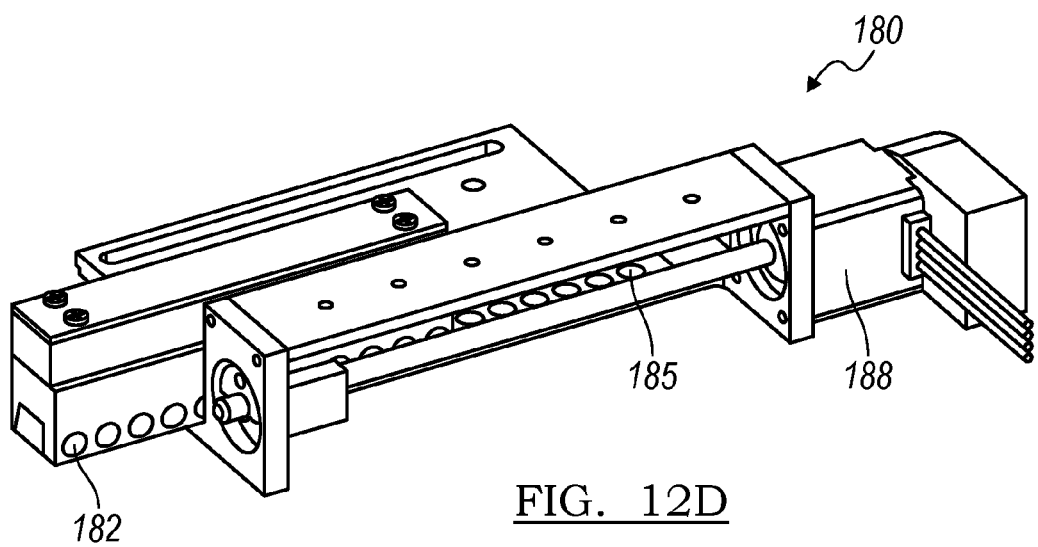

The set of pins 172 functions to selectively occlude portions of a fluidic pathway 220 of a microfluidic cartridge 210 at least at subsets of a set of occlusion positions 226. The pins of the set of pins 172 are preferably cylindrical and, in the orientation shown in FIG. 11A, configured to slide over a cam card 177 and within a pin housing 175. Each pin in the set of pins 172 preferably also includes a first spring 173 that functions to provide a counteracting force to restore a pin to a lowered configuration 177b; however, each pin in the set of pins 172 may alternative not include a first spring 173, and rely solely on gravity to return to a lowered configuration 177b. Preferably, as shown in FIG. 11C, each pin is also composed of two parts separated by a second spring, which functions to allow sufficient force to fully occlude a microfluidic channel but prevents forces from being generated that could damage the pin, microfluidic cartridge and/or cam card. Each pin also preferably comprises a first region 171 configured to slide within the pin housing 175, and a second region 174 configured to exit the pin housing 175. The second region 174 is preferably of a smaller dimension than the first region 171, such that each pin is constrained by the pin housing 175 to be raised by a limited amount. Alternatively, the first region 171 and the second region 174 may have any appropriate configuration to facilitate raising and lowering of a pin by a fixed amount. In a specific example, the valve actuation subsystem 170 comprises 12 sets of pins 172 configured to selectively occlude 12 fluidic pathways 212 of a microfluidic cartridge 210 aligned within the molecular diagnostic module; however, other embodiments may comprise any appropriate number of sets of pins 172.

In the orientation shown in FIG. 11A, each pin in the set of pins 172 preferably has a circular cross section and round ends, configured to facilitate sliding within a pin housing 175, sliding over a cam card 177 surface, and occlusion of a fluidic pathway 220. Alternatively, each pin may comprise any appropriate cross-sectional geometry (e.g., rectangular) and/or end shape (e.g., flat or pointed) to facilitate occlusion of a fluidic pathway 220. Preferably, the surface of each pin in the set of pins 172 is composed of a low-friction material to facilitate sliding motions (i.e., over a cam card 177 or within a pin housing 175); however, each pin may alternatively be coated with a lubricant configured to facilitate sliding motions.

The pin housing 175 functions to constrain and guide the motion of each pin in the set of pins 172, as the cam card 177 slides under the set of pins 172. Preferably, the pin housing 175 comprises a set of pin housing channels 169 configured to surround at least one pin in the set of pins 172. In one variation, each pin in the set of pins 172 is surrounded by an individual channel of the set of pin housing channels 169; however, in another variation a channel of the set of pin housing channels 169 may be configured to surround multiple pins in the set of pins 172. In an example shown in FIGS. 7D-7E and 11A, the pin housing is located under the cartridge platform 141, such that the set of pin housing channels 169 is aligned with the set of valve actuation accommodating slots 145, to provide access, by the set of pins 172, to a microfluidic cartridge 210 aligned on the cartridge platform 141. In the example, the pin housing 175 thus constrains the set of pins 172, such that each pin can only move linearly in a vertical direction. Each pin housing channel preferably has a constricted region 168 configured to limit the motion of a pin within a pin channel; however, each pin housing channel may alternatively not include a constricted region. Preferably, surfaces of the pin housing 175 contacting the set of pins 172 are composed of a low friction material to facilitate sliding of a pin within a pin housing channel; however, surfaces of the pin housing 175 contacting the set of pins 172 may alternatively be coated with a lubricant configured to facilitate sliding motions. Other variations of the pin housing 175 and the set of pins 172 may include no additional provisions to facilitate sliding of a pin within a pin housing channel.

1.2.4 Molecular Diagnostic Module—Optical Subsystem

As shown in FIGS. 12A-12D, the optical subsystem 180 of the molecular diagnostic module 130 comprises a set of light emitting diodes (LEDs) 181, a set of excitation filters 182 configured to transmit light from the set of LEDs 181, a set of dichroic mirrors 183 configured to reflect light from the set of excitation filters 182 toward a set of apertures 185 configured to transmit light toward a set of nucleic acid samples, a set of emission filters 186 configured to receive and transmit light emitted by the set of nucleic acid samples, and a set of photodetectors 187 configured to facilitate analysis of light received through the set of emission filters 186. The optical subsystem 180 may further comprise a set of lenses 184 configured to focus light onto the set of nucleic acid samples. The optical subsystem 180 thus functions to transmit light at excitation wavelengths toward a set of nucleic acid samples and to receive light at emission wavelengths from a set of nucleic acid samples. Preferably, the optical subsystem 180 is coupled to an optical subsystem actuator 188 configured to laterally displace and align the optical subsystem 180 relative to the set of nucleic acid samples, and is further coupled to a linear actuator 146 of the cartridge receiving module 140 to position the optical subsystem 180 closer to the set of nucleic acid samples. Alternatively, the optical subsystem 180 may not be coupled to a linear actuator 146 of the cartridge receiving module 140, and may only be configured to translate laterally in one direction. In a specific example, the optical subsystem 180 comprises a set of 12 apertures, a set of 12 lenses, a set of 12 dichroic mirrors, a set of 12 excitation filters, a set of 12 LEDs, a set of 12 emission filters, and a set of 12 photodetectors. In the specific example, as shown in FIG. 7A-7E, the optical subsystem 180 is located within the molecular diagnostic module 130 and coupled to the linear actuator 146 of the cartridge receiving module 140, such that, in the extended configuration 146b of the linear actuator 146, the optical subsystem 180 can be positioned closer to a microfluidic cartridge 210 aligned within the molecular diagnostic module. Conversely in the specific example, the optical subsystem 180 is positioned away from the microfluidic cartridge 210 in the retracted configuration 146a of the linear actuator 146. In the specific example, the optical subsystem 180 is further coupled to an optical subsystem actuator 188 configured to laterally displace the optical subsystem 180 relative to the microfluidic cartridge 210, such that the optical subsystem 180 can be aligned with a set of detection chambers 213 of the microfluidic cartridge 210.

Preferably, the set of LEDs 181 are not all identical but rather chosen to efficiently produce a certain band of wavelengths of light, such that light from the set of LEDs 181 can be filtered to appropriate narrow wavelengths for analysis of nucleic acid samples. Alternatively, all LEDs in the set of LEDs 181 may be identical, and produce white light comprising all wavelengths of visible light that is filtered to produce the desired wavelength, in which case the LEDs may be stationary. Preferably, the set of LEDs 181 includes phosphor-based LEDs, but the set of LEDs 181 may alternatively include any LEDs configured to provide light of the desired range of wavelengths. The LEDs of the set of LEDs 181 are preferably configured to emit light of wavelengths corresponding to at least one of the set of excitation filters 182, the set of dichroic mirrors 183, and the set of emission filters 186.

The set of excitation filters 182 is configured to align with the set of LEDs 181 in the optical subsystem 180, and functions to transmit light at excitation wavelengths toward the set of dichroic mirrors 183 of the optical subsystem 180. Preferably, the set of excitation filters 182 are not identical excitation filters, but rather chosen to transmit the different desired ranges of excitation wavelengths. Alternatively, all excitation filters of the set of excitation filters 182 are identical, and configured to transmit light having a fixed range of excitation wavelengths. In one variation, the set of excitation filters 182 includes band pass filters, configured to transmit light between two bounding wavelengths, in another variation, the set of excitation filters 182 includes short pass filters configured to transmit light below a certain wavelength, and in yet another variation, the set of excitation filters 182 includes long pass filters configured to transmit light above a certain wavelength. Preferably, the set of excitation filters 182 is interchangeable, such that individual excitation filters may be interchanged to provide different excitation wavelengths of light; however, the set of excitation filters 182 may alternatively be fixed, such that the optical subsystem 180 is only configured to transmit a fixed range of excitation wavelengths.

The set of dichroic mirrors 183 is configured to align with the set of excitation filters 182, and functions to receive and reflect light from the set of excitation filters 182 toward the detection chamber, such that light having a range of excitation wavelengths may be focused, through a set of apertures, onto a set of nucleic acid samples. The set of dichroic mirrors 183 also functions to receive and transmit light from a set of emission filters 186 toward a set of photodetectors 187, which is described in more detail below. All dichroic mirrors in the set of dichroic mirrors 183 are preferably identical in orientation relative to the set of excitation filters 182 and the set of emission filters 186, and configured to reflect and transmit the appropriate wavelengths of light for the given LED. Alternatively, the set of dichroic mirrors 183 may include identical dichroic mirrors, with regard to orientation, light transmission, and light reflection. In a specific example, in the orientation shown in FIG. 12A, the set of excitation filters 182 is oriented perpendicular to the set of emission filters 186, with the set of dichroic mirrors 183 bisecting an angle between two planes formed by the faces of the set of excitation filters 182 and the set of emission filters 186. In the specific example, light from the set of excitation filters is thus substantially reflected at a 90° angle toward the set of apertures 185, and light from the set of emission filters 186 passes in a substantially straight direction through the set of dichroic mirrors 183 toward the set of photodetectors 187. Other variations of the set of dichroic mirrors 183 may include any configuration of dichroic mirrors, excitation filters, and/or emission filters that enable transmission of light of excitation wavelengths toward a set of nucleic acid samples, and transmission of light from the set of nucleic acid samples toward a set of photodetectors 187.

In one embodiment, the optical subsystem may further include a set of lenses 184 configured to align with the set of dichroic mirrors 183, which functions to focus light, from the set of excitation filters 182 and reflected off of the set of dichroic mirrors 183, onto a set of nucleic acid samples configured to emit light in response to the light from the set of excitation filters 182. All lenses in the set of lenses 184 are preferably identical in orientation relative to the set of dichroic mirrors and in dimension; however, the set of lenses 184 may alternatively comprise non-identical lenses, such that light passing through different lenses of the set of lenses 184 is focused differently on different nucleic acid samples. In a specific example, in the orientation shown in FIG. 12A, the faces of the set of lenses 184 are oriented perpendicular to the faces of the set of excitation filters 182, to account for light reflection by the set of dichroic mirrors 183 at a 90° angle. In the specific example, the set of lenses also includes identical ¼" high numerical aperture lenses. In other variations, the set of lenses 184 may be oriented in any appropriate configuration for focusing light from the set of dichroic mirrors 183 onto a set of nucleic acid samples, and may include lenses of any appropriate specification (i.e., numerical aperture).

The set of apertures 185 is located on an aperture substrate 189 and configured to align with the set of lenses 184, and functions to allow focused light from the set of lenses 184 to pass through to the set of nucleic acid samples. The aperture substrate 189 is preferably coupled to the linear actuator 146 of the cartridge receiving module 140, which allows the optical subsystem 180 to linearly translate and be positioned near and away from a microfluidic cartridge 210 aligned within the molecular diagnostic module 130. Alternatively, the aperture substrate 189 may not be coupled to the linear actuator 146 of the cartridge receiving module 140. Preferably, all apertures 185 in the set of apertures 185 are identical, and configured to allow identical light profiles to be focused, through the set of lenses 184, onto a set of nucleic acid samples. Alternatively, the set of apertures 185 may not include identical apertures. In one variation, each aperture in the set of apertures 185 may be individually adjustable, in order to provide individually modifiable aperture dimensions (e.g., width, length, or diameter) to affect light exposure. In an alternative variation, each aperture in the set of apertures 185 is fixed. Other variations may include interchangeable aperture substrates 189, such that features of the set of apertures (e.g., aperture dimensions, number of apertures) may be adjusted by interchanging aperture substrates 189.

The set of emission filters 186 is configured to align with the set of dichroic mirrors, and functions to transmit emission wavelengths of light from the set of nucleic acid samples, and to filter out excitation wavelengths of light.

Preferably, each emission filter of the set of emission filters 186 are configured to transmit light having a fixed range of emission wavelengths, while blocking light of excitation wavelengths. Alternatively, the set of emission filters 186 may comprise identical emission filters, such that individual emission filters of the set of emission filters 186 are configured to transmit the same ranges of emission wavelengths. In one variation, the set of emission filters 186 includes band pass filters, configured to transmit light between two bounding wavelengths, in another variation, the set of emission filters 186 includes short pass filters configured to transmit light below a certain wavelength, and in yet another variation, the set of emission filters 186 includes long pass filters configured to transmit light above a certain wavelength. Preferably, the set of emission filters 186 is interchangeable, such that individual emission filters may be interchanged to transmit and/or block different wavelengths of light; however, the set of emission filters 186 may alternatively be fixed, such that the optical subsystem 180 is only configured to transmit a fixed range of emission wavelengths.

The set of photodetectors 187 is configured to align with the set of emission filters 186, and functions to receive light from the set emission filters to facilitate analysis of the set of nucleic acid samples. All photodetectors in the set of photodetectors 187 are preferably identical; however, the set of photodetectors 187 may alternatively include non-identical photodetectors. Preferably, the set of photodetectors 187 includes photodiodes comprising a photoelectric material configured to convert electromagnetic energy into electrical signals; however, the set of photodetectors 187 may alternatively comprise any appropriate photodetectors for facilitating analysis of biological samples, as is known by those skilled in the art.

The optical subsystem actuator 188 is coupled to the optical subsystem 180, and functions to laterally translate the optical subsystem 180 relative to a set of nucleic acid samples being analyzed. Preferably, the optical subsystem actuator 188 is a linear actuator configured to translate the optical subsystem 180 in one dimension; however, the optical subsystem actuator 188 may alternatively be an actuator configured to translate the optical subsystem 180 in more than one dimension. In a specific example, as shown in FIGS. 7A-7D and 12D, the optical subsystem actuator 188 is configured to translate the optical subsystem 180 laterally in a horizontal plane, to align the optical subsystem 180 with a set of detection chambers 213 of a microfluidic cartridge 210 within the molecular diagnostic module 130. In another example, the optical subsystem may be configured as a disc revolving around an axis with the LEDs and photodetectors stationary and the disc containing the filters. In other variations, the optical subsystem actuator 188 may be configured in any appropriate manner to facilitate alignment of the optical subsystem 180 relative to a set of nucleic acid samples being analyzed.

1.2.5 Molecular Diagnostic Module—Alternative Embodiments and Variations

Figure 13:
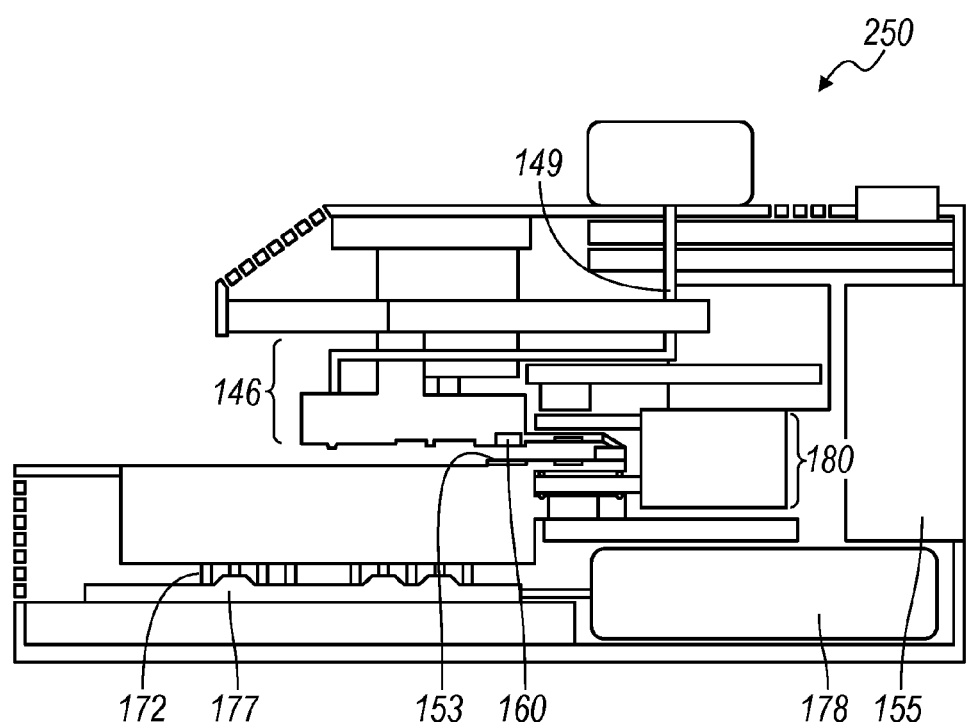
FIG. 13 depicts a side view of an alternative embodiment of a molecular diagnostic module for processing and detecting nucleic acids.

As described above, alternative embodiments of the molecular diagnostic module 130 and alternative variations of subsystems and elements of the molecular diagnostic module 130 may be configured to process a biological sample containing nucleic acids, isolate nucleic acids from the biological sample, and detect nucleic acids. An example of an alternative embodiment of a molecular diagnostic module 130, as shown in FIG. 13, includes a cartridge receiving module 140', a heating and cooling subsystem 150', a magnet 160', a valve actuation subsystem 170', and an optical subsystem 180', and functions to manipulate an alternative microfluidic cartridge 210' for processing of biological samples containing nucleic acids. Other alternative embodiments of the molecular diagnostic module 130" may be configured to receive alternative microfluidic cartridges 210", for processing of biological samples containing nucleic acids.

1.3 System—Assay Strip

Figure 18A:
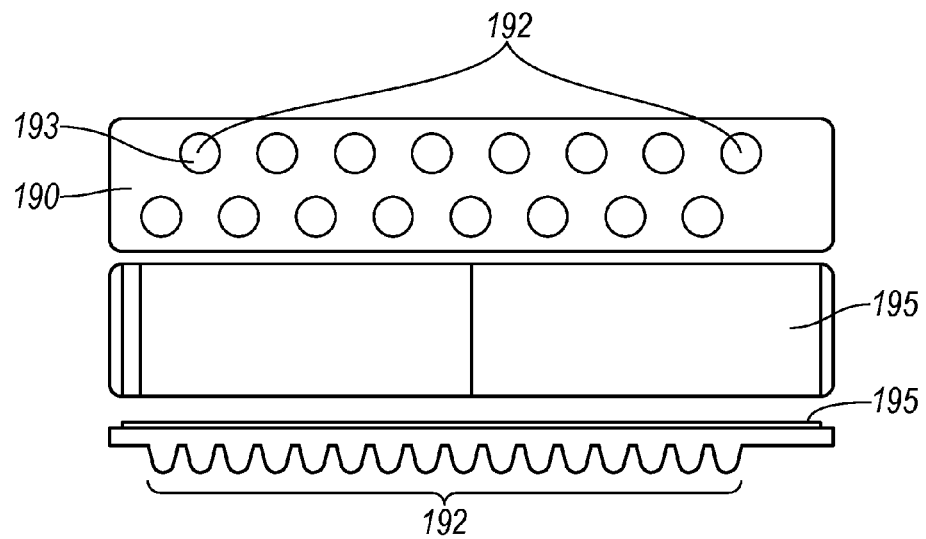
FIGS. 18A-18B depict an embodiment of an assay strip to facilitate analysis of a sample containing nucleic acids.
Figure 18B:
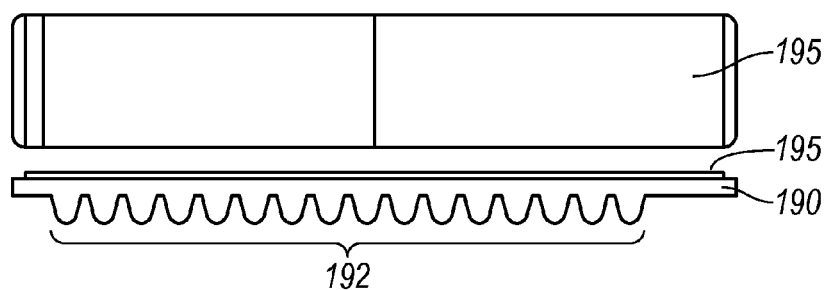

As shown in FIGS. 18A and 18B, the assay strip 190 comprises an assay strip substrate 191 comprising a set of wells 192, and typically a puncturable foil seal 195, and functions to facilitate combination of a set of nucleic acid samples with a set of molecular diagnostic reagents for amplification and/or detection of a nucleic acid sequence or sequences. Preferably, the entire assay strip 190 is configured to be a consumable (i.e., disposable), such that the assay strip 190 can be used during multiple runs of the system 100, then the assay strip 190 is disposed of once all of the wells 192, containing unitized reagents for a single test or group of tests, is exhausted. Alternatively, at least a portion of the assay strip 190 is configured to be reusable, such that wells may be reloaded with reagents and reused with the system 100. In one variation of the assay strip 190, the assay strip substrate 191 is reusable, while the puncturable foil seal 195 is disposable and replaced after each run of the system 100. In another variation, the reusable assay strip substrate 191 does not require a puncturable foil seal 195, such that reagents specific to a certain nucleic acid sequences may be deposited into open wells of the assay strip substrate 191 by a user.

The assay strip substrate 191 is configured such that the assay strip 190 is capable of resting on a flat surface, and functions to define the set of wells 192 and to couple to the puncturable foil seal 195. The assay strip substrate 191 is preferably configured to be received by a corresponding assay strip holder 230 configured to hold multiple assay strips 190, but may alternatively not be configured to couple to an assay strip holder 230. The assay strip substrate 191 is preferably composed of a PCR-compatible polymer, such as polypropylene, that can be heat processed to couple to the puncturable foil seal 115, but can alternatively be composed of any appropriate material that can contain a fluid and be bonded to the puncturable foil seal 115.

The set of wells 192 of the assay strip substrate 191 function to receive at least one nucleic acid sample, and to facilitate combination of the nucleic acid sample with at least one of a set of molecular diagnostic reagents. The molecular diagnostic reagents of the set of molecular diagnostic reagents preferably comprise reagents configured to analyze the set of nucleic acid volumes for markers of at least one of gonorrhea (GC), Chlamydia (CT), herpes simplex virus (HSV), human immunodeficiency virus (HIV), human respiratory diseases, vaginal diseases, hepatitis C virus (HCV), hepatitis B virus (HBV), trichonomas, group B streptococcus (GBS), factor 2 (FII) gene, and factor five (FV) gene, but may alternatively comprise reagents used to perform alternative molecular diagnostic protocols. Preferably, the wells 193 of the assay strip substrate 191 are each configured to accommodate not only a nucleic acid sample, but also to facilitate mixing of the nucleic acid sample with at least one of a set of molecular diagnostic reagents (e.g., using a pipettor or other apparatus). Additionally, the molecular diagnostic reagents of the set of molecular diagnostic reagents preferably comprises probes and primers to detect the sample process controls provided by the capture plate, in order to verify process fidelity and assay accuracy. Preferably, the wells 193 are deep enough to facilitate mixing without splashing, and evenly spaced to facilitate aspiration, delivery, and/or mixing of multiple biological samples (e.g., with a multi-tip pipettor). Alternatively, the wells are wide and shallow to facilitate drying of reagents in the wells to increase shelf life and larger devices for mixing the nucleic acids with molecular diagnostic reagents. Each well 193 of the set of wells 192 also preferably has a rounded bottom region, as shown in FIG. 18A, to facilitate complete aspiration of a fluid from a well 193; however, each well 193 may alternatively not have a rounded bottom region. Additionally, the set of wells 192 is preferably arranged in staggered rows, which functions to facilitate access to individual wells 193 of the set of wells, to reduce one dimension of the assay strip 190, and also to prevent cross-contamination of fluids within the wells due to dripping. Alternatively, the set of wells 192 may not be arranged in staggered rows.

The puncturable foil seal 195 functions to protect the molecular diagnostic reagents stored in wells 112 from degradation, isolate each well 193 of the set of wells 192, prevent contamination of the contents of each of the set of wells 192, and provide information identifying the assay strip 190. The puncturable foil seal 195 preferably seals each well 193 of the assay strip 190, and is configured to be punctured by an external element (e.g., by a pipette tip), such that each well is sealed prior to being punctured. In one variation, the puncturable foil seal 195 also forms a seal around an element that punctures it, and in another variation, the puncturable foil seal 195 does not form a seal around an element that punctures it, in order to prevent airlock. The puncturable foil seal 195 is also preferably labeled with identifying information including at least one of manufacturer information, assay strip contents, the lot of the contents, an expiry date, and a unique electronic tag (e.g., barcode or QR code) providing more information. Preferably, the puncturable foil seal 195 does not extend beyond the footprint of the assay strip 190, but alternatively, the puncturable foil seal 195 may be any appropriate size and/or include protruding features (e.g., tabs) that facilitate handling of the assay strip.

In one variation, the assay strip 190 may be prepackaged with a set of molecular diagnostic reagents, such that each well 193 in the set of wells 192 is prepackaged with a quantity of molecular diagnostic reagents. The set of wells 192 may then be sealed by the puncturable foil seal 195, which is configured to be punctured by an external element that delivers volumes of nucleic acid samples to be combined with the set of molecular diagnostic reagents. In another variation, the assay strip 190 may not be prepackaged with a set of molecular diagnostic reagents, and the wells 193 of the assay strip 190 may not be sealed with a puncturable foil seal 195. In yet another variation, the system may comprise an empty assay strip 190 without a puncturable foil seal 195, and an assay strip 190 comprising reagents and a puncturable foil seal 195, such that a user may add specific reagents to the empty assay strip to be used in conjunction with the assay strip comprising reagents. In variations comprising a puncturable foil seal 195, the puncturable foil seal 115 is configured to be punctured by at least one external element, for co-delivery of nucleic acid samples and molecular diagnostic reagents intended to be combined.

In a specific example, the assay strip 190 has an 87 mm×16 mm footprint and comprises 24 wells 113 arranged in two staggered rows, with a 9 mm center-to-center pitch between adjacent wells 193 within each row. Each well 193 of the set of wells has a capacity of 60 µL to accommodate a volume of a molecular diagnostic reagent, 20 µL of a sample fluid, and any displacement caused by a pipette tip (e.g., 100 or 300 µL pipette tip). Each well 113 of the assay strip 190 in the specific example is also prepackaged with a quantity of molecular diagnostic reagents, and comprises a protruding top edge (75 microns high) that is heat sealed to a puncturable foil seal. The capture plate 110 in the specific example is produced by injection molding, has a footprint of 127.75 mm×85.5 mm, and is composed of a PCR-compatible polypropylene based polymer with a high vapor barrier. In the specific embodiment, the vapor barrier is further increased by depositing a thin metallic layer to the outside of the assay strip 190.

Figure 17A:
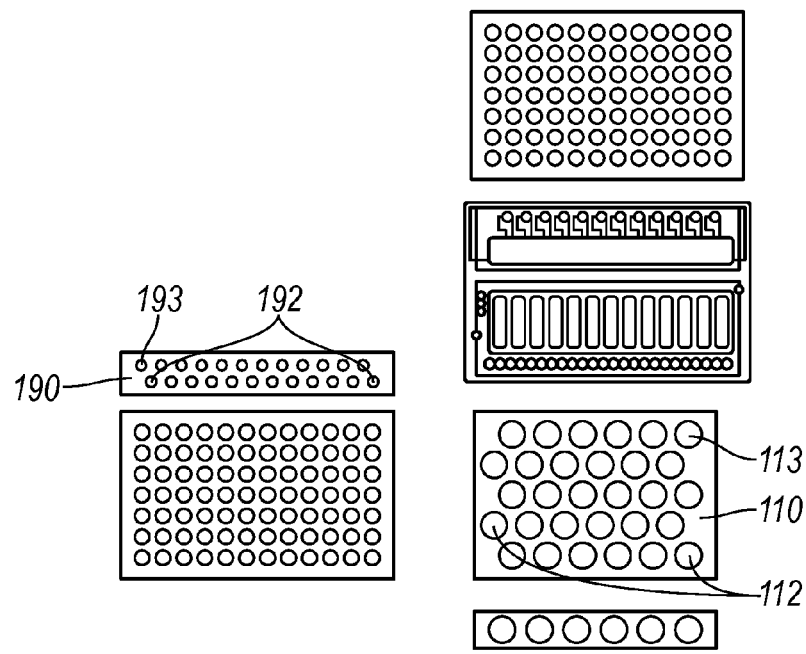
FIGS. 17A-17B show embodiments of consumables and reagents used in a system for processing and detecting nucleic acids.
Figure 17B:
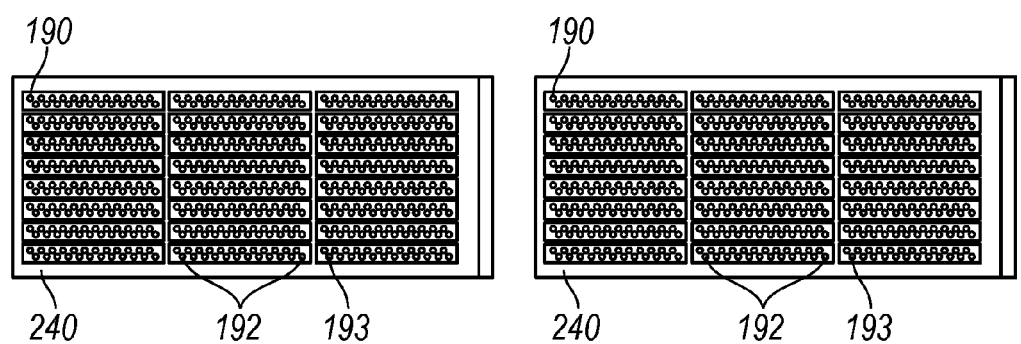

As described earlier, the assay strip 190 may be configured to be received by an assay strip holder 230. The assay strip holder 230 functions to receive and align multiple assay strips 190, such that a multichannel pipettor or other fluid delivery system may combine multiple nucleic acid samples with molecular diagnostic reagents using wells 193 of multiple assay strips 190. In one variation, the assay strip holder 230 may be configured to contain Assay strips 190 including reagents for substantially different molecular diagnostic assays, as shown in FIG. 17B, such that a single run of the system 100 involves analyzing a set of nucleic acid samples under different molecular diagnostic assays. In another variation, the assay strip holder 230 may be configured to contain assay strips 190 including reagents for identical molecular diagnostic assays, such that a single run of the system 100 involves analyzing a set of nucleic acid samples under the same molecular diagnostic assay. Preferably, the assay strip holder 230 is composed of a material that is dishwasher safe and autoclavable, configured to hold the assay strips 190 in place during handling by a fluid delivery system (e.g., pipettor), and configured such that the assay strips 190 avoid protruding over an edge of the assay strip holder 230, but the assay strip holder 230 is constructed to facilitate insertion and removal of the assay strips 190 from the assay strip holder 230.

Figure 19:
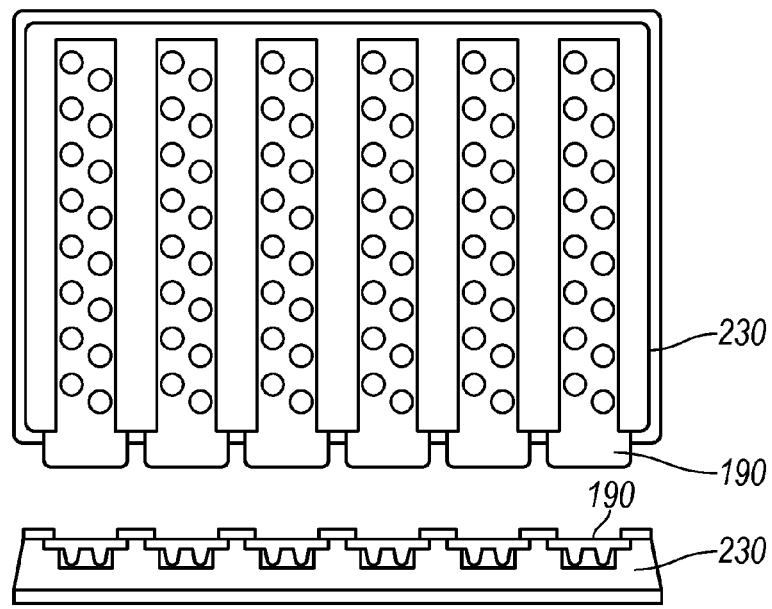
FIG. 19 depicts an embodiment of an assay strip holder.
Figure 20:
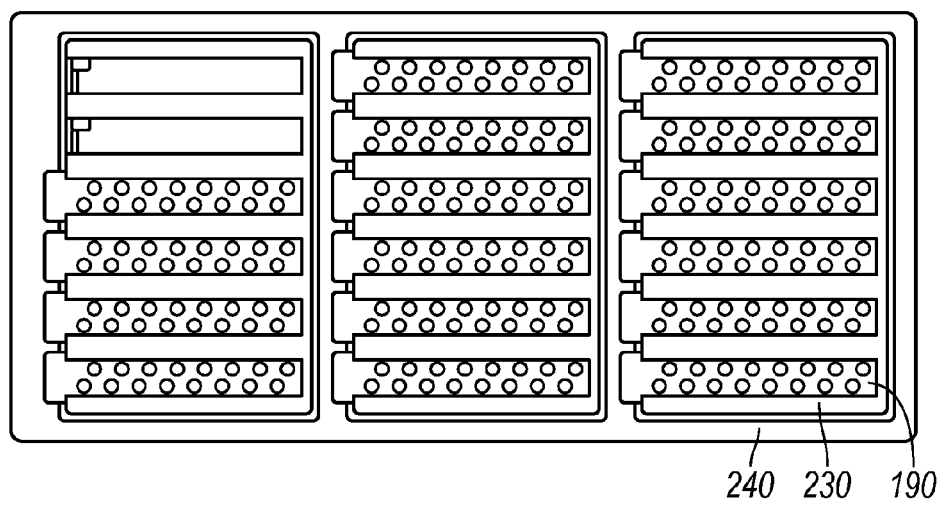
FIG. 20 depicts an embodiment of an assay strip carrier.
Figure 21A:
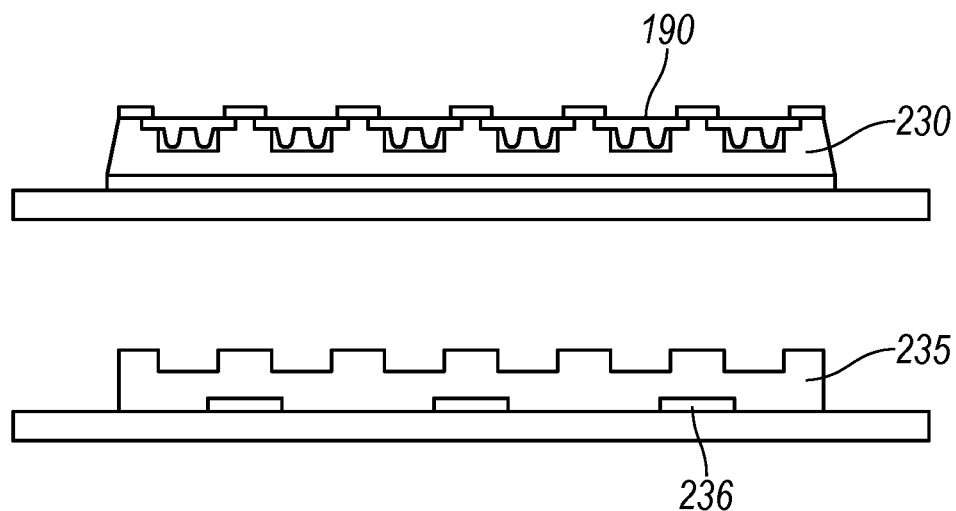
FIGS. 21A-21B show alternative embodiments of assay strip holders and assay strips, respectively.
Figure 21B:
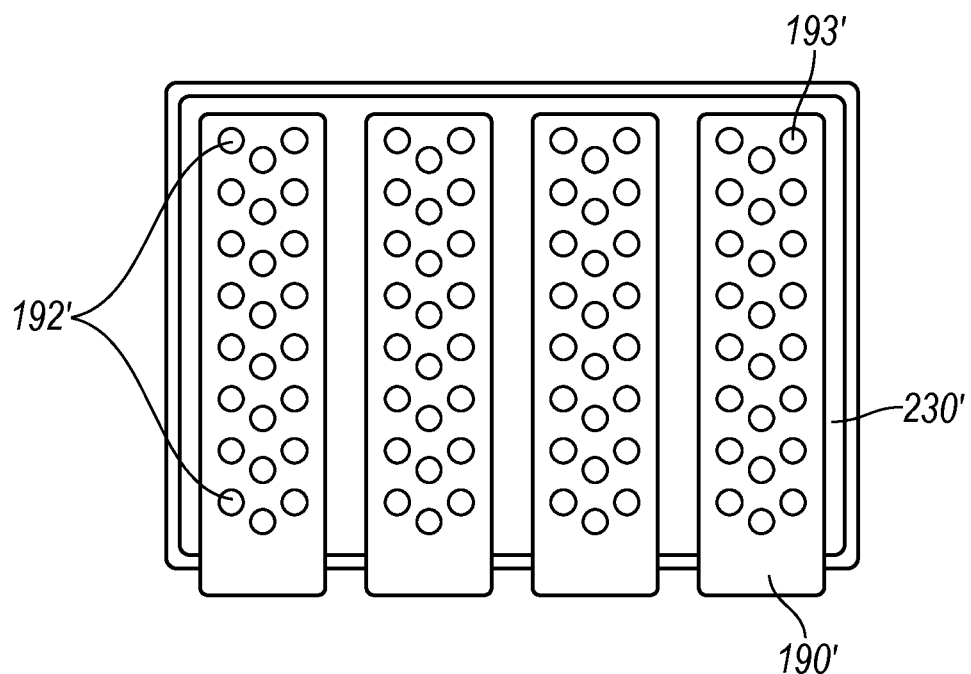

In one variation, the assay strip holder 230 is not configured to facilitate cooling of molecular diagnostic reagents within the assay strips 190; however, in another variation as shown in FIG. 21A, the assay strip holder 230 may be further configured to couple to an aluminum block 235 coupled to a set of Peltier units 236 configured to facilitate cooling of molecular diagnostic reagents within the assay strips 190. Additionally, the assay strip holder 230 may be configured to be received and carried by an assay strip carrier 240, which, as shown in FIG. 20, functions to facilitate handling and alignment of multiple assay strip holders 230. In a specific example, as shown in FIG. 19, the assay strip holder 230 has dimensions of 127.76 mm×85.48 mm×14.35 mm, complies with American National Standards Institute (ANSI) and Society for Laboratory Automation and Screening (SLAS) standards, and is configured to hold six 16-well assay strips for a total of 96 wells 193. In another specific example, as shown in FIG. 21B, the assay strip holder 230' is configured to hold four assay strips 190', each comprising 24 wells 193' for a total of 96 wells per assay strip holder 230'. Other combinations of the described embodiments, variations, and examples of the assay strip 190, assay strip holder 230, and assay strip carrier 240 may be incorporated into embodiments of the system 100 for processing and detecting nucleic acids.

1.4 System—Microfluidic Cartridge

The microfluidic cartridge 210 functions to receive a set of magnetic bead-samples, facilitate separation of nucleic acids from the set of magnetic bead-samples, receive a set of nucleic acid-reagent samples, and facilitate analysis of nucleic acids from the set of nucleic acid-reagent samples.

In one embodiment, the microfluidic cartridge 210 comprises a top layer 211 including a set of sample port-reagent port pairs 212 and a set of detection chambers 213; an intermediate substrate 214, coupled to the top layer 211 and partially separated from the top layer 211 by a film layer 215, configured to form a waste chamber 216; an elastomeric layer 217 partially situated on the intermediate substrate 214; a magnet housing region 218 accessible by a magnet 160 providing a magnetic field; and a set of fluidic pathways 219, each formed by at least a portion of the top layer 211, a portion of the film layer 215, and a portion of the elastomeric layer 217. In the embodiment, the microfluidic cartridge 10 further comprises a bottom layer 221 coupled to the intermediate substrate 214 and configured to seal the waste chamber 216. Furthermore, in the embodiment, the top layer 211 of the microfluidic cartridge 210 further comprises a shared fluid port 222, a vent region 223, and a heating region 224, such that each fluidic pathway 220 in the set of fluidic pathways 219 is fluidically coupled to a sample port-reagent port pair 224, the shared fluid port 222, the waste chamber 216, and a detection chamber 225, comprises a turnabout portion 226 configured to pass through the heating region 224 and the magnetic field, and is configured to pass through the vent region 223 upstream of the detection chamber 225. Each fluidic pathway 220 thus functions to receive and facilitate processing of a sample fluid containing nucleic acids as it passes through different portions of the fluidic pathway 220.

The microfluidic cartridge 210 is preferably configured to be received and manipulated by the molecular diagnostic module 130, such that the cartridge receiving module 140 of the molecular diagnostic module 130 receives and aligns the microfluidic cartridge 210 within the molecular diagnostic module 130, the heating and cooling subsystem 150 of the molecular diagnostic module 130 is configured to transfer heat to the heating region 224 of the microfluidic cartridge 210, and the magnet 160 of the molecular diagnostic module 130 is configured to be received by the magnet housing region 218 of the microfluidic cartridge 210 to provide a magnetic field for separation of nucleic acids. Additionally, the shared fluid port 222 of the microfluidic cartridge 210 is configured to couple to a nozzle 149 coupled to the linear actuator 146 of the cartridge receiving module 140, such that the liquid handling system 250 can deliver fluids and gases through the shared fluid port 222. The elastomeric layer 217 of the microfluidic cartridge 210 is also preferably configured to be occluded at a set of occlusion positions 226 by the valve actuation subsystem 170 of the molecular diagnostic module, in order to occlude portions of a fluidic pathway 220 of the microfluidic cartridge 210 for processing of a set of biological samples. The optical subsystem 180 of the molecular diagnostic module 130 is further configured to align with the set of detection chambers 213 of the microfluidic cartridge 210, to facilitate analysis of a set of nucleic acid samples. The microfluidic cartridge 210 is preferably the microfluidic cartridge 210 described in U.S. application Ser. No. 13/765,996, which is incorporated in its entirety by this reference, but may alternatively be any appropriate cartridge or substrate configured to receive and process a set of samples containing nucleic acids.

1.5 System—Fluid Handling System and Filter

Figure 14A:
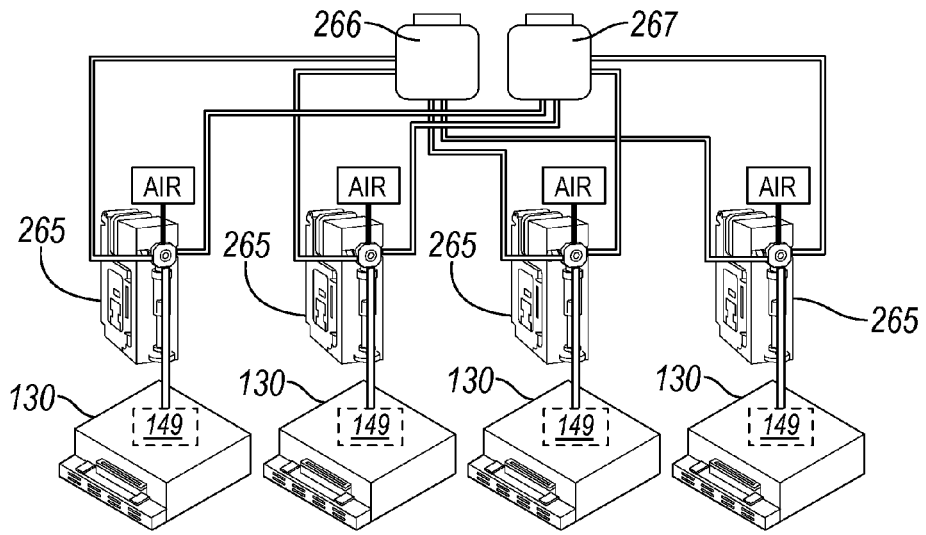
FIGS. 14A-14C depict an embodiment of a fluid handling system of a system for processing and detecting nucleic acids.
Figure 14B:
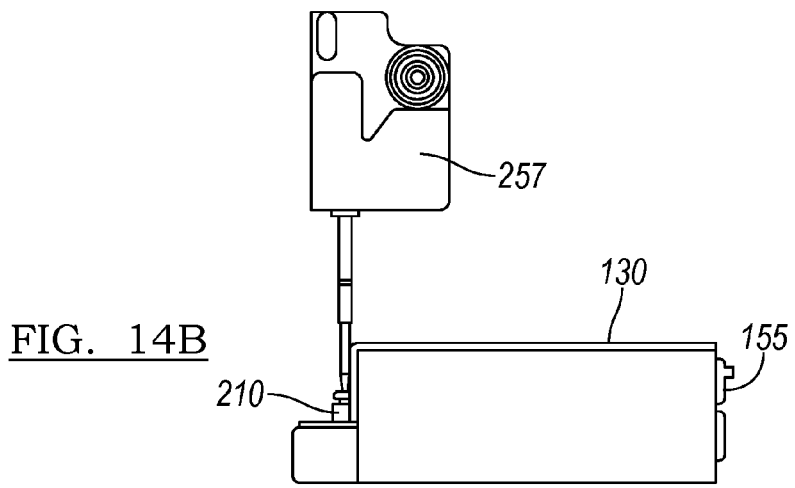
Figure 14C:
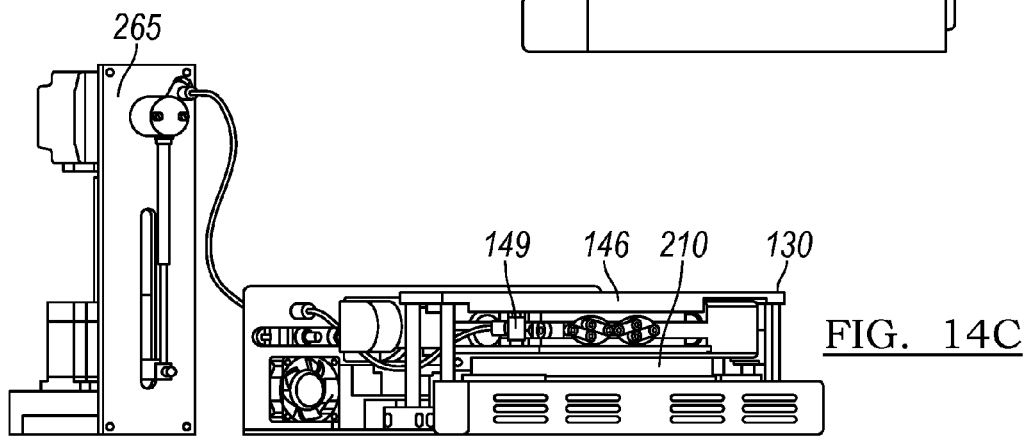

The liquid handling system 250 of the system 100 includes a liquid handling arm 255 and a syringe pump 265, as shown in FIGS. 14A-14C and functions to deliver biological samples, reagents, and gases to elements of the system 100. As described in Section 1, an embodiment of the liquid handling system 250 is configured to aspirate a set of biological samples containing nucleic acids (i.e., impure nucleic acid samples), dispense the set of biological samples into a capture plate 110 to be lysed and combined with magnetic beads by a capture plate module 120, aspirate the set of biological samples combined with magnetic beads (i.e., set of magnetic bead-samples) from the capture plate 110, and dispense the set of magnetic bead-samples into microfluidic cartridge 210 located in a molecular diagnostic module 130. The embodiment of the liquid handling system 100 is further configured to facilitate separation of a set of nucleic acids from the magnetic bead-samples, by dispensing a wash solution, a release solution, and/or air into the molecular diagnostic module 130, by the nozzle 149 coupled to the linear actuator 146, at appropriate stages, aspirate the set of nucleic acids from the molecular diagnostic module 130, combine the set of nucleic acids with a set of molecular diagnostic reagents using an assay strip 190, and dispense the set of nucleic acids combined with the set of molecular diagnostic reagents (i.e., set of nucleic acid-reagent mixtures) into the molecular diagnostic module 130 for further processing and analysis. [Other embodiments of the liquid handling system 250 may be configured to perform alternative molecular diagnostic assay protocols and/or dispense and aspirate alternative fluids into and from other elements supporting a molecular diagnostic protocol.

The liquid handling arm 255 comprises a gantry 256 and a multichannel liquid handling head 257, and functions to travel to different elements of the system 100 for fluid delivery and aspiration. The liquid handling arm 255 is preferably automated and configured to move, aspirate, and deliver fluids automatically, but may alternatively be a semi-automated liquid handling arm 255 configured to perform at least one of moving, aspirating, and delivering automatically, while another entity, such as a user, performs the other functions.

The gantry 256 is coupled to the multichannel liquid handling head 257, and functions to transport the multichannel liquid handling head 257 to different elements of the system 100 for fluid delivery and aspiration. Preferably, the gantry 256 is automated and configured to translate the multichannel liquid handling head 257 within at least two dimensions, and provides X-Y positional accuracy of at least 0.5 mm. Additionally, in the orientation shown in FIG. 14B, the gantry is preferably situated above the molecular diagnostic module 130, such that the gantry 256 can translate within at least two dimensions without interfering with other elements of the system 100. Alternatively, the gantry 256 may be any appropriate gantry 256 to facilitate movement of an end effector within at least two dimensions, as is readily known by those skilled in the art.

Figure 15:
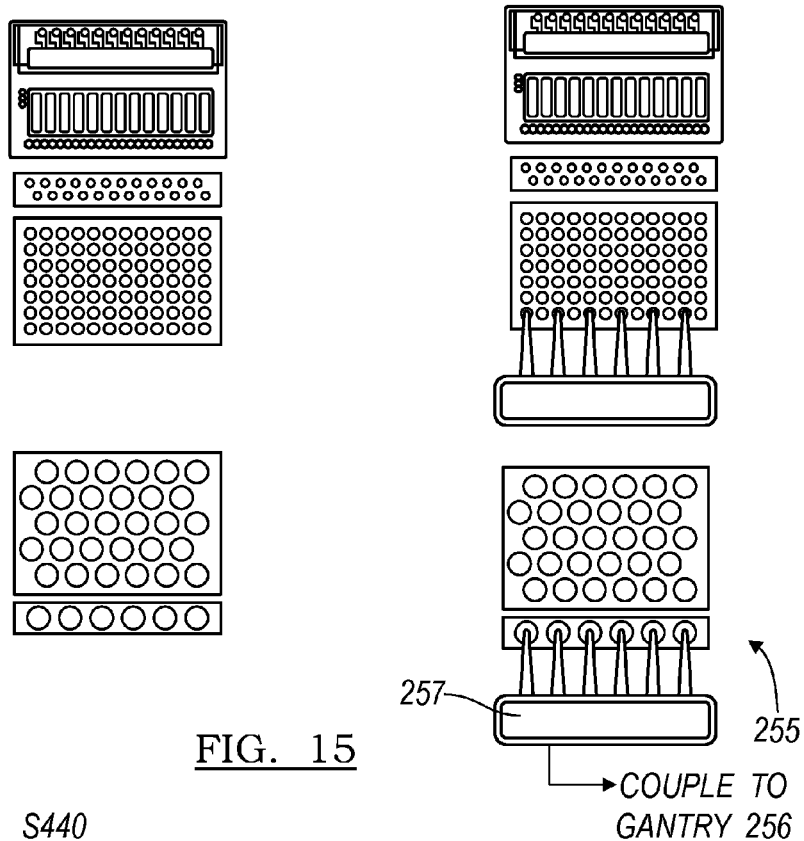
FIG. 15 depicts embodiments of elements of the fluid handling system.

The multichannel liquid handling head 257 functions to aspirate fluids from and deliver fluids to different elements of the system 100. Preferably, the multichannel liquid handling head 257 is a multichannel pipette head; however, the multichannel liquid handling head 257 may alternatively be any appropriate multichannel liquid handling head configured to deliver fluids and/or gases. Preferably, the multichannel liquid handling head 257 comprises at least eight independent channels 258, but may alternatively comprise any number of channels 258 configured to aspirate and deliver fluids. The channel-to-channel pitch is preferably variable, and in a specific example ranges between 9 mm and 36 mm; however, the channel-to-channel pitch may alternatively be fixed, as shown in FIG. 15. The multichannel liquid handling head 257 also preferably provides independent z-axis control (in the orientation shown in FIG. 14B), such that, in combination with the gantry 256. The multichannel liquid handling head 257 is preferably configured to couple to both large (e.g., 1 mL) and small (e.g., between 100 and 300 μL) pipette tips, and in a specific example, has a precision of at least 6% using small disposable pipette tips and a precision of at least 2% using large disposable pipette tips when dispensing essentially the entire tip volume. Alternatively, the multichannel liquid handling head 257 may be configured to couple to any object configured to facilitate aspiration and delivery of fluids. Preferably, the multichannel liquid handling head 257 provides independent control of the channels 258, with regard to volumes of fluid aspirated or delivered, fluid dispensing rates, and/or engaging and disengaging pipette tips. Alternatively, the multichannel liquid handling head 257 may not provide independent control of the channels 258, such that all channels 258 of the multichannel liquid handling head 257 are configured to perform identical functions simultaneously. Preferably, the multichannel liquid handling head 257 is configured to aspirate and deliver both liquids and gases, but alternatively, the multichannel liquid handling head 257 may be configured to only aspirate and deliver liquids. Preferably, the multichannel liquid handling head 257 provides at least one of liquid level detection, clot detection, and pipette tip engaging/disengaging detection for each of the channels 258; however, the multichannel liquid handling head 257 may alternatively not provide liquid level detection, clot detection, and pipette tip engaging/disengaging detection for each of the channels 258.

In one embodiment, the multichannel liquid handling head 257 is configured to couple to at least one filter 260, which functions to pre-filter liquids being aspirated and/or dispensed by the liquid handling arm 255, and is preferably a custom filter 260 configured to couple to a pipette tip, but may alternatively be any appropriate filter configured to couple to the liquid handling arm 255 and filter liquids being aspirated and/or dispensed by the liquid handling arm 255.

Figure 22:
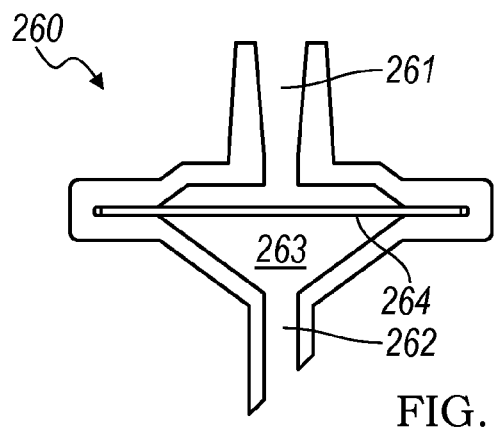
FIG. 22 shows an embodiment of a filter to facilitate processing and detecting of nucleic acids.

An embodiment of a custom filter 260, as shown in FIG. 22, comprises a first end 261 configured to couple to a pipette tip, a pointed second end 262, a void 263 coupled to the first end 261 and the pointed second end 262, and a filter membrane 264 subdividing the void 263. The first end 261, as shown in FIG. 22, preferably comprises a tapered channel configured to provide a friction fit with a pipette tip; however, the first end may alternatively not comprise a tapered channel and may be configured to couple to a pipette tip using any appropriate means. The pointed second end 262 is preferably sharp and configured to pierce an object, such as a foil seal; additionally, the pointed second end 262 is preferably at least as long as required to dispense into a well 113 of the capture plate 110. The void 263 preferably defines a conical region defined by the filter membrane 264, wherein the conical region is configured to divert a fluid within the filter 260 toward the pointed second end 262; however, the void 263 may not include a conical region. The filter membrane 264 functions to filter a fluid aspirated by the multichannel liquid handling head 257, and is configured to subdivide the void 263 to define a conical region; however, the filter membrane 264 may alternatively not define a conical region of the void 263. In one embodiment, in the orientation shown in FIG. 22, the region of the void 263 below the filter membrane 264 may have a volumetric capacity of between 200 ul and 1 mL; however, the region of the void 263 below the filter membrane may alternatively have any appropriate volumetric capacity.

Figure 23:
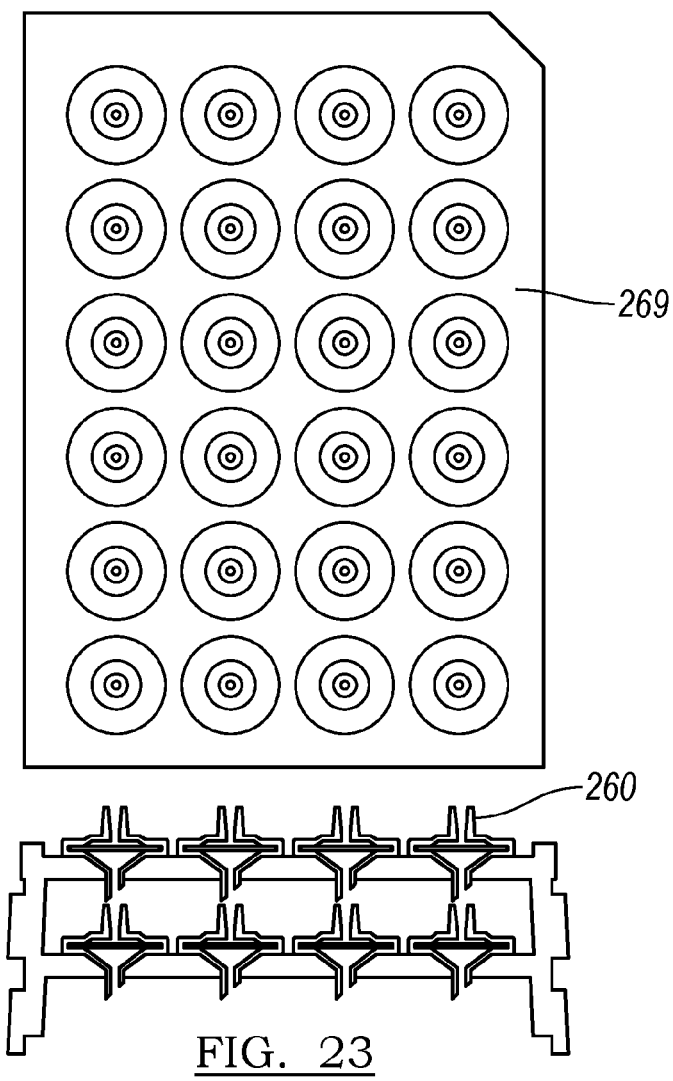
FIG. 23 shows an embodiment of a filter holder to facilitate processing and detecting of nucleic acids.
Figure 24A:
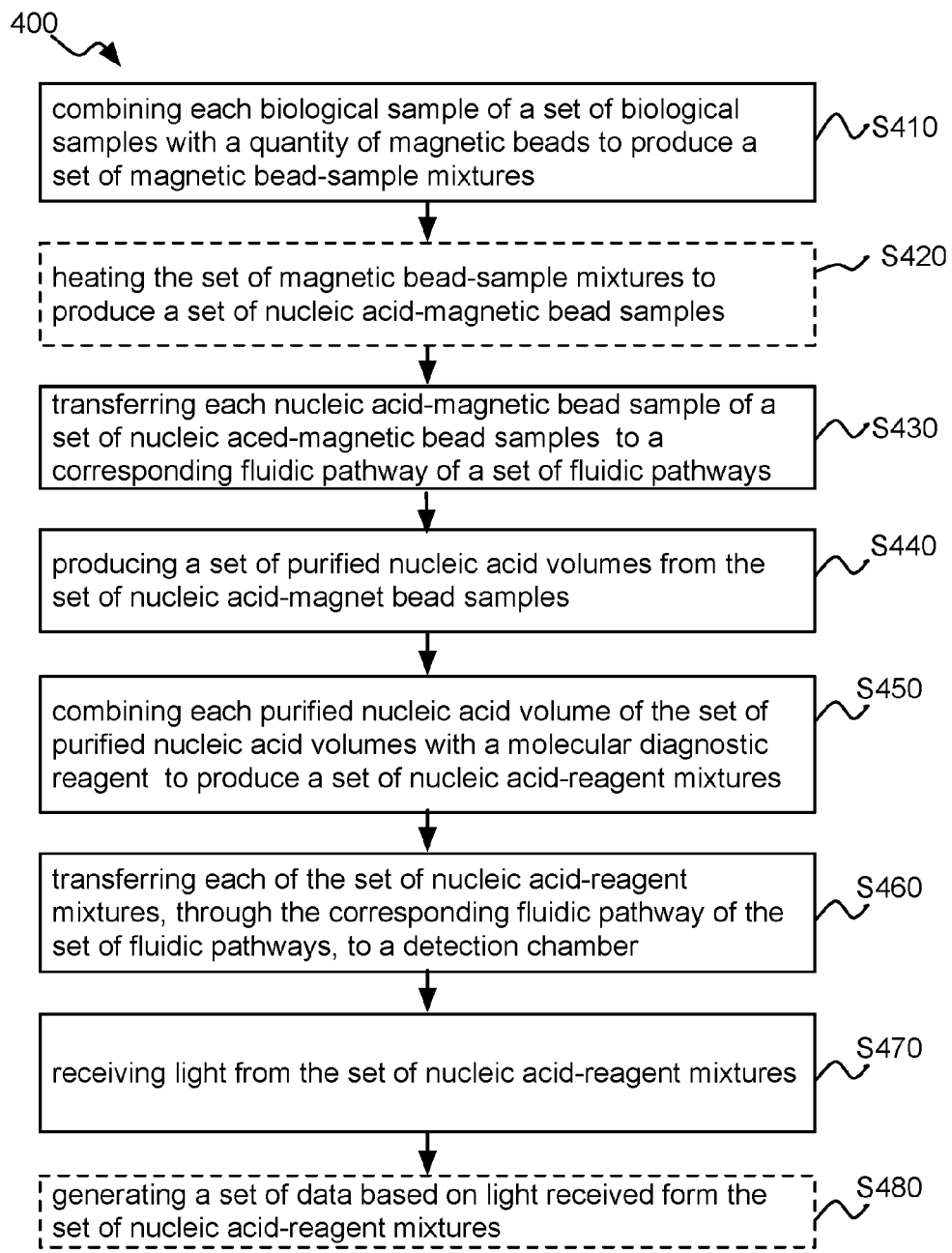
FIGS. 24A-24D depict embodiments of a method for processing and detecting nucleic acids.
Figure 24B:
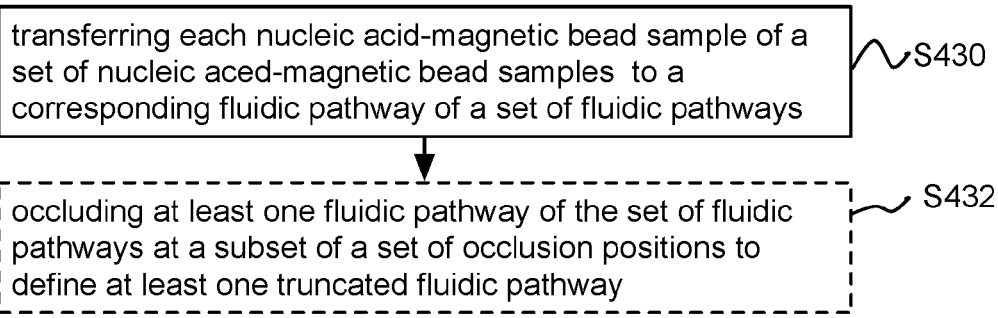
Figure 24C:
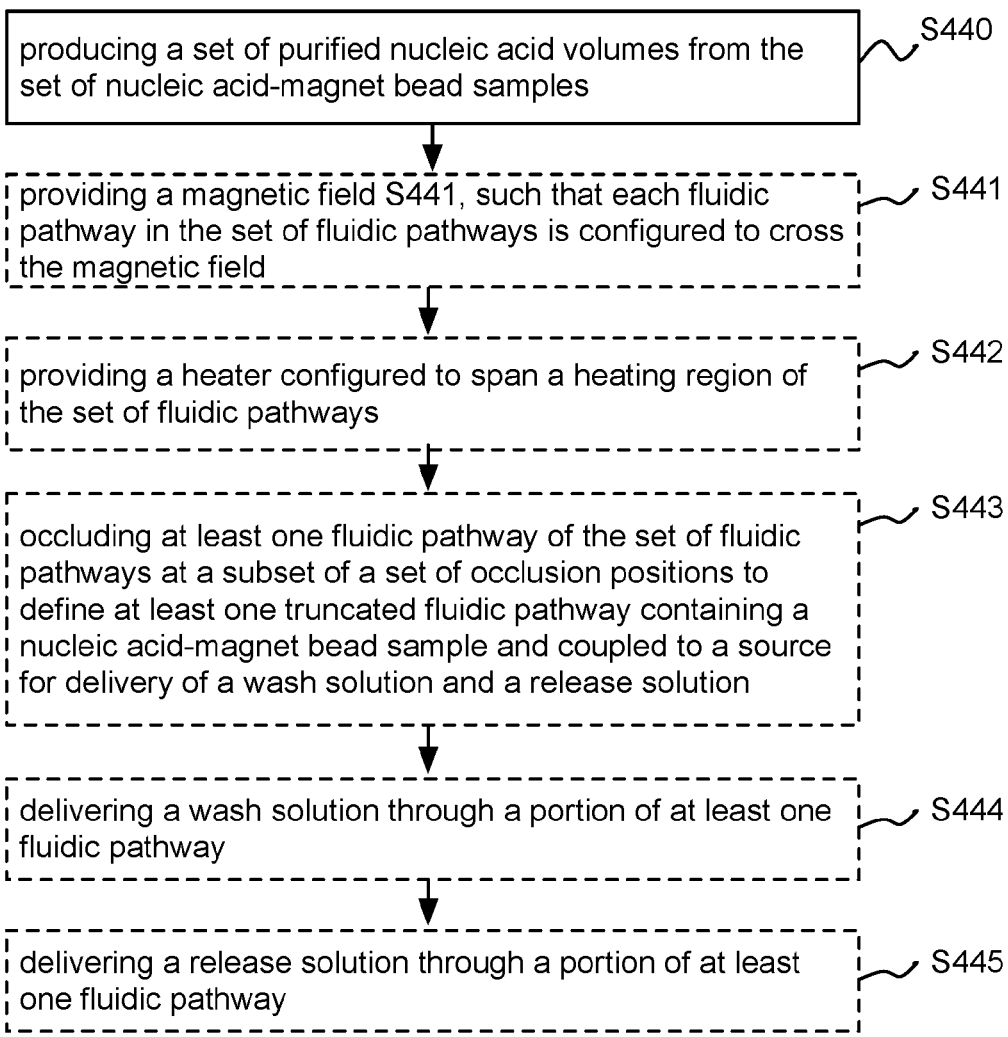
Figure 24D:
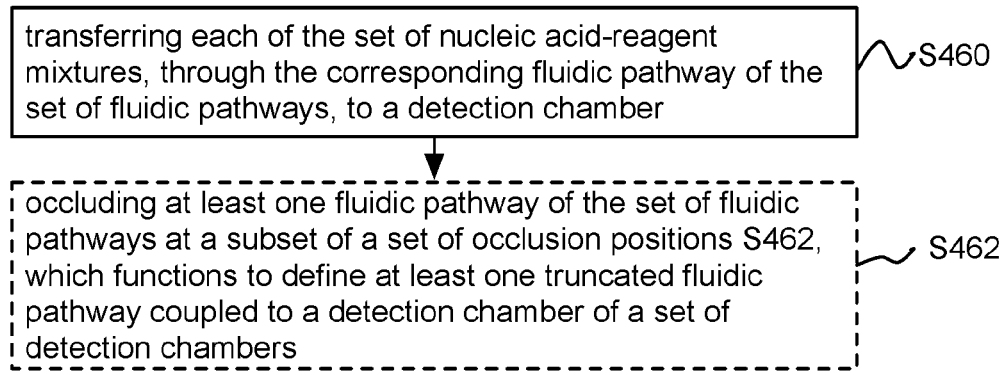

A set of filters 260 may further be configured to be received and delivered by a filter holder 269, as, shown in FIG. 23. A specific embodiment of a filter holder 269 comprises a set of 24 tapered holes with an 18 mm center-to-center pitch, arranged in six rows of four holes. The specific embodiment of the filter holder 269 is also compliant with ANSI and SLAS standards, has dimensions of 127.75×85.5×14.35 mm, and is stackable with other specific embodiments of the custom filter holder 269. Alternatively, the filter holder 269 may be any appropriate filter holder 269 configured to receive and deliver a set of filters 260, as is readily known by those skilled in the art.

1.5.1 Fluid Handling System—Syringe Pump

The syringe pump 265 of the liquid handling system 250 is coupled to a wash solution source 266, a release solution source 267, a source of air 268, and flexible tubing 291, and functions to deliver a wash solution, a release solution, and air through a valve to the molecular diagnostic module 130 to facilitate isolation and purification of nucleic acids from a set of magnetic bead-samples. The flexible tubing 291 is preferably coupled at a first end to the syringe pump, and at a second end to a nozzle 149 coupled to the linear actuator 146 of the molecular diagnostic module 130, as shown in FIG. 14C. As stated earlier, an extended configuration 146b of the linear actuator 146 is configured to couple the nozzle 149 to a fluid port 222 of a microfluidic cartridge 210 within the molecular diagnostic module 130, such that the wash solution, release solution, and air can be delivered to the microfluidic cartridge 210 at appropriate stages. A specific embodiment of the syringe pump 265 comprises a 4-way valve, is able to pump 20-5000 μL of fluids or air through the 4-way valve at flow rates from 50-500 μL/min, can couple to syringes with between 1 mL and 10 mL capacities, and has a precision of at least 5% with regard to fluid or air delivery. Alternatively, the syringe pump 265 may be any appropriate syringe pump 265 or fluid delivery apparatus configured to deliver a wash solution, a release solution, and air to the molecular diagnostic module 130, as is readily known by those skilled in the art.

1.6 System—Additional Elements

The system 100 may further comprise a tag reader 271, which functions to read barcodes, QR codes and/or any other identifying tags of the system 100. Preferably, the tag reader 271 is coupled to the liquid handling system 250, such that the tag reader 271 is configured to read tags on puncturable foil seals 115, 195 or tags located on any element of the system 100 accessible by the liquid handling system 250; however, the tag reader 271 may alternatively not be coupled to the liquid handling system 250. In one alternative embodiment of the system 100, the tag reader 271 may be a standalone unit that is configured to be manipulated by a user to scan tags or labels located on elements of the system 100.

The system 100 may also further comprise a controller 272 coupled to at least one of the capture plate module 120, the molecular diagnostic module 130, the liquid handling system 250, and the tag reader 271, and functions to facilitate automation of the system 100. In a variation wherein the controller 272 is coupled to the capture plate module 120, the controller 272 preferably functions to automate heating of a capture plate 110, which facilitates lysing of biological samples within the capture plate 110 and binding of nucleic acids within the capture plate 110 to magnetic beads 119 of the capture plate 110. In a variation wherein the controller 272 is coupled to the molecular diagnostic module 130, the controller 272 preferably functions to automate reception of a microfluidic cartridge, heating of biological samples within the molecular diagnostic module 130 and the detection chambers 213, occlusion of fluidic pathways 220 by the valve actuation subsystem 170, and analysis of a set of nucleic acid-reagent mixtures by the optical subsystem 180. In a variation wherein the controller 272 is coupled to the liquid handling system 250, the controller 272 preferably functions to automate aspiration, transfer, and delivery of fluids and/or gases to different elements of the system 100. In a variation wherein the controller 272 is coupled to the tag reader 271, the controller preferably functions to automate reading of tags by the tag reader 271, and may further function to facilitate transfer of information from the tags to a processor 273. Other variations of a controller may function automate handling, transfer, and/or storage of other elements of the system 100, such as capture plates 110, assay strips 190, assay strip holders 230, assay strip carriers 240, filters 200, filter holders 205, and/or microfluidic cartridges 210, using a robotic arm or gantry similar to that used in the liquid handling system 250. Alternative combinations of the above variations may involve a single controller 272, or multiple controllers configured to perform all or a subset of the functions described above.

The system 100 may also further comprise a processor 273, which functions to receive and process information from a tag reader 271, and also to receive and process data received from the optical subsystem 180 of the molecular diagnostic module 130. Preferably, the processor 273 is coupled to a user interface 274, which functions to display processed and/or unprocessed data produced by the system 100, settings of the system 100, information obtained from a tag reader 271, or any other appropriate information. Alternatively, the processor 273 is not coupled to a user interface 274, but comprises a connection 275 configured to facilitate transfer of processed and/or unprocessed data produced by the system 100, settings of the system 100, information obtained from a tag reader 271, or any other appropriate information to a device external to the system 100.

As a person skilled in the art will recognize from the previous detailed description and from the figures and claims, modifications and changes can be made the described embodiments of the system 100 without departing from the scope of the system 100.

2. Method for Processing and Detecting Nucleic Acids

An embodiment of a method 400 for processing and detecting nucleic acids from a set of biological samples comprises: combining each biological sample of the set of biological samples with a quantity of magnetic beads to produce a set of magnetic bead-sample mixtures S410; heating the set of magnetic bead-sample mixtures to produce a set of nucleic acid-magnetic bead samples S420; transferring each nucleic acid-magnetic bead sample of the set of nucleic acid-magnetic bead samples to a corresponding fluidic pathway of a set of fluidic pathways S430; producing a set of nucleic acid volumes from the set of nucleic acid-magnetic bead samples S440; combining each nucleic acid volume of the set of nucleic acid volumes with a molecular diagnostic reagent of a set of molecular diagnostic reagents to produce a set of nucleic acid-reagent mixtures S450; transferring each of the set of nucleic acid-reagent mixtures, through the corresponding fluidic pathway of the set of fluidic pathways, to a detection chamber of a set of detection chambers S460; and receiving light from the set of nucleic acid-reagent mixtures S470. The method 400 may further comprise generating a set of data based on light received form the set of nucleic acid-reagent mixtures S480. The method 400 functions to isolate and extract a set of nucleic acid volumes from a biological sample, and to facilitate analysis of the nucleic acid volumes according to at least one molecular diagnostic protocol.

Step S410 recites combining each biological sample of the set of biological samples with a quantity of magnetic beads to produce a set of magnetic bead-sample mixtures, and functions to prepare a set of biological samples to be lysed and combined with magnetic beads. For each biological sample, Step S410 preferably comprises aspirating a portion of the volume of the biological sample from a sample container (possibly containing an aqueous solution prior to addition of biological sample), and transferring the portion of the biological sample to a well containing a set of magnetic beads. Alternatively, for each biological sample, Step S410 may comprise aspirating the entire volume of the biological sample from a sample container, and transferring the volume of the biological sample to be combined with a set of magnetic beads. Preferably, all biological samples in the set of biological samples are aspirated and combined with the magnetic beads in the wells simultaneously using a multichannel fluid delivery system; however, all biological samples in the set of biological samples may alternatively be aspirated and combined with a set of magnetic beads non-simultaneously. The magnetic beads are preferably polymer beads, precoupled with a ligand for binding to a nucleic acid, and comprising a superparagmagnetic component. Additionally, the magnetic beads may be treated to be positively charged. However, the magnetic beads may alternatively be any appropriate magnetic beads configured to facilitate biomagnetic separation.

In addition to combination with magnetic beads, Step 410 may further include combining each biological sample of the set of biological samples with a lysing enzyme (e.g. proteinase K), and a sample process control comprising two or more nucleic acid sequences (i.e., one for DNA and one for RNA) to be included with each sample. This allows biological samples to effectively lysed, which releases waste components into a wash solution, and allows nucleic acids to bind to magnetic beads. This additionally allows the sample process control to be later detected, as a check to verify the accuracy of a molecular diagnostic assay being performed.

Figure 16A:
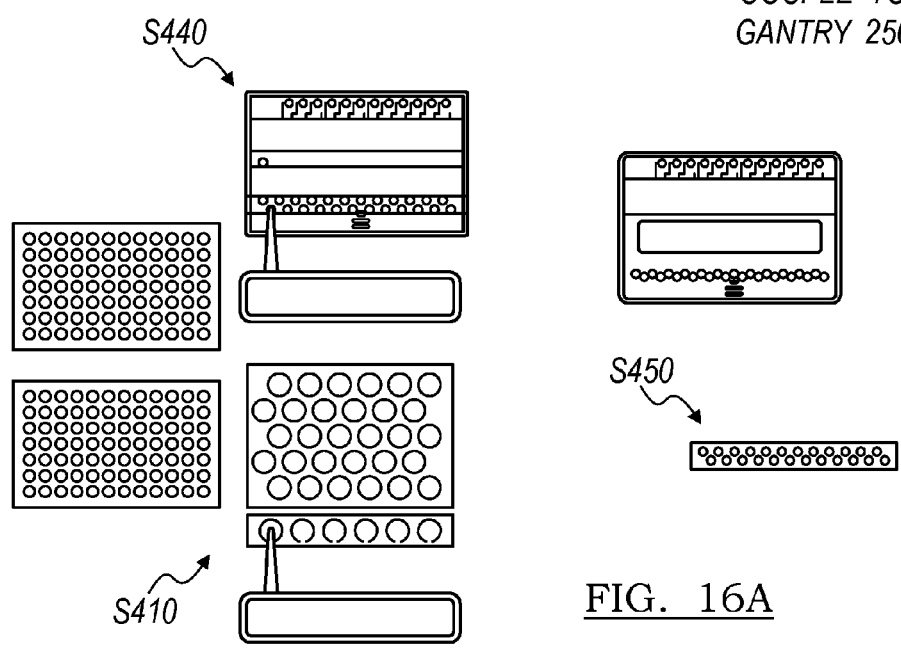
FIGS. 16A-16C are schematics depicting example methods for processing and detecting nucleic acids.
Figure 16B:
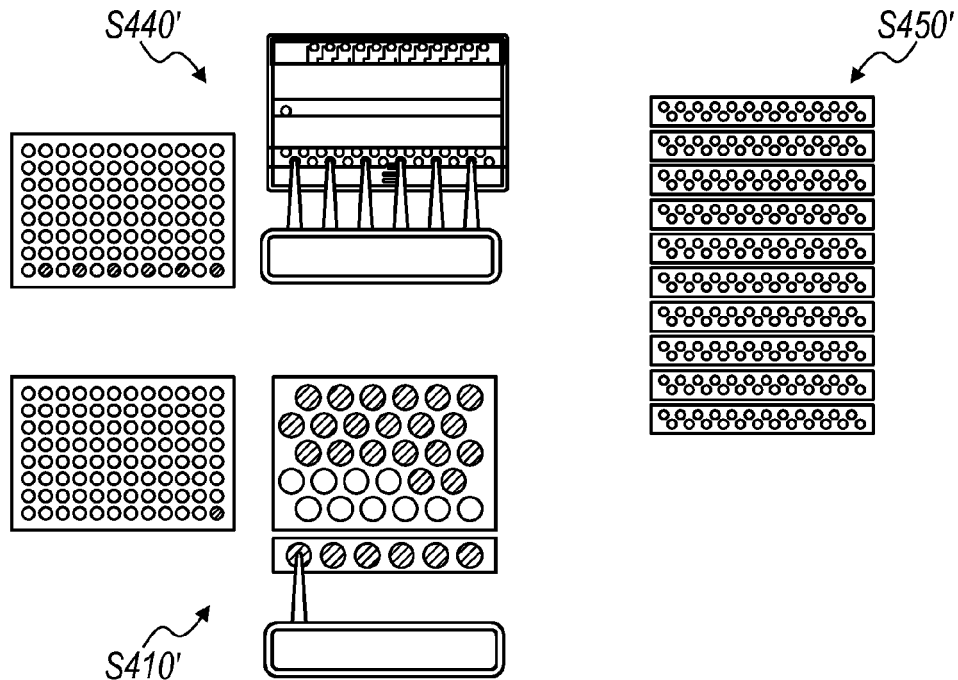
Figure 16C:
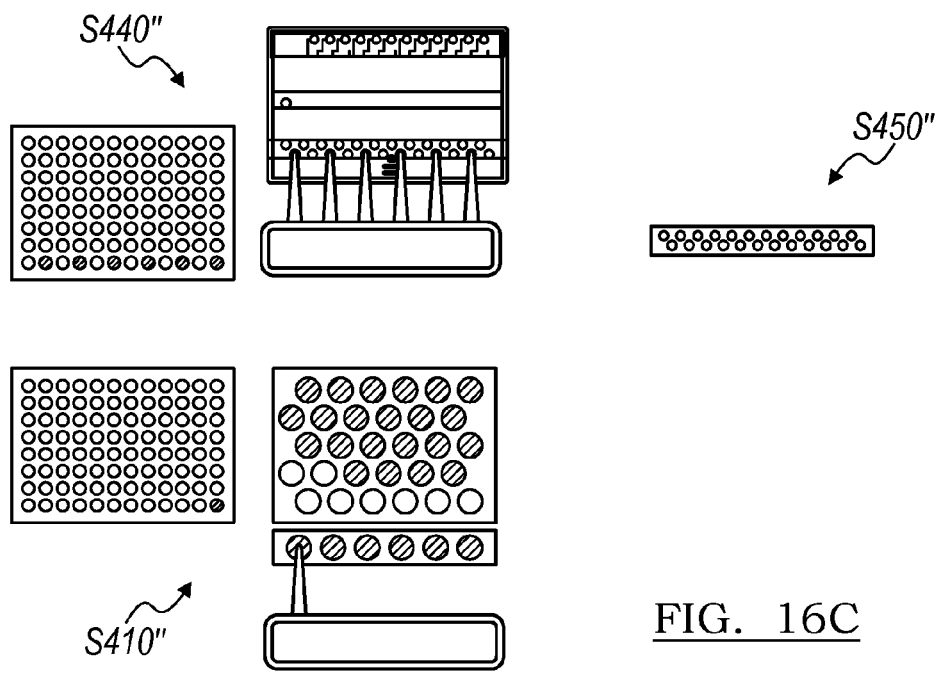

In a first variation of Step S410 for one biological sample, as shown in FIG. 16A, a volume of the biological sample is aspirated and combined with a set of magnetic beads. In the first variation of Step S410, a set of different biological samples may thus be aspirated simultaneously, and each biological sample may be transferred to an individual well to be combined with a set of magnetic beads to produce a set of magnetic bead-sample mixtures. In the first variation of Step S410, all magnetic bead-sample mixtures in the set of magnetic bead-sample mixtures are substantially non-identical in composition. In a second variation of Step S410, as shown in FIG. 16B, a volume of a stock biological sample is aspirated, and portions of the volume of the stock biological sample are transferred to multiple wells to be combined with multiple sets of magnetic beads to produce a set of magnetic bead-sample mixtures. In the second variation of Step S410, all magnetic bead-sample mixtures in the set of magnetic bead-sample mixtures are substantially identical in composition. Other variations of Step S410 may comprise filtering at least one biological sample of the set of biological samples S415 prior to combining each biological sample of the set of biological samples with a quantity of magnetic beads.

In a specific example of Step S410, a multichannel liquid handling system aspirates approximately 1 mL of each of a set of biological samples in aqueous buffer using a set of 1 mL pipette tips, couples each of the pipette tips to a custom 13 mm diameter filter, punctures a foil seal 115 of a capture plate at a set of wells, wherein each well of the set of wells contains a set of magnetic beads, and dispenses each aspirated volume of a biological sample into a well of the capture plate containing a set of magnetic beads, and disposes of the tip/filter combination. In the specific example of Step S410, the multichannel liquid handling system then picks up new disposable tips and aspirates and dispenses the contents of each well at least three times to mix the contents, and then disposes of the set of pipette tips and filters.

Step S420 recites heating the set of magnetic bead-sample mixtures to produce a set of nucleic acid-magnetic bead samples, and functions to incubate the set of magnetic bead-sample mixtures in order to lyse biological matter, and release nucleic acids to be bound to magnetic beads. Preferably, Step S420 comprises heating a capture plate containing the set of magnetic bead-sample mixtures for a specified amount of time at a specified temperature, and may additionally include cooling the set of magnetic bead-sample mixtures. In a specific example, Step S420 comprises heating a capture plate containing the set of magnetic bead-sample mixtures using a capture plate module, wherein the capture plate module is configured to cradle and controllably heat wells containing the set of magnetic bead-sample mixtures. Step S420 may alternatively comprise incubating the set of magnetic bead-sample mixtures using any appropriate method and/or system as is known by those skilled in the art. Finally, Step S420 may be omitted in embodiments of the method 400 involving samples that do not require heating.

Step S430 recites transferring each nucleic acid-magnetic bead sample of the set of nucleic acid-magnetic bead samples to a corresponding fluidic pathway of a set of fluidic pathways, and functions to isolate each of the set of nucleic acid-magnetic bead samples within separate pathways for further processing. Preferably, all nucleic acid-magnetic bead samples in the set of nucleic acid-magnetic bead samples are transferred simultaneously to the set of fluidic pathways, but alternatively, each nucleic acid-magnetic bead sample in the set of magnetic bead-samples may be transferred to a corresponding fluidic pathway independently of the other nucleic acid-magnetic bead samples. In addition, preferably the entire volume, or substantially all of the volume, of the nucleic acid-magnetic bead sample is transferred to the set of fluidic pathways, without magnetically isolating magnetic beads and removing supernatant fluids prior to transferring each nucleic acid-magnetic bead sample of the set of nucleic acid-magnetic bead samples to a corresponding fluidic pathway of a set of fluidic pathways.

Step S430 may further comprise occluding at least one fluidic pathway of the set of fluidic pathways at a subset of a set of occlusion positions S432, which functions to define at least one truncated fluidic pathway. Preferably, Step S432 comprises defining at least one truncated fluidic pathway passing through at least one of a heating region and a magnetic field; however, Step S432 may alternatively not comprise defining a truncated fluidic pathway passing through at least one of a heating region and a magnetic field.

In a specific example of Step S430, the multichannel liquid handling subsystem of Step S410 transfers a set of nucleic acid-magnetic bead samples to a set of fluidic pathways of a microfluidic cartridge aligned within a molecular diagnostic module, wherein the microfluidic cartridge comprises an elastomeric layer in contact with the set of fluidic pathways. Manipulation of the elastomeric layer at a subset of a set of occlusion positions by a valve actuation subsystem of the molecular diagnostic module defines a set of truncated fluidic pathways crossing a heating region and a magnetic field, such that each nucleic acid-magnetic bead sample in the set of nucleic acid-magnetic bead samples is isolated within a truncated fluidic pathway of the set of truncated fluidic pathways.

Step S440 recites producing a set of nucleic acid volumes from the set of nucleic acid-magnetic bead samples, and functions to separate nucleic acid volumes from the set of nucleic acid-magnetic bead samples. Step S440 preferably reduces a concentration of unwanted matter from the set of biological samples being processed, to an acceptable level; however, Step S440 may alternatively entirely remove substantially all unwanted substances from the set of biological samples being processed. Step S440 preferably includes providing a magnetic field S441, such that each fluidic pathway in the set of fluidic pathways is configured to cross the magnetic field. Preferably, the set of nucleic acid-magnetic bead samples is captured and isolated within portions of the set of fluidic pathways crossing the magnetic field. Step S440 may further comprise providing a heater configured to span a heating region of the set of fluidic pathways S442, but may alternatively comprise providing multiple heaters or altogether omit providing a heater. In embodiments wherein multiple heaters are provided, each heater is preferably independent to allow independent control of heating time and temperature for each sample. Step S442 functions to provide a heater, which, in combination with a release solution that provides a pH shift, facilitate a rapid and efficient unbinding of the nucleic acids from magnetic beads.

Step S440 may further comprise occluding at least one fluidic pathway of the set of fluidic pathways at a subset of a set of occlusion positions S443 (and opening a previously occluded channel), which functions to define at least one truncated fluidic pathway containing a nucleic acid-magnet bead sample and coupled to a source for delivery of a wash solution and a release solution. Preferably, Step S443 comprises defining at least one truncated fluidic pathway coupled to a waste chamber and to a fluid port, which functions to facilitate washing of at least one nucleic acid-magnetic bead sample in the set of nucleic acid-magnetic bead samples, and releasing of at least one nucleic acid volume from the set of nucleic acid-magnetic bead samples. Step S440 may additionally comprise delivering a wash solution through a portion of at least one fluidic pathway S444, such as the truncated fluidic pathway defined in Step S443, and delivering a release solution through a portion of at least one fluidic pathway S445, such as the truncated fluidic pathway defined in Step S443. Step S444 functions to wash at least one nucleic acid-magnetic bead sample in the set of nucleic acid-magnetic bead samples, and Step S445 functions to release at least one nucleic acid volume from the set of nucleic acid-magnetic bead samples. The heater provided in Step S442 may be activated after Step S445 to induce a pH shift.

In a specific example of Step S440, the set of fluidic pathways containing a set of nucleic acid-magnetic bead samples, from the specific example of Step S430, is occluded at a subset of the set of occlusion positions by a valve actuation subsystem of the molecular diagnostic module, to define a set of truncated fluidic pathways coupled to a waste chamber and to a shared fluid port of the microfluidic cartridge for delivery of a wash solution and a release solution. The liquid handling system delivers a wash fluid through the shared fluid port to wash the set of nucleic acid-magnetic bead samples, captured within the magnetic field, and then delivers a release fluid through the shared fluid port to release a set of nucleic acid volumes from the set of nucleic acid-magnetic bead samples. In the specific example, each fluidic pathway is washed sequentially, and the release solution is delivered to each fluidic pathway sequentially to ensure that each lane is provided with substantially equal amounts of wash and release solutions. All waste fluid produced in the specific example of Step S440 pass into the waste chamber coupled to the set of truncated fluidic pathways.

Step S450 recites combining each nucleic acid volume of the set of nucleic acid volumes with a molecular diagnostic reagent of a set of molecular diagnostic reagents to produce a set of nucleic acid-reagent mixtures, which functions to prepare the set of nucleic acid volumes to be detected. For each nucleic acid volume in the set of nucleic acid volumes, Step S450 preferably comprises aspirating an entire volume of the nucleic acid volume from its corresponding fluidic pathway, and transferring the nucleic acid volume to a well containing a molecular diagnostic reagent. Preferably, all nucleic acid volumes in the set of nucleic acid volumes are aspirated and combined with molecular diagnostic reagents simultaneously using a multichannel fluid delivery system; however, each nucleic acid volume in the set of nucleic acid volumes may alternatively be aspirated and combined with molecular diagnostic reagents independently of the other nucleic acid volumes. The molecular diagnostic reagents preferably comprise reagents configured to analyze the set of nucleic acid volumes for markers of at least one of gonorrhea (GC), Chlamydia (CT), herpes simplex virus (HSV), human immunodeficiency virus (HIV), human respiratory diseases, vaginal diseases, hepatitis C virus (HCV), hepatitis B virus (HBV), trichonomas, group B streptococcus (GBS), factor 2 (FII) gene, and factor five (FV) gene, but may alternatively comprise reagents used to detect any specific nucleic acid sequence.

In a first variation of Step S450 as shown in FIG. 16A, a nucleic acid volume is aspirated and combined with a molecular diagnostic reagent for a single assay. In the first variation of Step S450, a set of nucleic acid volumes may thus be aspirated simultaneously, and each nucleic acid volume may be transferred to an individual well to be combined with a molecular diagnostic reagent of a set of molecular diagnostic reagents to produce a set of nucleic acid-reagent mixtures. In the first variation of Step S450, all nucleic acid-reagent mixtures in the set of nucleic acid-reagent mixtures may or may not be substantially identical in composition, depending on the homogeneity of the biological samples used in Step S410; however, the first variation of S450 preferably comprises using identical molecular diagnostic reagents, such that identical molecular diagnostic protocols analyzing identical markers may be performed. Thus, the first variation of Step S450 encompasses running multiple identical tests from a stock biological sample (e.g., a multiplex assay), and running identical tests using a set of substantially different biological samples (e.g., from different sources).

In a second variation of Step S450, as shown in FIG. 16B, the set of nucleic acid volumes is aspirated, and each nucleic acid volume in the set of nucleic acid volumes is combined with a molecular diagnostic reagent of a set of molecular diagnostic reagents. In the second variation of Step S450, the set of molecular diagnostic reagents preferably comprises different molecular diagnostic reagents, such that different molecular diagnostic protocols analyzing different markers may be performed. Thus, the second variation encompasses running multiple substantially different tests using a stock biological sample, and running substantially different tests using substantially different biological samples (e.g., from different sources)

In a specific example of Step S450, a multichannel liquid handling system aspirates approximately 18 µL of each of a set of nucleic acid volumes from the microfluidic cartridge used in the specific example of Step S440 using a set of pipette tips, punctures at least one foil seal 195 of at least one assay strip, wherein each well of the at least one assay strip contains molecular diagnostic reagents, and dispenses each aspirated nucleic acid volume into a well of the assay strip. In the specific example of S450, the multichannel liquid handling system then aspirates and dispenses the contents of each well approximately 10 times to reconstitute molecular diagnostic reagents and mix the contents of each well.

Step S460 recites transferring each of the set of nucleic acid-reagent mixtures, through the corresponding fluidic pathway of the set of fluidic pathways, to a detection chamber of a set of detection chambers, which functions to deliver the set of nucleic acid-reagent mixtures to an isolated detection chamber for further processing and analysis. Preferably, all nucleic acid-reagent mixtures in the set of nucleic acid-reagent mixtures are transferred simultaneously to the set of fluidic pathways, but alternatively, each nucleic acid-reagent mixture in the set of nucleic acid reagent mixtures may be transferred to a corresponding fluidic pathway independently of the other nucleic acid reagent mixtures. Step S460 may further comprise occluding at least one fluidic pathway of the set of fluidic pathways at a subset of a set of occlusion positions S462, which functions to define at least one truncated fluidic pathway coupled to a detection chamber of a set of detection chambers. Preferably, Step S462 comprises occluding each fluidic pathway of the set of fluidic pathways at a subset of a set of occlusion positions, thus defining a set of truncated fluidic pathways, each coupled to a detection chamber.

In a specific example of Step S460, the multichannel liquid handling subsystem of the specific example of Step S450 transfers a set of nucleic acid-reagent mixtures, each having a volume of approximately 16 µL, back to the set of fluidic pathways of the microfluidic cartridge of the specific example of Step S450. Each nucleic acid-reagent mixture in the set of nucleic acid-reagent mixtures is transferred at a rate of 50 µL/minute. Manipulation of the elastomeric layer at a subset of a set of occlusion positions by the valve actuation subsystem of the molecular diagnostic module defines a set of truncated fluidic pathways, each coupled to a detection chamber, such that each nucleic acid-magnetic bead sample in the set of nucleic acid-magnetic bead samples is isolated within a truncated fluidic pathway of the set of truncated fluidic pathways. In the specific embodiment the occlusion position immediately upstream of the detection chamber and the occlusion position immediately downstream of the detection chamber are normally closed positions. During delivery, the multichannel liquid handling subsystem generates pressure to cause the elastomeric layer at the normally closed positions to deform and allow fluid to flow through the normally closed positions. Once the pressure drops after the detection chamber is filled and the multichannel liquid handing subsystem ceases delivery, the elastomeric layer is configured to overcome the pressure in the channel and recloses, thereby sealing the normally closed positions. The normally closed positions are then compressed using the valve actuation subsystem during thermocycling to prevent pressures generated during a molecular diagnostic assay to cause the normally closed positions to leak. After the molecular diagnostic assay is complete and the occlusion "pins" withdrawn, the normally closed positions allow the samples and amplicons to be trapped within detection chambers, substantially reducing the risk of contamination of the lab or other samples.

Step S470 recites receiving light from the set of nucleic acid-reagent mixtures, and functions to produce emission responses from the set of nucleic acid-reagent mixtures in response to transmission of excitation wavelength light or chemiluminescent effects. Preferably, Step S470 comprises the ability to transmit light including a wide range of wavelengths through a set of excitation filters and through a set of apertures configured to individually transmit light having single or multiple excitation wavelengths onto the set of nucleic acid-reagent mixtures, and receiving light through a set of emission filters, from the set of nucleic acid-reagent mixtures. Step S470 may additionally comprise reflecting light from the set of excitation filters off of a set of dichroic mirrors, and transmitting light through the set of dichroic mirrors to a set of photodetectors. A specific example of Step S470 comprises using the optical subsystem 180 of the system 100 described above to transmit and receive light; however, alternative variations of Step S470 may use any appropriate optical system configured to transmit light at excitation wavelengths toward the set of nucleic acid-reagent mixtures, and to receive light at emission wavelengths from the set of nucleic acid-reagent mixtures.

Step S480 recites generating a set of data based on light received from the set of nucleic acid-reagent mixtures, which functions to produce quantitative and/or qualitative data from the set of nucleic acid-reagent mixtures. Step S480 may further function to enable detection of a specific nucleic acid sequence from the nucleic acid-reagent mixture, in order to identify a specific nucleic acid sequence, gene, or organism. Preferably, Step S480 includes converting electrical signals, produced by a set of photodetectors upon receiving light from the set of nucleic acid-reagent mixtures, into a quantifiable metric; however, S480 may alternatively comprise converting electromagnetic energy, received by a set of photodetectors from the set of nucleic acid-reagent mixtures, into a set of qualitative data. In one variation of Step S480, the set of data may be processed by a processor and rendered on a user interface; however, in other variations of Step S480, the set of data may alternatively not be rendered on a user interface.

The method 400 may further comprise re-running a biological sample S490 if processing and/or analysis of the biological sample results in less than ideal results. Preferably, Step S490 occurs if an analysis of a biological sample is indeterminate due to machine or user error. Additionally, Step S490 preferably occurs automatically upon detection of a less than ideal result, but may alternatively occur in response to a user prompt.

Embodiments of the method 400 and variations thereof can be embodied and/or implemented at least in part by a machine configured to receive a computer-readable medium storing computer-readable instructions. The instructions are preferably executed by computer-executable components preferably integrated with the system 100 and one or more portions of the processor 273 and/or the controller 272. The computer-readable medium can be stored on any suitable computer-readable media such as RAMs, ROMs, flash memory, EEPROMs, optical devices (CD or DVD), hard drives, floppy drives, or any suitable device. The computer-executable component is preferably a general or application specific processor, but any suitable dedicated hardware or hardware/firmware combination device can alternatively or additionally execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the preferred embodiments of the invention without departing from the scope of this invention defined in the following claims.

We claim:

1. A molecular diagnostic system configured to process a biological sample within a cartridge and separate a nucleic acid volume from the biological sample, the molecular diagnostic system comprising:
   a cartridge platform that supports the cartridge and comprising a magnet receiving slot configured to be aligned with the cartridge in a first operation mode;
   a nozzle of a liquid handling subsystem;
   an optical subsystem;
   a cartridge heater;
   a magnet vertically aligned with the magnet receiving slot; and
   an actuator coupled to the nozzle of the liquid handling subsystem, the optical subsystem, and the cartridge heater, the actuator configured to vertically displace the cartridge platform in the first operation mode to a position wherein:
      the nozzle of the liquid handling system is coupled to a fluid port of the cartridge, wherein the fluid port of the cartridge receives fluids for processing the biological sample,
      the magnet passes through the magnet receiving slot of the cartridge platform and interfaces with a first portion of the cartridge,
      the optical subsystem interfaces with a second portion of the cartridge, wherein the second portion of the cartridge receives a processed derivative of the nucleic acid volume, and
      a third region of the cartridge is compressed between the cartridge heater and the cartridge platform.

2. The system of claim 1, further including:
   a valve actuation subsystem comprising a set of pins, wherein the actuator vertically displaces the cartridge platform in the first operation mode to a position where the cartridge is positioned proximal the set of pins.

3. The system of claim 2, wherein in the first operation mode, the actuator provides a counterforce opposing the valve actuation subsystem, in cooperation with manipulation of the cartridge using the set of pins of the valve actuation subsystem.

4. The system of claim 2, further comprising:
a cam module configured to displace a subset of the set of pins of the valve actuation subsystem in the first operation mode to define a pathway, wherein the pathway facilitates separation of the nucleic acid volume from the biological sample, within the cartridge.

5. The system of claim 4, wherein the cam module includes a cam card coupled to a cam card actuator configured to linearly displace the cam card in interfacing with the set of pins.

6. The system of claim 5, wherein the cam card comprises a fixed set of hills and valleys, such that a pin of the set of pins is in a first position when a hill of the cam card interfaces with the pin, and the pin of the set of pins is in a second position when a valley of the cam card interfaces with the pin.

7. The system of claim 6, wherein at least one pin in the set of pins includes a spring configured to counteract a vertically oriented force provided by the cam card.

8. The system of claim 1, wherein the optical subsystem comprises at least one unit including an excitation filter, an emission filter, a photodetector aligned with the emission filter, and a dichroic mirror configured to reflect light from the excitation filter toward the biological sample, and to transmit emitted light from the biological sample, through the emission filter, and toward the photodetector.

9. The system of claim 1, wherein the magnet is arranged along a first side of the platform, and wherein the system further comprises a set of detection chamber heaters arranged along the first side of the platform.

10. The system of claim 9, wherein the cartridge heater is a plate heater directly coupled to the actuator and arranged along a second side of the platform opposing the first side, and wherein the first operation mode compresses the cartridge between the magnet and the detection chamber heaters at the first side, and the cartridge heater at the second side.

11. The system of claim 1, wherein at least one of the platform, the nozzle, the magnet, and the cartridge heater is coupled to a spring that provides a biasing force that maintains proper alignment of the cartridge within the molecular diagnostic system in response to motion of the actuator.

12. The system of claim 1, wherein the actuator is a scissor jack actuator having an extended configuration in the first operation mode, and a retracted configuration.

13. A method for processing a biological sample and separating a nucleic acid volume from the biological sample comprising:
receiving a cartridge between a cartridge platform of a molecular diagnostic system, the cartridge platform having a magnet receiving slot, and an actuator opposing the cartridge platform, the actuator coupled to a nozzle of a liquid handling subsystem, an optical subsystem, and a cartridge heater; and
with vertical displacement of the actuator, simultaneously:
coupling the nozzle to a fluid port of the cartridge for receiving fluids for processing the biological sample from a liquid handling system upstream of the nozzle,
passing a magnet through the magnet receiving slot to interface with a first portion of the cartridge,
interfacing the optical subsystem with a second portion of the cartridge for receiving a processed derivative of the nucleic acid volume, and
compressing a third region of the cartridge between the cartridge heater and the cartridge platform.

14. The method of claim 13, further comprising separating the nucleic acid volume from the biological sample within the cartridge at the first portion of the cartridge upon passing the magnet through the magnet receiving slot, with vertical displacement of the actuator.

15. The method of claim 14, wherein separating the nucleic acid volume from the biological sample comprises occluding a pathway of the cartridge at a first set of occlusion positions to define a first truncated pathway, overlapping with the first portion of the cartridge, and processing the biological sample in a first processing phase within the first truncated pathway.

16. The method of claim 13, further comprising driving waste fluid derived from the biological sample into a waste chamber of the cartridge, upon applying a positive pressure through the nozzle and into the cartridge.

17. The method of claim 13, further comprising providing a spring coupled to the platform, the spring configured to counteract a vertical force provided by the actuator.

18. The method of claim 13, further comprising: with vertical displacement of the actuator, bringing the cartridge into an active configuration that disposes the cartridge proximal a set of pins interfacing with a cam card.

19. The method of claim 18, further including: displacing a subset of the set of pins in the active configuration of the cartridge, with translation of the cam card relative to the set of pins, to occlude a pathway of the cartridge; and separating the nucleic acid volume from the biological sample, within the pathway of the cartridge.

20. The method of claim 19, wherein displacing the subset of the set of pins comprises linearly displacing the cam card, comprising a set of hills and valleys, relative to the set of pins, wherein displacing the cam card affects an interface between the set of pins and the set of hills and valleys to transition at least one pin of the set of pins between a first position and a second position.

* * * * *